(12) United States Patent
Drmanac et al.

(10) Patent No.: US 8,440,397 B2
(45) Date of Patent: *May 14, 2013

(54) HIGH THROUGHPUT GENOME SEQUENCING ON DNA ARRAYS

(75) Inventors: Radoje Drmanac, Los Altos Hills, CA (US); Matthew J. Callow, Redwood City, CA (US); Snezana Drmanac, Los Altos Hills, CA (US)

(73) Assignee: Callida Genomics, Inc., Sunnyvale, CA (US)

( * ) Notice: Subject to any disclaimer, the term of this patent is extended or adjusted under 35 U.S.C. 154(b) by 536 days.

This patent is subject to a terminal disclaimer.

(21) Appl. No.: 11/981,761

(22) Filed: Oct. 31, 2007

(65) Prior Publication Data

US 2009/0155781 A1    Jun. 18, 2009

Related U.S. Application Data

(63) Continuation of application No. 11/679,124, filed on Feb. 26, 2007, now abandoned.

(60) Provisional application No. 60/776,415, filed on Feb. 24, 2006, provisional application No. 60/821,960, filed on Aug. 10, 2006.

(51) Int. Cl.
  *C12Q 1/68* (2006.01)
  *C12P 19/34* (2006.01)
  *C12M 1/36* (2006.01)

(52) U.S. Cl.
  USPC ........ 435/6.1; 435/91.1; 435/91.2; 435/287.2; 536/23.1

(58) Field of Classification Search .......... None
  See application file for complete search history.

(56) References Cited

U.S. PATENT DOCUMENTS

| | | | |
|---|---|---|---|
| 4,318,846 A | 3/1982 | Khanna | 260/999.999 |
| 4,469,863 A | 9/1984 | Ts'o | 536/27 |

(Continued)

FOREIGN PATENT DOCUMENTS

| | | |
|---|---|---|
| WO | WO 91/17169 | 11/1991 |
| WO | WO 95/09248 | 4/1995 |

(Continued)

OTHER PUBLICATIONS

Bankier, "Shotgun DNA Sequencing," Methods in Mol. Biol., v. 167, p. 89-100, (2001).

(Continued)

*Primary Examiner* — Betty Forman
(74) *Attorney, Agent, or Firm* — Kilpatrick Townsend & Stockton LLP

(57) ABSTRACT

The present invention is directed to methods and compositions for acquiring nucleotide sequence information of target sequences using adaptors interspersed in target polynucleotides. The sequence information can be new, e.g. sequencing unknown nucleic acids, re-sequencing, or genotyping. The invention preferably includes methods for inserting a plurality of adaptors at spaced locations within a target polynucleotide or a fragment of a polynucleotide. Such adaptors may serve as platforms for interrogating adjacent sequences using various sequencing chemistries, such as those that identify nucleotides by primer extension, probe ligation, and the like. Encompassed in the invention are methods and compositions for the insertion of known adaptor sequences into target sequences, such that there is an interruption of contiguous target sequence with the adaptors. By sequencing both "upstream" and "downstream" of the adaptors, identification of entire target sequences may be accomplished.

25 Claims, 25 Drawing Sheets

U.S. PATENT DOCUMENTS

| | | | | |
|---|---|---|---|---|
| 4,719,179 A | 1/1988 | Barany | ...................... | 435/172.1 |
| 4,757,141 A | 7/1988 | Fung | ...................... | 536/27 |
| 4,849,336 A | 7/1989 | Miyoshi | ...................... | 435/6 |
| 4,883,750 A | 11/1989 | Whiteley | ...................... | 435/6 |
| 4,886,741 A | 12/1989 | Schwartz | ...................... | 435/5 |
| 5,034,506 A | 7/1991 | Summerton | ...................... | 528/391 |
| 5,066,580 A | 11/1991 | Lee | ...................... | 435/7.21 |
| 5,091,302 A | 2/1992 | Newman | ...................... | 435/6 |
| 5,091,519 A | 2/1992 | Cruickshank | ...................... | 536/29 |
| 5,124,246 A | 6/1992 | Urdea | ...................... | 435/6 |
| 5,143,854 A | 9/1992 | Pirrung | ...................... | 436/518 |
| 5,151,507 A | 9/1992 | Hobbs | ...................... | 536/23 |
| 5,188,934 A | 2/1993 | Menchen | ...................... | 435/6 |
| 5,198,537 A | 3/1993 | Huber | ...................... | 530/406 |
| 5,202,231 A | 4/1993 | Drmanac | ...................... | 435/6 |
| 5,216,141 A | 6/1993 | Benner | ...................... | 536/23 |
| 5,235,033 A | 8/1993 | Summerton | ...................... | 528/391 |
| 5,344,757 A | 9/1994 | Holtke | ...................... | 435/66 |
| 5,354,657 A | 10/1994 | Holtke | ...................... | 435/66 |
| 5,354,668 A | 10/1994 | Auerbach | ...................... | 435/91.1 |
| 5,366,860 A | 11/1994 | Bergot | ...................... | 435/66 |
| 5,386,023 A | 1/1995 | Sanghvi | ...................... | 536/25.3 |
| 5,403,708 A | 4/1995 | Brennan | ...................... | 435/6 |
| 5,426,180 A | 6/1995 | Kool | ...................... | 536/25.3 |
| 5,427,930 A | 6/1995 | Birkenmeyer | ...................... | 435/91.52 |
| 5,473,060 A | 12/1995 | Gryaznov | ...................... | 536/24.3 |
| 5,474,796 A | 12/1995 | Brennan | ...................... | 427/2.13 |
| 5,508,169 A | 4/1996 | Deugau | ...................... | 435/6 |
| 5,525,464 A | 6/1996 | Drmanac | ...................... | 435/6 |
| 5,571,677 A | 11/1996 | Gryaznov | ...................... | 435/6 |
| 5,602,240 A | 2/1997 | Mesmaeker | ...................... | 536/22.1 |
| 5,632,957 A | 5/1997 | Heller | ...................... | 422/68.1 |
| 5,637,684 A | 6/1997 | Cook | ...................... | 536/23.1 |
| 5,641,658 A | 6/1997 | Adams | ...................... | 435/91.2 |
| 5,644,048 A | 7/1997 | Yau | ...................... | 536/25.3 |
| 5,648,245 A | 7/1997 | Fire | ...................... | 435/91.1 |
| 5,688,648 A | 11/1997 | Mathies | ...................... | 435/6 |
| 5,702,888 A | 12/1997 | Holtke | ...................... | 435/6 |
| 5,710,000 A | 1/1998 | Sapolsky | ...................... | 435/6 |
| 5,714,320 A | 2/1998 | Kool | ...................... | 435/6 |
| 5,728,524 A | 3/1998 | Sibson | ...................... | 435/6 |
| 5,744,305 A | 4/1998 | Fodor | ...................... | 435/6 |
| 5,800,992 A | 9/1998 | Fodor | ...................... | 435/6 |
| 5,800,996 A | 9/1998 | Lee | ...................... | 435/6 |
| 5,847,162 A | 12/1998 | Lee | ...................... | 549/227 |
| 5,854,033 A | 12/1998 | Lizardi | ...................... | 435/91.2 |
| 5,866,337 A | 2/1999 | Schon | ...................... | 435/6 |
| 5,869,245 A | 2/1999 | Yeung | ...................... | 435/6 |
| 5,871,921 A | 2/1999 | Landegren | ...................... | 435/66 |
| 5,888,737 A | 3/1999 | DuBridge | ...................... | 435/6 |
| 5,916,750 A | 6/1999 | Iyer | ...................... | 435/6 |
| 5,990,479 A | 11/1999 | Weiss | ...................... | 250/307 |
| 5,994,068 A | 11/1999 | Guilfoyle | ...................... | 435/6 |
| 6,004,755 A | 12/1999 | Wang | ...................... | 435/6 |
| 6,013,445 A | 1/2000 | Albrecht | ...................... | 435/6 |
| 6,045,994 A | 4/2000 | Zabeau | ...................... | 435/6 |
| 6,077,668 A | 6/2000 | Kool | ...................... | 435/6 |
| 6,096,880 A | 8/2000 | Kool | ...................... | 536/25.3 |
| 6,124,120 A * | 9/2000 | Lizardi | ...................... | 435/91.2 |
| 6,136,537 A | 10/2000 | Macevicz | ...................... | 435/6 |
| 6,143,495 A | 11/2000 | Lizardi | ...................... | 435/6 |
| 6,143,527 A | 11/2000 | Pachuk | ...................... | 435/91.1 |
| 6,207,392 B1 | 3/2001 | Weiss | ...................... | 435/7.1 |
| 6,210,891 B1 | 4/2001 | Nyren | ...................... | 435/6 |
| 6,210,894 B1 | 4/2001 | Brennan | ...................... | 435/6 |
| 6,218,152 B1 | 4/2001 | Auerbach | ...................... | 435/91.2 |
| 6,221,603 B1 | 4/2001 | Mahtani | ...................... | 435/6 |
| 6,251,303 B1 | 6/2001 | Bawendi | ...................... | 252/301.4 |
| 6,255,469 B1 | 7/2001 | Seeman | ...................... | 536/23.1 |
| 6,258,539 B1 | 7/2001 | Hunkapillar | ...................... | 435/6 |
| 6,261,808 B1 | 7/2001 | Auerbach | ...................... | 435/91.1 |
| 6,270,961 B1 | 8/2001 | Drmanac | ...................... | 435/6 |
| 6,274,320 B1 | 8/2001 | Rothberg | ...................... | 435/6 |
| 6,274,323 B1 | 8/2001 | Bruchez | ...................... | 435/6 |
| 6,274,351 B1 | 8/2001 | Peponnet | ...................... | 435/91.1 |
| 6,284,497 B1 | 9/2001 | Sabanayagam | ...................... | 435/91.2 |
| 6,287,824 B1 | 9/2001 | Lizardi | ...................... | 435/91.2 |
| 6,289,144 B1 | 9/2001 | Neuschafer | ...................... | 385/12 |
| 6,291,183 B1 | 9/2001 | Pirrung | ...................... | 435/6 |
| 6,297,006 B1 | 10/2001 | Drmanac | ...................... | 435/6 |
| 6,297,016 B1 | 10/2001 | Egholm | ...................... | 435/6 |
| 6,306,597 B1 | 10/2001 | Macevicz | ...................... | 435/6 |
| 6,309,824 B1 | 10/2001 | Drmanac | ...................... | 435/6 |
| 6,316,229 B1 | 11/2001 | Lizardi | ...................... | 435/91.1 |
| 6,319,426 B1 | 11/2001 | Bawendi | ...................... | 252/301.4 |
| 6,322,901 B1 | 11/2001 | Bawendi | ...................... | 428/548 |
| 6,326,144 B1 | 12/2001 | Bawendi | ...................... | 435/6 |
| 6,329,150 B1 | 12/2001 | Lizardi | ...................... | 435/6 |
| 6,344,329 B1 | 2/2002 | Lizardi | ...................... | 435/6 |
| 6,346,413 B1 | 2/2002 | Fodor | ...................... | 435/287.2 |
| 6,355,432 B1 | 3/2002 | Fodor | ...................... | 435/6 |
| 6,401,267 B1 | 6/2002 | Drmanac | ...................... | 435/6 |
| 6,403,320 B1 | 6/2002 | Read | ...................... | 435/6 |
| 6,413,722 B1 | 7/2002 | Arnold | ...................... | 435/6 |
| 6,423,551 B1 | 7/2002 | Weiss | ...................... | 436/518 |
| 6,426,513 B1 | 7/2002 | Bawendi | ...................... | 257/13 |
| 6,432,360 B1 | 8/2002 | Church | ...................... | 422/68.1 |
| 6,444,143 B2 | 9/2002 | Bawendi | ...................... | 252/301.6 |
| 6,472,156 B1 | 10/2002 | Wittwer | ...................... | 435/6 |
| 6,489,103 B1 | 12/2002 | Griffiths | ...................... | 435/6 |
| 6,491,871 B1 | 12/2002 | Fodor | ...................... | 422/63 |
| 6,500,620 B2 | 12/2002 | Yu | ...................... | 435/6 |
| 6,514,768 B1 | 2/2003 | Guire | ...................... | 436/518 |
| 6,534,293 B1 | 3/2003 | Barany | ...................... | 435/91.2 |
| 6,558,928 B1 | 5/2003 | Landegren | ...................... | 435/91.1 |
| 6,573,369 B2 | 6/2003 | Henderson | ...................... | 536/23.1 |
| 6,576,291 B2 | 6/2003 | Bawendi | ...................... | 428/215 |
| 6,576,448 B2 | 6/2003 | Weissman | ...................... | 435/91.2 |
| 6,589,726 B1 | 7/2003 | Butler | ...................... | 435/4 |
| 6,610,481 B2 | 8/2003 | Koch | ...................... | 435/6 |
| 6,620,584 B1 | 9/2003 | Chee | ...................... | 435/6 |
| 6,632,609 B2 | 10/2003 | Lizardi | ...................... | 435/6 |
| 6,649,138 B2 | 11/2003 | Adams | ...................... | 423/403 |
| 6,653,077 B1 | 11/2003 | Brenner | ...................... | 435/6 |
| 6,654,505 B2 | 11/2003 | Bridgham | ...................... | 382/278 |
| 6,783,943 B2 | 8/2004 | Christian | ...................... | 435/6 |
| 6,787,308 B2 | 9/2004 | Balasubramanian | | |
| 6,812,005 B2 | 11/2004 | Fan | ...................... | 435/91.2 |
| 6,815,064 B2 | 11/2004 | Treadway | ...................... | 428/403 |
| 6,828,100 B1 | 12/2004 | Ronaghi | ...................... | 435/6 |
| 6,833,246 B2 | 12/2004 | Balasubramanian | ...................... | 435/6 |
| 6,864,052 B1 | 3/2005 | Drmanac | ...................... | 435/6 |
| 6,890,741 B2 | 5/2005 | Fan | ...................... | 435/91.2 |
| 6,911,345 B2 | 6/2005 | Quake | ...................... | 422/99 |
| 6,913,884 B2 | 7/2005 | Stuelpnagel | ...................... | 435/6 |
| 6,977,153 B2 | 12/2005 | Kumar | ...................... | 435/6 |
| 6,998,228 B2 | 2/2006 | Henderson | ...................... | 435/4 |
| 7,011,945 B2 | 3/2006 | Qiao | ...................... | 435/6 |
| 7,064,197 B1 | 6/2006 | Rabbani | ...................... | 536/24.3 |
| 7,244,559 B2 | 7/2007 | Rothberg | ...................... | 435/6 |
| 7,264,929 B2 | 9/2007 | Rothberg | ...................... | 435/6 |
| 7,276,720 B2 | 10/2007 | Ulmer | ...................... | 356/246 |
| 7,297,778 B2 | 11/2007 | Matsuzaki | ...................... | 536/22.1 |
| 7,335,762 B2 | 2/2008 | Rothberg | ...................... | 436/24.3 |
| 7,384,737 B2 * | 6/2008 | Barnes | ...................... | 435/6 |
| 7,544,473 B2 | 6/2009 | Brenner | ...................... | 435/6 |
| 7,910,302 B2 * | 3/2011 | Drmanac et al. | ...................... | 435/6.11 |
| 7,960,104 B2 * | 6/2011 | Drmanac et al. | ...................... | 435/6.11 |
| 2002/0004204 A1 | 1/2002 | O'Keefe | ...................... | 435/6 |
| 2002/0055100 A1 | 5/2002 | Kawashima | ...................... | 435/6 |
| 2002/0076716 A1 | 6/2002 | Sabanayagam | ...................... | 435/6 |
| 2002/0197621 A1 | 12/2002 | Drmanac | ...................... | 435/6 |
| 2003/0068629 A1 | 4/2003 | Rothberg | ...................... | 435/6 |
| 2003/0170914 A1 | 9/2003 | Guire | ...................... | 435/518 |
| 2004/0002090 A1 | 1/2004 | Mayer | ...................... | 435/6 |
| 2004/0224325 A1 | 11/2004 | Knapp | ...................... | 435/6 |
| 2004/0229221 A1 | 11/2004 | Schon | ...................... | 435/6 |
| 2004/0248144 A1 | 12/2004 | Mir | ...................... | 435/6 |
| 2004/0248161 A1 | 12/2004 | Rothberg | ...................... | 435/6 |
| 2005/0019776 A1 | 1/2005 | Callow et al. | | |
| 2005/0037356 A1 | 2/2005 | Gullberg | ...................... | 435/6 |
| 2005/0042649 A1 | 2/2005 | Balasubramanian | ...................... | 435/6 |
| 2005/0059022 A1 | 3/2005 | Ruan et al. | | |
| 2005/0079510 A1 | 4/2005 | Berka | ...................... | 435/6 |
| 2005/0100939 A1 | 5/2005 | Namsaraev | ...................... | 435/6 |
| 2005/0142577 A1 | 6/2005 | Jones | ...................... | 435/6 |
| 2005/0191656 A1 | 9/2005 | Drmanac | ...................... | 435/6 |

| | | |
|---|---|---|
| 2005/0214840 A1 | 9/2005 | Chen .......................... 435/6 |
| 2005/0227264 A1 | 10/2005 | Nobile ........................ 435/6 |
| 2005/0244863 A1 | 11/2005 | Mir ............................ 435/6 |
| 2006/0012793 A1 | 1/2006 | Harris ...................... 356/436 |
| 2006/0024681 A1 | 2/2006 | Smith ......................... 435/6 |
| 2006/0024711 A1 | 2/2006 | Lapidus ...................... 435/6 |
| 2006/0223097 A1 | 10/2006 | Sapolsky ..................... 435/6 |
| 2007/0015182 A1 | 1/2007 | Abarzua ...................... 435/6 |
| 2007/0092872 A1 | 4/2007 | Rothberg ..................... 435/6 |
| 2008/0318796 A1 | 12/2008 | Drmanac ...................... 506/3 |
| 2009/0099041 A1 | 4/2009 | Church et al. |
| 2009/0137414 A1 | 5/2009 | Drmanac ...................... 506/9 |
| 2009/0176652 A1 | 7/2009 | Dahl et al. |
| 2009/0203551 A1 | 8/2009 | Dahl et al. |
| 2009/0264299 A1 | 10/2009 | Drmanac ...................... 506/3 |

FOREIGN PATENT DOCUMENTS

| | | |
|---|---|---|
| WO | WO 01/62982 | 8/2001 |
| WO | WO 02/074988 | 9/2002 |
| WO | WO 02/077287 | 10/2002 |
| WO | WO 03/012119 | 2/2003 |
| WO | 03/102231 A1 | 12/2003 |
| WO | WO 03/106678 | 12/2003 |
| WO | WO 2004/072294 | 8/2004 |
| WO | WO 2004/076683 | 9/2004 |
| WO | WO 2005/040425 | 5/2005 |
| WO | WO 2005/047523 | 5/2005 |
| WO | WO 2005/078130 | 8/2005 |
| WO | WO 2005/080605 | 9/2005 |
| WO | WO 2005/082098 | 9/2005 |
| WO | WO 2005/093094 | 10/2005 |
| WO | WO 2005/116262 | 12/2005 |
| WO | WO 2006/007207 | 1/2006 |
| WO | WO 2006/040549 | 4/2006 |
| WO | WO 2006/055521 | 5/2006 |
| WO | WO 2006/073504 | 7/2006 |
| WO | WO 2006/074351 | 7/2006 |
| WO | WO 2006/084132 | 8/2006 |
| WO | WO 2007/014397 | 2/2007 |
| WO | WO 2007/025124 | 3/2007 |
| WO | WO 2007/061425 | 5/2007 |
| WO | WO 2007/062160 | 5/2007 |

OTHER PUBLICATIONS

Beattie et al., "Hybridization of DNA targets to glass-tethered oligonucleotide probes," Molecular Biotechnology, v. 4, issue 3, p. 213-225 (1995).
Blanco et al., "Highly efficient DNA synthesis by the phage phi 29 DNA polymerase," J. Biol. Chem., v. 264, issue 15, p. 8935-8940 (1989).
Brenner et al, "Gene Expression Analysis by Massivly Parallel Signature Sequencing (MPSS) on Microbead Arrays," Nature Biotechnology, v. 18, p. 630-634 (2000).
Collins et al, "Directional cloning of DNA fragments at a large distance from an initial probe: A circularization method," Proc. Natl. Acad. Sci., 81: 6812-6816 (1984).
Dempcy et al., "Synthesis of a thymidyl pentamer of deoxyribonucleic guanidine and binding studies with DNA homopolynucleotides," Proc. Natl. Acad. Sci. USA 92: 6097-6101 (1995).
Dressman et al., "Transforming single DNA molecules into fluorescent magnetic particles for detection and enumeration of genetic variations," Proc. Natl. Acad. Sci., 100: 8817-8822 (2003).
Guo, "Recent progress in nanoimprint technology and its applications," Journal of Physics D: Applied Physics, 37:R123-141 (2004).
Hirschhorn et al, "Genome-wide association studies for common diseases and complex traits," Nature Reviews Genetics, vol. 6, 95-108 (2005).
Jablonski et al., "Preparation of oligodeoxynucleotide-alkaline phosphatase conjugates and their use as hybridization probes," Nucleic Acids Research, vol. 14, p. 6115-6128 (1986).
Kojima et al., "PCR amplification from single DNA molecules on magnetic beads in emulsion: application for high-throughput screening of transcription factor targets," Nucleic Acids Research, 33 (17): e150 (2005).

Koshkin et al., "LNA (Locked Nucleic Acid): an RNA Mimic Forming Exceedingly Stable LNA Duplexes," J. Am. Chem. Soc. 120: 13252 3 (1998).
Kricka, "Stains, labels and detection strategies for nucleic acids assays," Ann. Clin. Biochem., vol. 39(2): 114-129 (2002).
Li et al., "A photocleavable fluorescent nucleotide for DNA sequencing and analysis," Proc. Natl. Acad. Sci., 100, 414-419 (2003).
Li et al., "BEAMing up for detection and quantification of rare wequence variants," Nature Methods, vol. 3, pp. 95-97 (2006).
Lieber, "The FEN-1 family of structure-specific nucleases in eukaryotic DNA replication, recombination and repair," BioEssays, vol. 19, pp. 233-340 (1997).
Margulies et al, "Genome sequencing in microfabricated high-density picolitre reactors," Nature, vol. 437, pp. 376-380 (2005).
Matthews et al., Analytical strategies for the use of DNA probes, Anal. Biochem., vol. 169, pp. 1-25 (1988).
Metzker, "Emerging Technologies in DNA Sequencing," Genome Research, 15: 1767-1776 (2005).
Mitra et al., "Fluorescent in situ sequencing on polymerase colonies," Anal. Biochem., vol. 320, pp. 55-65 (2003).
Musyanovych et al., "Miniemulsion Droplets as Single Molecule Nanoreactors for Polymerase Chain Reaction," Biomacromolecules, vol. 6 (4), pp. 1824-1828 (2005).
National Cancer Institute, Report of Working Group on Biomedical Technology, "Recommendation for a Human Cancer Genome Project, " (Feb. 2005).
Nie et al., "Quantitative Detection of Individual Cleaved DNA Molecules on Surfaces Using Gold Nanoparticles and Scanning Electron Microscope Imaging," Anal. Chem., vol. 78 (5), pp. 1528-1534 (2006).
Roe, "Shotgun Library Consturction for DNA Sequencing," Methods Mol. Biol., vol. 255, pp. 171-185 (2004).
Ronaghi et al., "A Sequencing Method Based on Real-Time Pyrophosphate," Science, vol. 281, pp. 363-365 (1998).
Service, Science, 311: 1544-1546 (2006).
Shendure et al, "Advanced Sequencing Technologies: Methods and Goals," Nature Reviews Genetics, vol. 5, pp. 335-344 (2004).
Tringe et al, "Metagenomics: DNA Sequencing of Environmental Samples," Nature Reviews Genetics, vol. 6, pp. 805-814 (2005).
Vingron et al., "Sequence Alignment and Penalty Choice Review of Concepts, Case Studies and Implications," J. Mol. Biol, vol. 235, issue 1, pp. 1-12 (1994).
Wetmur, et al. "DNA Probes: Applications of the Principles of Nucleic Acid Hybridization," Critical Reviews in Biochemistry and Molecular Biology, vol. 26, pp. 227-259 (1991).
Callow, Matthew J., et al. "Selective DNA amplification from complex genomes using universal double-sided adapters," Nucleic Acids Research, vol. 32, No. 2, e21, p. 1-6, (Jan. 2004).
Chen et al., "A Homogeneous, Ligase-Mediated DNA Diagnostic Test", Genome Research, vol. 8, No. 5, May 1998, pp. 549-556.
Cowie et al, "Identification of APC gene mutations in colorectal cancer using universal microarray-based combinatorial sequencing-by-hybridization," Human Mutation, 24:261-271 (2004).
Dahl et al., "Multiplex amplification enabled by selective circularization of large sets of genomic DNA fragments," Nucleic Acids Research, 33(8): e71 (2005).
Ladner, D.P. et al., "Multiplex detection of hotspot mutations by rolling circl-enabled universal microarrays," Laboratory Investigation, US and CA Academy of Pa;thology, vol. 81, No. 8, p. 1079-1086 (Aug. 1, 2001).
Shendure et al, "Accurate multiplex polony sequencing of an evolved bacterial genome," Science, 309: 1728-1732 (2005).
Smirnov et al, "Method of manufacturing whole-genome microarrays by rolling circle amplification," Genes, Chromosomes & Cancer, 40: 72-77 (2004).
Supplementary Search Report for EP Application No. 06815722.1, mailed on Dec. 22, 2009, 9 pages.

* cited by examiner

HIGH THROUGHPUT GENOME SEQUENCING ON DNA ARRAYS

CROSS-REFERENCE TO RELATED APPLICATIONS

This application is a continuation of U.S. application Ser. No. 11/679,124, filed Feb. 26, 2007 which claims priority to provisional application Ser. No. 60/776,415, filed Feb. 24, 2006 and Ser. No. 60/821,960 filed Aug. 10, 2006.

STATEMENT REGARDING FEDERALLY SPONSORED RESEARCH

This application has been partially funded by the Federal Government through Grant No. 1 U01 AI057315-01 of the National Institute of Health.

BACKGROUND OF THE INVENTION

Large-scale sequence analysis of genomic DNA is central to understanding a wide range of biological phenomena related to states of health and disease both in humans and in many economically important plants and animals, e.g. Collins et al (2003), Nature, 422: 835-847; Service, Science, 311: 1544-1546 (2006); Hirschhorn et al (2005), Nature Reviews Genetics, 6: 95-108; National Cancer Institute, Report of Working Group on Biomedical Technology, "Recommendation for a Human Cancer Genome Project," (February, 2005); Tringe et al (2005), Nature Reviews Genetics, 6: 805-814. The need for low-cost high-throughput sequencing and re-sequencing has led to the development of several new approaches that employ parallel analysis of many target DNA fragments simultaneously, e.g. Margulies et al, Nature, 437: 376-380 (2005); Shendure et al (2005), Science, 309: 1728-1732; Metzker (2005), Genome Research, 15: 1767-1776; Shendure et al (2004), Nature Reviews Genetics, 5: 335-344; Lapidus et al, U.S. patent publication US 2006/0024711; Drmanac et al, U.S. patent publication US 2005/0191656; Brenner et al, Nature Biotechnology, 18: 630-634 (2000); and the like. Such approaches reflect a variety of solutions for increasing target polynucleotide density in planar arrays and for obtaining increasing amounts of sequence information within each cycle of a particular sequence detection chemistry. Most of these new approaches are restricted to determining a few tens of nucleotides before signals become significantly degraded, thereby placing a limit on overall sequencing efficiency.

Another limitation of traditional high-throughput sequencing techniques is that random positioning of DNA targets over an array surface, which is used in many sequencing methods, reduces the packing efficiency of those targets from what is possible by attaching DNA at predefined sites such as in a grid.

In view of such limitations, it would be advantageous for the field if an additional approach were available to increase the amount of sequencing information that could be obtained from an array of target polynucleotides. Another need in the art is for an efficient and inexpensive way to prepare array supports with billions of binding sites at submicron sizes and distances.

SUMMARY OF THE INVENTION

Accordingly, in one aspect, the invention addresses the problems associated with short sequence read-lengths produced by many approaches to large-scale DNA sequencing, including the problem of obtaining limited sequence information per enzymatic cycle. Also provided are methods and compositions for preparing random arrays of engineered nucleic acid molecules able to support billions of molecules, including molecules at submicron sizes and distances.

In one aspect, the invention provides a method of determining the identification of a first nucleotide at a detection position of a target sequence, wherein the target sequence comprises a plurality of detection positions. In a preferred aspect, the method includes two steps: providing a plurality of concatemers and identifying the first nucleotide. Each concatemer comprises a plurality of monomers, and each monomer comprises: (i) a first target domain of the target sequence comprising a first set of target detection positions; (ii) a first adaptor comprising a Type IIs endonuclease restriction site; (iii) a second target domain of the target sequence comprising a second set of target detection positions; and (iv) a second interspersed adaptor comprising a Type IIs endonuclease restriction site. In a preferred embodiment, the target sequence concatemers are immobilized on a surface. In a further embodiment, the surface is functionalized.

In one embodiment, the invention provides a method of determining the identification of a first nucleotide at a detection position of a target sequence in which the identifying step comprises contacting the concatemers with a set of sequencing probes. In an exemplary embodiment, the sequencing probes each comprise a first domain complementary to one of the adaptors, a unique nucleotide at a first interrogation position, and a label. In a preferred embodiment, the contact between the concatemers and the sequencing probes is accomplished under conditions such that if the unique nucleotide is complementary to the first nucleotide, a sequencing probe hybridizes to the concatemer, thereby identifying the first nucleotide.

In another embodiment, each adaptor comprises an anchor probe, a hybridization site and an identifying step. The identifying step in an exemplary embodiment comprises: hybridizing anchor probes to anchor probe hybridization sites, hybridizing sequencing probes to target detection positions adjacent to the adaptors, ligating adjacent hybridized sequencing and anchor probes to form ligated probes, and detecting the ligated probes to identify the first nucleotide.

In another embodiment, each adaptor comprises an anchor probe hybridization site, and the identifying step comprises hybridizing anchor probes to the anchor probe hybridization sites and adding a polymerase and at least one dNTP comprising a label. The polymerase and the at least on dNTP are added under conditions whereby if the dNTP is perfectly complementary to a detection position, the dNTP is added to the anchor probe to form an extended probe, thereby creating an interrogation position of the extended probe. The first nucleotide is identified by determining the nucleotide at the interrogation position of the extended probe.

In a further embodiment of the invention, a nucleotide at a second detection position is identified. In still further embodiments of the invention, nucleotides at a third detection position, at a fourth detection position, at a fifth detection position, and/or at a sixth detection position is identified.

In one embodiment, the invention provides a method of determining the identification of a first nucleotide at a detection position of a target sequence, wherein the target sequence the target sequence concatemers are immobilized on a surface, and that surface comprises functional moieties including but not limited to amines, silanes, and hydroxyls. In a further embodiment, the surface comprises a plurality of spatially distinct regions comprising said immobilized concatemers. In a still further embodiment, the concatemers are immobilized on the surface using capture probes.

In one aspect, the invention provides a substrate comprising a plurality of immobilized concatemers, each monomer of said concatemer comprising: a first target sequence, a first adaptor comprising a Type IIs endonuclease restriction site, a second target sequence, and a second interspersed adaptor comprising a Type IIs endonuclease restriction site. The Type IIs endonuclease restriction site of the first adaptor may or may not be the same as the Type IIs endonuclease restriction site of the second adaptor. In a further embodiment, each monomer further comprises a third target sequence and a third interspersed adaptor comprising a Type IIs endonuclease restriction site, and in a still further embodiment, each monomer further comprises a fourth target sequence and a fourth interspersed adaptor comprising a Type IIs endonuclease restriction site.

In another aspect, the invention provides methods for inserting multiple adaptors in a target sequence. In a preferred aspect, the method includes the steps of: (i) ligating a first adaptor to one terminus of said target sequence, wherein the adaptor comprises a binding site for a restriction enzyme; circularizing the product from step (i) to create a first circular polynucleotide; cleaving the circular polynucleotide with a restriction enzyme, wherein the restriction enzyme is able to bind to the binding site within the first adaptor; ligating a second adaptor, wherein said second adaptor comprises a binding site for a restriction enzyme; and circularizing the product from step (iv) to create a second circular polynucleotide. In some embodiments, steps (iii) through (v) are repeated to insert a desired number of adaptors in the target sequence. In a preferred embodiment, the circularization step comprises adding a CircLigase™ enzyme.

In another embodiment, the circularization step comprises adding a circularization sequence to a second terminus of the target sequence, hybridizing a bridge template to at least a portion of the adaptor and a portion of the circularization sequence, and ligating the first and second termini together to circularize the target sequence.

In another aspect, the invention provides a method for identifying a nucleotide sequence of a target sequence. In this method, a plurality of interspersed adaptors is provided within the target sequence, and each interspersed adaptors has at least one boundary with the target sequence. At least one nucleotide adjacent to at least one boundary of at least two interspersed adaptors is identified, thereby identifying the nucleotide sequence of the target sequence.

In yet another aspect, the invention provides a library of polynucleotides. In a preferred aspect, the library comprises more than one nucleic acid fragment, and each fragment comprises a plurality of interspersed adaptors in a predetermined order. Each interspersed adaptor has at least one end that comprises a sequence which is not able to cross-hybridize with other sequences of other interspersed adaptors of the plurality. In a further preferred aspect, the predetermined order of interspersed adaptors is identical for every nucleic acid fragment.

In one aspect, the invention provides a method for identifying a nucleotide sequence of a target polynucleotide which comprises the steps of generating an amplicon from each of a plurality of fragments of the target polynucleotide and forming a random array of the amplicons, hybridizing one or more sequencing probes to the random array, determining the identity of at least one nucleotide adjacent to at least one interspersed adaptor by extending the one or more sequencing probes in a sequence specific reaction, and repeating the hybridization and identifying steps until a nucleotide sequence of the target polynucleotide is identified. In a preferred aspect, the sequencing probes are hybridized to the random array under conditions that permit the formation of perfectly matched duplexes between the one or more probes and complementary sequences on interspersed adaptors. In a preferred aspect, each fragment contains a plurality of interspersed adaptors at predetermined sites. In a further aspect, each amplicon comprises multiple copies of a fragment in numbers such that the fragments substantially cover the target polynucleotide. In a still further aspect, the amplicons of the random array are fixed to a surface at a density such that at least a majority of the amplicons is optically resolvable.

In another aspect, the invention provides a method of identifying a nucleotide sequence of a target sequence which comprises the steps of providing a random array of concatemers, hybridizing one or more probes from a first set of probes to the random array, hybridizing one or more probes from a second set of probes to the random array, ligating probes form the first and second sets which are hybridized to a target concatemer at contiguous sites, identifying the sequences of the ligated first and second probes, and repeating the hybridizing, ligating and identifying steps until the sequence of the target sequence is identified. In a preferred aspect, the random array of concatemers comprises concatemers fixed to a planar surface having an array of optically resolvable discrete spaced apart regions, and each concatemer comprises multiple copies of a fragment of the target polynucleotide, such that the number of different concatemers is such that their respective fragments substantially cover the target sequence. In a further aspect, each discrete spaced apart region has an area of less than 1 µm$^2$, such that substantially all the discrete spaced apart regions have at most one concatemer attached.

In still another aspect, the invention provides a method of identifying a nucleotide sequence of a target sequence which comprises generating a plurality of concatemers comprising multiple copies of a fragment of the target sequence, forming a random array of the concatemers fixed to a surface at a density such that at least a majority of the concatemers are optically resolvable, and identifying a sequence of at least a portion of each fragment adjacent to at least one interspersed adaptor in at least one concatemer, thereby identifying the nucleotide sequence of the target sequence.

DETAILED DESCRIPTION OF THE INVENTION

Figure 1A:
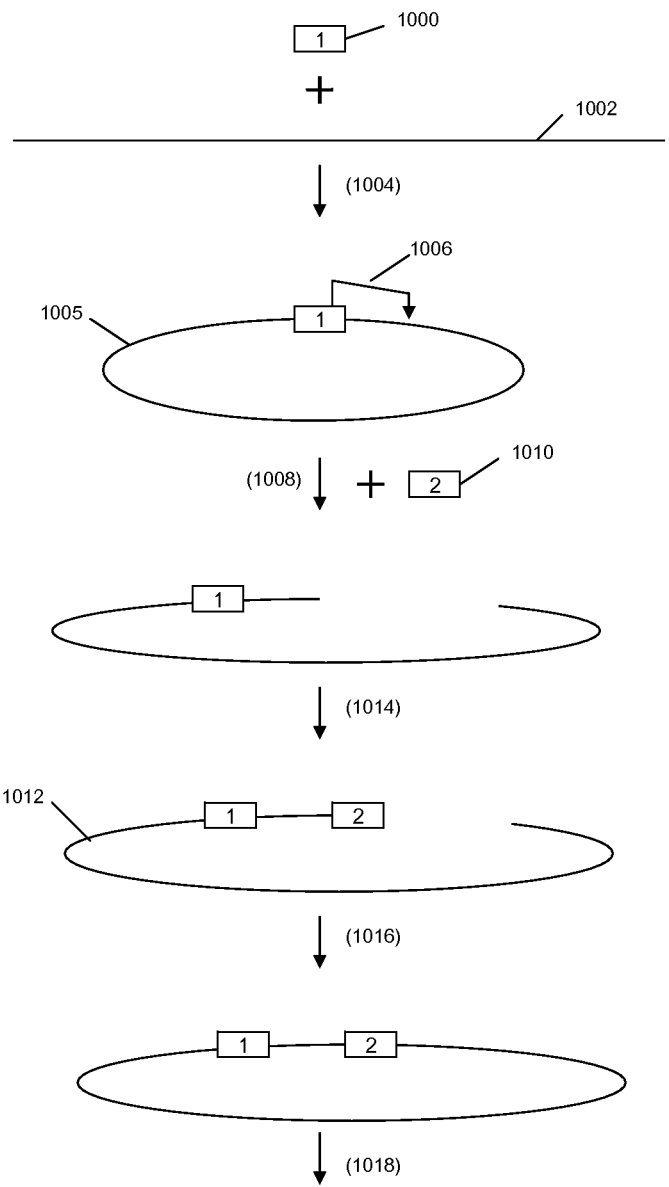
FIGS. 1A-1G illustrate the invention and applications thereof.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

Overview

The present invention is directed to methods and compositions for acquiring nucleotide sequence information of target sequences (also referred to herein as "target polynucleotides") using adaptors interspersed in target polynucleotides. The sequence information can be new, e.g. sequencing unknown nucleic acids, resequencing, or genotyping. The invention preferably includes methods for inserting a plurality of adaptors at spaced locations within a target polynucleotide or a fragment of a polynucleotide. Such adaptors are referred to herein as "interspersed adaptors", and may serve as platforms for interrogating adjacent sequences using various sequencing chemistries, such as those that identify nucleotides by primer extension, probe ligation, and the like. That is, one unique component of some embodiments of the invention is the insertion of known adaptor sequences into target sequences, such that there is an interruption of contiguous target sequence with the adaptors. By sequencing both "upstream" and "downstream" of the adaptor, sequence information of entire target sequences may be accomplished.

Accordingly, without limitation, the inventions can generally be described as follows (it should be noted that genomic DNA is used as an example herein, but is not meant to be limiting). Genomic DNA from any organism is isolated and fragmented into target sequences using standard techniques. A first adaptor is ligated to one terminus of the target sequence. The adaptor preferably comprises a Type IIs restriction endonuclease site, which cuts outside of the recognition sequence. If the enzyme results in a "sticky" end, the overhang portion can either be filled in or removed.

In one embodiment, an enzyme is used to ligate the two ends of the linear strand comprising the adaptor and the target sequence to form a circularized nucleic acid. This may be done using a single step. Alternatively, a second adaptor can be added to the other terminus of the target sequence (for example, a polyA tail), and then a bridging sequence can be hybridized to the two adaptors, followed by ligation. In either embodiment, a circular sequence is formed.

The circular sequence is then cut with the Type IIs endonuclease, resulting in a linear strand, and the process is repeated. This results in a circular sequence with adaptors interspersed at well defined locations within previously contiguous target sequences.

The circularized sequences are then amplified using a rolling circle replication (RCR) reaction, to form concatemers of the original target sequence (e.g. multimers of monomers). These long concatemers form "DNA nanoballs" ("DNBs") can then optionally be immobilized on a surface in a variety of ways, as outlined below.

Once on the surface, using the known adaptor sequences, sequencing of the intervening target sequences is done. As is known in the art, there are a number of techniques that can be used to detect or determine the identity of a base at a particular location in a target nucleic acid, including, but not limited to, the use of temperature, competitive hybridization of perfect and imperfect probes to the target sequence, sequencing by synthesis, for example using single base extension techniques (sometimes referred to as "minisequencing"), the oligonucleotide ligase amplification (OLA) reaction, rolling circle replication (RCR), allelic PCR, competitive hybridization and Invader™ technologies. Preferred embodiments include sequencing by hybridization with ligation, and sequencing by hybridization.

The sequence information can then be used to reconstruct sequences of larger target sequences, such as sequencing of the entire genomic DNA.

Sequencing large numbers of nucleic acids, as is necessary in applications such as genome analysis, epidemiological studies, and diagnostic tests, generally involves adapting sequencing technologies to high-throughput formats. However, there are drawbacks to traditional high-throughput sequencing techniques, particularly the problem of short sequence read lengths—that is, many high-throughput sequencing approaches are limited in the length and type of target polynucleotides that may be successfully sequenced. This limitation is primarily due to the number of contiguous bases that can be determined on a single fragment in a single operation. By providing a plurality of sites in each target polynucleotide or fragment from which to conduct particular sequencing chemistries, the present invention provides a multiplicity of adjacent sequence reads. In one aspect, these adjacent reads are contiguous, thereby effectively amplifying the expected read lengths of a large class of sequencing chemistries.

The present invention thus allows the determination of a longer contiguous or almost contiguous target sequence by determining the sequences on either side of adaptors.

Compositions/Structures of Target Polynucleotides

Accordingly, the present invention provides compositions and methods utilizing target sequences from samples. As will be appreciated by those in the art, the sample solution may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (i.e. in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.); as will be appreciated by those in the art, virtually any experimental manipulation may have been done on the samples.

In general, cells from the target organism (animal, avian, mammalian, etc.) are used. When genomic DNA is used, the amount of genomic DNA required for constructing arrays of the invention can vary widely. In one aspect, for mammalian-sized genomes, fragments are generated from at least about 10 genome-equivalents of DNA; and in another aspect, fragments are generated from at least about 30 genome-equivalents of DNA; and in another aspect, fragments are generated from at least about 60 genome-equivalents of DNA.

The target sequences or target polynucleotides are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. All of these references are hereby expressly incorporated by reference. These modifications of the ribose-phosphate backbone may be done to increase the stability and half-life of such molecules in physiological environments. For example, PNA:DNA hybrids can exhibit higher stability and thus may be used in some embodiments.

The nucleic acids may be single stranded or double stranded, as specified, or contain portions of both double stranded or single stranded sequence. The nucleic acids may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction, etc. It may be any length.

As is outlined more fully below, probes are made to hybridize to target sequences to determine the presence or absence of the target sequence in a sample. Generally speaking, this term will be understood by those skilled in the art. The target sequence may also be comprised of different target domains; for example, a first target domain of the sample target sequence may hybridize to a capture probe and a second target domain may hybridize to a label probe, etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

In one embodiment, genomic DNA, particular human genomic DNA, is used. Genomic DNA is obtained using conventional techniques, for example, as disclosed in Sambrook et al., supra, 1999; Current Protocols in Molecular Biology, Ausubel et al., eds. (John Wiley and Sons, Inc., NY, 1999), or the like, Important factors for isolating genomic DNA include the following: 1) the DNA is free of DNA processing enzymes and contaminating salts; 2) the entire genome is equally represented; and 3) the DNA fragments are between about 5,000 and 100,000 bp in length.

In many cases, no digestion of the extracted DNA is required because shear forces created during lysis and extraction will generate fragments in the desired range. In another embodiment, shorter fragments (1-5 kb) can be generated by enzymatic fragmentation using restriction endonucleases. In one embodiment, 10-100 genome-equivalents of DNA ensure that the population of fragments covers the entire genome. In some cases, it is advantageous to provide carrier DNA, e.g. unrelated circular synthetic double-stranded DNA, to be mixed and used with the sample DNA whenever only small amounts of sample DNA are available and there is danger of losses through nonspecific binding, e.g. to container walls and the like. In one embodiment, the DNA is denatured after fragmentation to produce single stranded fragments.

Target polynucleotides may be generated from a source nucleic acid, such as genomic DNA, by fragmentation to produce fragments of a specific size; in one embodiment, the fragments are 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length. These fragments may in turn be circularized for use in an RCR reaction or in other biochemical processes, such as the insertion of additional adaptors.

Polynucleotides of the invention have interspersed adaptors that permit acquisition of sequence information from multiple sites, either consecutively or simultaneously. Interspersed adaptors are oligonucleotides that are inserted at spaced locations within the interior region of a target polynucleotide. In one aspect, "interior" in reference to a target polynucleotide means a site internal to a target polynucleotide prior to processing, such as circularization and cleavage, that may introduce sequence inversions, or like transformations, which disrupt the ordering of nucleotides within a target polynucleotide.

In one aspect, as is more fully outlined below, interspersed adaptors are inserted at intervals within a contiguous region of a target polynucleotide. In some cases, such intervals have predetermined lengths, which may or may not be equal. In other cases, the spacing between interspersed adaptors may be known only to an accuracy of from one to a few nucleotides (e.g. from 1 to 15), or from one to a few tens of nucleotides (e.g. from 10 to 40), or from one to a few hundreds of nucleotides (e.g. from 100 to 200). Preferably, the ordering and number of interspersed adaptors within each target polynucleotide is known.

In some aspects of the invention, interspersed adaptors are used together with adaptors that are attached to the ends of target polynucleotides.

In one aspect, the invention provides target polynucleotides in the form of concatemers which contain multiple copies (e.g. "monomers") of a target polynucleotide or a fragment of a target polynucleotide. DNA concatemers under conventional conditions (a conventional DNA buffer, e.g. TE, SSC, SSPE, or the like, at room temperature) form random coils that roughly fill a spherical volume in solution having a diameter of from about 100 to 300 nm, which depends on the size of the DNA and buffer conditions, in a manner well known in the art, e.g. Edvinsson, "On the size and shape of polymers and polymer complexes," Dissertation 696 (University of Uppsala, 2002).

One measure of the size of a random coil polymer, such as single stranded DNA, is a root mean square of the end-to-end distance, which is roughly a measure of the diameter of the randomly coiled structure. Such diameter, referred to herein as a "random coil diameter," can be measured by light scatter, using instruments, such as a Zetasizer Nano System (Malvern Instruments, UK), or like instrument. Additional size measures of macromolecular structures of the invention include molecular weight, e.g. in Daltons, and total polymer length, which in the case of a branched polymer is the sum of the lengths of all its branches.

Upon attachment to a surface, depending on the attachment chemistry, density of linkages, the nature of the surface, and the like, single stranded polynucleotides fill a flattened spheroidal volume that on average is bounded by a region which is approximately equivalent to the diameter of a concatemer in random coil configuration. Preserving the compact form of the macromolecular structure on the surface allows a more intense signal to be produced by probes, e.g. fluorescently labeled oligonucleotides, specifically directed to components of a concatemer.

In some embodiments, classes of polynucleotides may be created by providing adaptors having different anchor probe binding sites. This type of "clustering" allows for increased efficiency in obtaining sequence information of the polynucleotides.

Methods of Fragmentation

Effective mapping strategies are needed for sequencing applications such as sequencing complex diploid genomes, de novo sequencing, and sequencing mixtures of genomes. In one embodiment, hierarchical fragmentation procedures are provided to identify haplotype information and assemble parental chromosomes for diploid genomes. Such procedures may also be applied to predicting protein alleles and to mapping short reads to the correct positions within a genome. Another use for such methods is the correct assignment of a mutation in a gene family which occurs within ~100 bases of DNA sequence shared between multiple genes.

FIG. (1C-D) illustrates one aspect of the invention, in which source nucleic acid (1600) (which may be, or contain, a single or several target polynucleotides) is treated (1601) to form single stranded fragments (1602), preferably in the range of from 50 to 600 nucleotides, and more preferably in the range of from 300 to 600 nucleotides, which are then ligated to adaptor oligonucleotides (1604) to form a population of adaptor-fragment conjugates (1606). Adaptor (1604) is usually an initial adaptor, which need not be "interspersed" in the sense that it separates two sequences which were contiguous in the original sequence. Source nucleic acid (1600) may be genomic DNA extracted from a sample using conventional techniques, or a cDNA or genomic library produced by conventional techniques, or synthetic DNA, or the like. Treatment (1601) usually entails fragmentation by a conventional technique, such as chemical fragmentation, enzymatic fragmentation, or mechanical fragmentation, followed by denaturation to produce single stranded DNA fragments.

In generating fragments in either stage, fragments may be derived from either an entire genome or from a selected subset of a genome. Many techniques are available for isolating or enriching fragments from a subset of a genome, as exemplified by the following references, which are incorporated in their entirety by reference: Kandpal et al (1990), Nucleic Acids Research, 18: 1789-1795; Callow et al, U.S. patent publication 2005/0019776; Zabeau et al, U.S. Pat. No. 6,045,994; Deugau et al, U.S. Pat. No. 5,508,169; Sibson, U.S. Pat. No. 5,728,524; Guilfoyle et al, U.S. Pat. No. 5,994,068; Jones et al, U.S. patent publication 2005/0142577; Gullberg et al, U.S. patent publication 2005/0037356; Matsuzaki et al, U.S. patent publication 2004/0067493; and the like.

In one embodiment, shear forces during lysis and extraction of genomic DNA generate fragments in a desired range. Also encompassed by the invention are methods of fragmentation utilizing restriction endonucleases.

In a preferred embodiment, particularly for mammalian-sized genomes, fragmentation is carried out in at least two stages, a first stage to generate a population of fragments in a size range of from about 100 kilobases (Kb) to about 250 kilobases, and a second stage, applied separately to each 100-250 Kb fragment, to generate fragments in the size range of from about 50 to 600 nucleotides, and more preferably in the range of from about 300 to 600 nucleotides, for generating concatemers for a random array. In some aspects of the invention, the first stage of fragmentation may also be employed to select a predetermined subset of such fragments, e.g. fragments containing genes that encode proteins of a signal transduction pathway, and the like.

In one embodiment, the sample genomic DNA is fragmented using techniques outlined in U.S. Ser. No. 11/451,692, hereby incorporated by reference in its entirety. In this aspect, genomic DNA is isolated as 30-300 kb sized fragments. Through proper dilution, a small subset of these fragments is, at random, placed in discreet wells of multi-well plates or similar accessories. For example a plate with 96, 384 or 1536 wells can be used for these fragment subsets. An optimal way to create these DNA aliquots is to isolate the DNA with a method that naturally fragments to high molecular weight forms, dilute to 10-30 genome equivalents after quantitation, and then split the entire preparation into 384 wells. This provides representation of all genomic sequences, and performing DNA isolation on 10-30 cells with 100% recovery efficiency assures that all chromosomal regions are represented with the same coverage. By providing aliquots in this method, the probability of placing two overlapping fragments from the same region of a chromosome into the same plate well is minimized. For diploid genomes represented with 10× coverage, there are 20 overlapping fragments on average to separate into distinct wells. If this sample is distributed over a 384 well plate, then each well contains, on average, 1,562 fragments. By forming 384 fractions in a standard 384-well plate, there is only about a 1/400 chance that two overlapping fragments may end up in the same well. Even if some matching fragments are placed in the same well, the other overlapping fragments from each chromosomal region provide the unique mapping information.

In one embodiment, the prepared groups of long fragments are further cut to the final fragment size of about 300 to 600 bases. To obtain sufficient (e.g., 10×) coverage of each fragment in a group, the DNA in each well may be amplified before final cutting using well-developed whole genome amplification methods.

All short fragments from one well may then be arrayed and sequenced on one separate unit array or in one section of a larger continuous matrix. A composite array of 384 unit arrays is ideal for parallel analysis of these groups of fragments. In the assembly of long sequences representing parental chromosomes, the algorithm may use the critical information that short fragments detected in one unit array belong to a limited number of longer continuous segments each representing a discreet portion of one chromosome. In almost all cases the homologous chromosomal segments may be analyzed on different unit arrays. Long (~100 Kb) continuous initial segments form a tailing pattern and provide sufficient mapping information to assemble each parental chromosome separately as depicted below by relying on about 100 polymorphic sites per 100 kb of DNA. In the following example dots represent 100-1000 consecutive bases that are identical in corresponding segments.

```
Well 3
......T........C..........C...G..........A.........

Well 20
....C........T..........T ...A....... .G..........C...

Well 157
........T. ..A...... ..G...    ...C........A...C...

Well 258
...C..........C...G..........A.........T........G...T....

Wells 3 and 258 assemble chromosome 1 of Parent 1:
...T........C..........C...G.......A..........T........G...T Wells 20 and 157 assemble chromosome 1 of Parent 2:
...C........T...... ..T...A..........G... ...C........A...C...
```

In one embodiment, amplification of the single targets obtained in the chromosomal separation procedure is accomplished using methods known in the art for whole genome amplification. In a preferred embodiment, methods that produce 10-100 fold amplification are used. In one embodiment, these procedures do not discriminate in terms of the sequences that are to be amplified but instead amplify all sequences within a sample. Such a procedure does not require intact amplification of entire 100 kb fragments, and shorter fragments, such as fragments from 1-10 kb, can be used.

Composition/Structure of Interspersed Adaptors

In one aspect, interspersed adaptors are inserted at intervals within a contiguous region of a target polynucleotide. Interspersed adaptors may vary widely in length, which depends in part on the number and type of functional elements desired. Such functional elements include, but are not limited to, anchor sequences, sequences complementary to capture probe sequences (e.g. for attachment to surfaces), tagging sequences, secondary structure sequences, sequences for attachment/hybridization of label probes, functionalization sequences, primer binding sites, recognition sites for nucleases, such as nicking enzymes, restriction endonucleases, and the like.

In one embodiment, the adaptors comprise a restriction endonuclease recognition site as known in the art. In one embodiment, such recognition sites can be for nicking enzymes.

In one embodiment, the restriction endonuclease site is a Type IIs restriction endonuclease site. Type-IIs endonucleases are generally commercially available and are well known in the art. Like their Type-II counterparts, Type-IIs endonucleases recognize specific sequences of nucleotide base pairs within a double stranded polynucleotide sequence. Upon recognizing that sequence, the endonuclease will cleave the polynucleotide sequence, generally leaving an overhang of one strand of the sequence, or "sticky end." Type-IIs endonucleases also generally cleave outside of their recognition sites; the distance may be anywhere from 2 to 20 nucleotides away from the recognition site. Because the cleavage occurs within an ambiguous portion of the polynucleotide sequence, it permits the capturing of the ambiguous sequence up to the cleavage site, under the methods of the present invention. Usually, type IIs restriction endonucleases are selected that have cleavage sites separated from their recognition sites by at least six nucleotides (i.e. the number of nucleotides between the end of the recognition site and the closest cleavage point). Exemplary type IIs restriction endonucleases include, but are not limited to, Eco57M I, Mme I, Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I, Taq II, and the like.

In some embodiments, each adaptor comprises the same Type IIs restriction endonuclease site. In alternative embodiments, different adaptors comprise different sites.

In one embodiment, one or more of the adaptors comprise anchor probe hybridization sites. As is outlined below, anchor probes are used in sequencing reactions, and can take a variety of forms. In general, at least one end of the anchor probe hybridization site is at the junction between the target sequence and the adaptor; that is, sequencing reactions generally rely on hybridization of the anchor probe directly adjacent to detection positions of the target sequence. The anchor or primer may be selected or designed to be or to have one to about ten or more, preferably one to four bases, shifted left or right from the target-adaptor junction. As used herein, "detection position" refers to a position in a target sequence for which sequence information is desired.

In many embodiments, sequencing reactions can be run off both ends of the anchor probes; thus, in some embodiments, the anchor probe hybridization site comprises the entire adaptor sequence. Alternatively, there may be two anchor probe hybridization sites within each adaptor; one adjacent or close to the 3' end of the target sequence and one adjacent or close to the 5' end. As will be appreciated by those in the art, depending on the length of the anchor probes and the length of the adaptor, two anchor probe hybridization sites may overlap within the adaptor, they may be directly adjacent, or they may be separated by intervening sequences. The length of the anchor probe hybridization sequence will vary depending on the conditions of the assay.

In one embodiment, one or more of the adaptors comprise a primer binding sequence. As is known in the art, polymerases generally require a single stranded template (the concatemers, for example) with a portion of double stranded nucleic acid. Essentially, any sequence can serve as a primer binding sequence, to bind a primer, as any double stranded sequence will be recognized by the polymerase. In general, the primer binding sequence is from about 3 to about 30 nucleotides in length, with from about 15 to about 25 being preferred. Primer oligonucleotides are usually 6 to 25 bases in length. As will be appreciated by those in the art, the primer binding sequence can be contained within any of the other adaptor sequences.

In one embodiment, one or more of the adaptors comprise a capture probe recognition sequence. As is more fully outlined below, one embodiment of the invention utilizes capture probes on the surface of a substrate to immobilize the DNBs. In this embodiment, the adaptors comprise a domain sufficiently complementary to one or more capture probes to allow hybridization of the domain and the capture probe, resulting in immobilization of the DNBs on the surface.

In one embodiment, one or more of the adaptors comprise a secondary structure sequence. For example, palindromic sequences in a plurality of adaptors within the concatemer results in hybridization between adaptors (e.g. intramolecular interactions between copies in the concatemer) thus "tightening" the three dimensional structure of the DNA nanoball ("DNBs"). These palindromic sequence units can be 5, 6, 7, 8, 9, 10 or more nucleotides in length and of various sequences, such as sequences chosen to provide a specific melting temperature. For example, a palindrome AAAAAAATTTTTTT (SEQ. ID NO. 8) will provide a 14 bases dsDNA hybrid between neighboring any two unit replicas in the form of:

```
        AAAAAAATTTTTTT      (SEQ. ID NO. 8)

TTTTTTTAAAAAAA      (SEQ. ID NO. 9)
```

In one embodiment, the adaptors comprise label probe binding sequences. In some embodiments, for example for detection of particular sequences rather than sequencing reactions, label probes can be added to the concatemers to detect particular sequences. Label probes will hybridize to the label probe binding sequence and comprise at least one detectable label, as is outlined herein. For example, detection of the presence of infectious agents such as bacteria or viruses can be done in this manner.

In one embodiment, the adaptors comprise tagging sequences. In this embodiment, tagging sequences may be used to pull out or purify circularized target sequences, concatemers, etc. In some embodiments, tagging sequences may include unique nucleic acid sequences that can be utilized to identify the origin of target sequences in mixtures of tagged samples, or can include components of ligand binding pairs, such as biotin/streptavidin, etc.

In one aspect, interspersed adaptors each have a length in the range of from 8 to 60 nucleotides; in another aspect, they have a length in the range of from 8 to 32 nucleotides; in another aspect, they have a length in a range selected from about 4 to about 400 nucleotides; from about 10 to about 100 nucleotides, from about 400 to about 4000 nucleotides, from about 10 to about 80 nucleotides, from about 20 to about 70 nucleotides, from about 30 to about 60 nucleotides, and from about 4 to about 10 nucleotides. Embodiments utilizing adaptors with a total length from about 20 to about 30 bases find particular use in several embodiments.

The number of interspersed adaptors inserted into target polynucleotides may vary widely and depends on a number of factors, including the sequencing/genotyping chemistry being used (and its read-length capacity), the particular length of the cleavage site of a particular Type IIs site, the number of nucleotides desired to be identified within each target polynucleotide, whether amplification steps are employed between insertions, and the like.

In one aspect, a plurality of interspersed adaptors are inserted at sites in a contiguous segment of a target polynucleotide; this may include two, three, four or more interspersed adaptors that are inserted at sites in a contiguous segment of a target polynucleotide. Alternatively, the number of interspersed adaptors inserted into a target polynucleotide ranges from 2 to 10; from 2 to 4; from 3 to 6; from 3 to 4; and from 4 to 6. In another aspect, interspersed adaptors may be inserted in one or both polynucleotide segments of a longer polynucleotide, e.g., 0.4-4 Kb in length, that have been ligated together directly or indirectly in a circularization operation (referred to herein as a "mate-pair"). In one aspect, such polynucleotide segments may be 4-400 (preferably 10-100) bases long.

It should also be noted that in general, the first adaptor attached to a target sequence is not "interspersed" or "inserted". That is, the first adaptor is generally attached to one terminus of the fragmented target sequence, and the subsequent adaptors are interspersed within a contiguous target sequence.

In one aspect, each member of a group of target polynucleotides has an adaptor with an identical anchor probe binding site and type IIs recognition site attached to a DNA fragment from source nucleic acid. In another embodiment, classes of polynucleotides may be created by providing adaptors having different anchor probe binding sites.

In one aspect, adaptors are inserted at intervals within a contiguous region of a target polynucleotide in which the intervals have pre-determined lengths. These pre-determined lengths may or may not be equal. In some embodiments the length of the intervals are known to an accuracy of about 1 to 200 nucleotides, in other embodiments from about 1-15, 10-40 and 100-200 nucleotides.

Interspersed adaptors may in accordance with the invention be single or double stranded.

In one aspect, adaptors include palindromic sequences, which foster intramolecular interactions within the target polynucleotide, resulting in a "nano-ball".

Methods for Inserting a Plurality of Adaptors

One aspect of the invention provides a method for producing a target polynucleotide having interspersed adaptors, as illustrated diagrammatically in FIGS. (1A-1B). In this method, target polynucleotide (1002) is combined with adaptor (1000), which may or may not be an interspersed adaptor, to form (1004) circle (1005), which may be either single stranded or double stranded. The target polynucleotide is generally obtained by fragmentation of a larger piece of DNA, such as chromosomal or other genomic DNA.

If double stranded DNA is used, then the ends of the fragments may be prepared for circularization by "polishing" and optional ligation of adaptors using conventional techniques, such as employed in conventional shotgun sequencing, e.g. Bankier, Methods Mol. Biol., 167: 89-100 (2001); Roe, Methods Mol. Biol., 255: 171-185 (2004); and the like.

In order to generate the next site for inserting a second interspersed adaptor, circle (1005) is typically rendered double stranded, at least temporarily. Adaptor (1000) is designed in this aspect of the invention to include a recognition site of a type IIs restriction endonuclease, which is oriented so that its cleavage site (1006) is interior to the target polynucleotide, shown, for example, to the right of adaptor (1000), thereby opening (1008) circle (1005). In a preferred embodiment, the method of inserting interspersed adaptors employs type IIs restriction endonucleases that leave 3' protruding strands after cleavage. For less precise insertion, a nicking enzyme may be used, or one strand of the first adaptor may be disabled from ligation, thus creating a nick that can be translated at an approximate distance and used to initiate polynucleotide cutting.

After the polynucleotide is cleaved, interspersed adaptor (1010) is ligated into place using conventional techniques to produce open circle (1012) containing two adaptors, which is then closed (1016) by ligation. The process is then repeated (1018): cleaving, inserting, and closing, until a desired number of interspersed adaptors, such as three, are inserted (1026) into target polynucleotide (1002), as shown in FIG. 1B. The final circle (1024) containing the interspersed adaptors may then be processed in a number of ways to obtain sequence information at sites in the target polynucleotide adjacent to at least one boundary of each interspersed adaptor.

Typically, sequences of a target polynucleotide are analyzed at or adjacent to one or both of the boundaries (e.g. 1021) between each interspersed adaptor and the target polynucleotide. In one aspect, final circle (1024), or a segment of it, may be amplified to generate an amplicon that is analyzed by a selected sequencing chemistry, such as one based on ligation or sequencing-by-synthesis. In one aspect, the first and last interspersed adaptors may be selected so that the region of final circle (1024) containing the interspersed adaptors can be cleaved (1038) from the circle, after which adaptors are ligated (1040) for amplification by polymerase chain reaction (PCR). Cleavage of the circle may be performed on one or two sites outside of adaptors 1 and 3. In another aspect, final circle (1024) may be used directly to generate amplicons by rolling circle replication (RCR), as described more fully below.

For applications in which many different target polynucleotides are analyzed in parallel, target polynucleotides having interspersed adaptors may be amplified using RCR or emulsion PCR as shown in FIGS. (1C-1D) and FIGS. (1E-1G), respectively.

In emulsion PCR, a mixture of fragments may be amplified, e.g. as disclosed by Margulies et al, Nature, 437: 376-380 (2005); Shendure et al (2005), Science, 309: 1728-1732; Berka et al, U.S. patent publication 2005/0079510; Church et al, PCT publication WO 2005/082098; Nobile et al, U.S. patent publication 2005/0227264; Griffiths et al, U.S. Pat. No. 6,489,103; Tillett et al, PCT publication WO 03/106678; Kojima et al, Nucleic Acids Research, 33 (17): e150 (2005); Dressman et al, Proc. Natl. Acad. Sci., 100: 8817-8822 (2003); Mitra et al, Anal. Biochem., 320: 55-65 (2003); Musyanovych et al, Biomacromolecules, 6: 1824-1828 (2005); Li et al, Nature Methods, 3: 95-97 (2006); and the like, which are incorporated herein by reference in their entirety for all purposes.

Figure 1B:
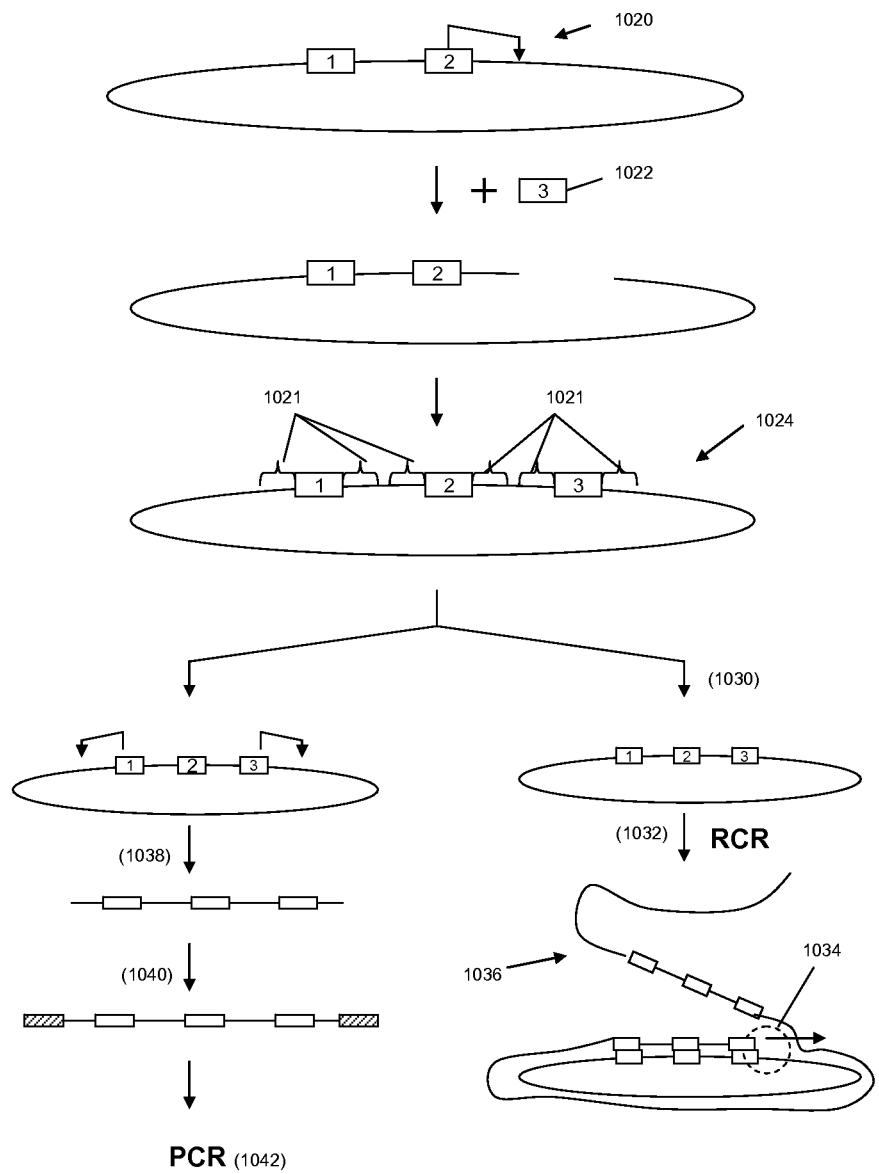

Briefly, as illustrated in FIG. (1E), after isolation of DNA circles (1500) comprising target polynucleotides with interspersed adaptors, the adaptors are excised, e.g. as shown in FIG. 1A (1038), to form a population of excised sequences, which are then ligated to adaptors (1503). The adaptored sequences are combined in a water-oil emulsion (1505) with primers specific for an adaptor ligated to one end of excised sequences, beads having attached primers specific for an adaptor ligated to the other end of excised sequences, and a DNA polymerase. Conditions are selected that permit a substantial number (e.g. greater than 15-20 percent) of aqueous bubbles (1508) in oil (1506) to contain a single adaptored sequence (1510) and at least one bead (1512). The aqueous phase in bubbles (1508) otherwise contain a conventional reaction mixture for conduction PCR, which results in beads (1518) each having a clonal population of a distinct adaptored sequence attached.

In one aspect of the invention, the introduction of multiple interspersed adaptors into a single genomic fragment proceeds through a series of steps involving 1) ligation of an initial adaptor harboring a binding site for a IIs restriction enzyme and closing the DNA circle, followed by 2) primer extension and selective restriction cutting of the genomic sequence to reopen the circle; and 3) ligation of second adaptor and closing the DNA circle. Steps 2 and 3 are then repeated to incorporate a third adaptor into the genomic sequence (FIGS. 2B and 2C). The second adaptor may utilize the same restriction site as the first adaptor to minimize cutting genomic segments at an internal site of the genomic DNA. In one embodiment, controlled cleavage using the recognition site of the second adaptor and not of the first adaptor is accomplished by blocking the cleavage at the first adaptor restriction site using techniques known in the art, such as by methylating the first restriction site prior to cutting at the second site.

Adaptors with different binding sites may be used with two aliquots of a sample to prevent exclusion of certain genomic fragments. In one embodiment, a part of the sequence of the final adaptor is used as an RCR priming site and another part of the adaptor is used as a binding site for an anchor oligonucleotide attached to a glass surface.

In one aspect of the invention, a method for inserting adaptors into a genomic fragment begins with ligation of a first adaptor followed by circle formation. Genomic fragments of 100 to 300 (or 300-600) bases in length may be prepared by DNAse fragmentation that generates 5-prime phosphates and 3-prime OH groups suitable for ligation. High-complexity genomic DNA can be prepared as single stranded (ss) DNA by heating (denaturation) and rapid cooling. Since the DNA is of high complexity, the localized concentration of the complementary sequence for any fragment may be negligible, thus allowing sufficient time to perform subsequent procedures when the DNA is mostly in the single stranded state. The use of ssDNA significantly simplifies circle formation because of the distinct polarity of 5' and 3' ends of each ssDNA fragment. The first stage is ligation of adaptor sequences to the ends of each single stranded genomic fragment. Since all possible sequence combinations may be represented in the genomic DNA, an adaptor can be ligated to one end with the aid of a bridging template molecule that is synthesized with all possible sequences (FIG. 2B). Since these oligonucleotides may be of relatively high concentration compared to the genomic DNA, the oligonucleotide that is complementary to the end of the genomic fragment (or a complement with mismatches) may hybridize. A bridge is thus formed at the ligation site to allow ligation of the 5-prime end of the single stranded genomic fragment to the adaptor. In one embodiment, this structural arrangement does not allow ligation of the adaptor to the 3-prime end of the fragment.

In FIG. 2B, another exemplary method is illustrated for incorporating multiple interspersed adaptors into DNA circles. Such method comprises the steps of: 1. Ligation of adaptors (230) to the 5' and 3' end of single stranded DNA (232) (the adaptors having degenerate (6-9 bases) bridge templates (234)) followed by ligation of the adaptors via a 3-base overhangs (236); 2. Extension (238) from the adaptor oligonucleotide with a polymerase to create double stranded DNA for type IIs restriction enzyme cutting; 3. A cut (242) at 12-16 bases downstream of the type IIs recognition site (240) opens the circle; 4. Heating results in loss of new strands (243); and 5. The fragment is ready for introduction of another adaptor (230) and closing the circle again.

Capture of the 3' end into the circle requires the use of an oligonucleotide template that again is prepared with degenerate bases so that a bridge structure is formed over the ligation site. The second adaptor section at the 3' end of the genomic fragment is used to close the circle with a 3-base overhang that is complementary to the end of the adaptor that bound at the 5' end. By performing the attachment of this adaptor segment at a temperature that favors hybridization of the template bridge (but not the 3 base overhang), the excess bridge molecule can be removed by buffer exchange since the genomic/adaptor molecule is attached to a solid support. A 3-base overhang is sufficient for circle formation but would not be favored until the temperature was decreased. The use of two bridging oligonucleotides with degenerate bases can eliminate artifacts created by the diverse sequence ends of the genomic DNA. In a preferred embodiment, both bridging oligonucleotides attach independently of each other to ensure freedom of the degenerate oligonucleotides to bind to their complementary sequences. Both of the adaptor components may be ligated to the respective DNA ends in the same ligation reaction and ligation artifacts can be further prevented by designing bridging template oligonucleotides with blocked ends.

The incorporation of a capture mechanism such as biotin/streptavidin onto the non-circle adaptor strand can be used in a down-stream cleanup processes. In such an embodiment, since both unligated and ligated biotynilated adaptors are present, the un-ligated excess adaptor can be removed by size selection of adaptor-genomic fragments that are ~200 bases in length. The adaptor-genomic fragments can then be attached to streptavidin coated beads for subsequent cleaning procedures. Another option is to use beads with a capture oligonucleotide (possibly incorporating PNA or LNA) complementary to a portion of one ligated adaptor. Beads with a pre-assembled left side of the first adaptor/template may be used to further simplify the process.

In FIG. 2C, another exemplary method for incorporating interspersed adaptors is illustrated. The method comprises the following steps: (1) Ligate two adaptor segments (250 and 252) to single stranded DNA fragments (254) using template oligonucleotides (the double stranded segment of 250 may be about 10 bases long, and the double stranded segment of 252 may be 8-10 bases long) containing degenerate bases (for example, segments 256 and 258 show the use of 7 degenerate bases, but 8 degenerate bases could also be used). Both ends of template oligonucleotides (250 and 256) are blocked from ligation with dideoxy termination on the 3' ends and either OH-group or biotin on the 5' ends. The adaptor/template hybrids are used at very high concentrations such as 1 µM and are in 1000-folds excess concentrations over genomic DNA. (2) DNA is collected on streptavidin support (260) via the biotin on the 5' end of the 3' adaptor (250). Excess free 5' adaptors are removed with the supernatant. (3) DNA is released from the streptavidin support by elevated temperature and the supernatant is collected. (4) DNA is recaptured to a solid support using a long capture oligonucleotide (262) with 3' end blocked by dideoxy termination. The oligonucleotide may be in the form of a peptide nucleic acid (PNA) to provide tight binding of the DNA to the solid support to facilitate removal of excess free adaptors in subsequent procedures. Capture oligonucleotide (262) can be extended by addition of 1-10 degenerate bases at the 5' end (264) for binding the genomic portion to increase stability. (5) The bridge template (266, which may be 14-18 bases long) is used to bring the two ends of the adaptors together to circularize the DNA molecule. It will be blocked on the 5' end with an amide group, but the 3'-OH group will be available for subsequent elongation by DNA polymerase in later steps. Kinase and ligase are provided in the reaction to phosphorylate the 5' end of the 5' adaptor and the ligation of the two ends of the DNA molecule.

In another exemplary capture procedure for inserting multiple adaptors, two adaptor segments are ligated to genomic ssDNA fragments using degenerate templates (FIG. 2C). The 3' end of the adaptor segment that ligates to the 5' end of the genomic DNA has a blocking complement. The template for the 3' adaptor segment has biotin. Adaptor/templates are in very high concentration such as 1 µM and have ~1000× high concentration from genomic DNA. DNA is collected on a streptavidin support and the solution is removed with the excess of adaptor components. The genomic DNA is released at an elevated temperature and the DNA solution is collected. The DNA is collected again on a second solid support with a long oligonucleotide (with blocked ends) complementary to the 5' end adaptor segment with removal of all other synthetic DNA. A bridging template is then added that serves also as a primer. Kinase and ligase (and polymerase) are added to close the circle and extend the primer to about 30 bases. Extension is controlled by time or by presence of ddNTPs. The enzymes are heat inactivated and the DNA is then cut with a type IIS restriction enzyme. The short double stranded portions are removed at elevated temperature with the circle attached to the solid support via a strong hybrid to the attached oligonucleotide. This stronger hybrid is maintained by incorporating LNA or PNA bases into the oligonucleotide. Two adaptor segments with templates for the second adaptor are then added (same design as above) no additional solid support attachment is required since the circle DNA will be continually associated with the solid support for further steps. Elevated temperatures are used to remove templates bound to the circular DNA. This step is repeated to insert a third adaptor. If no additional adaptors are to be inserted, then no polymerase is added and after a buffer exchange the DNA is released at elevated temperatures for the RCR reaction.

Figure 2A:
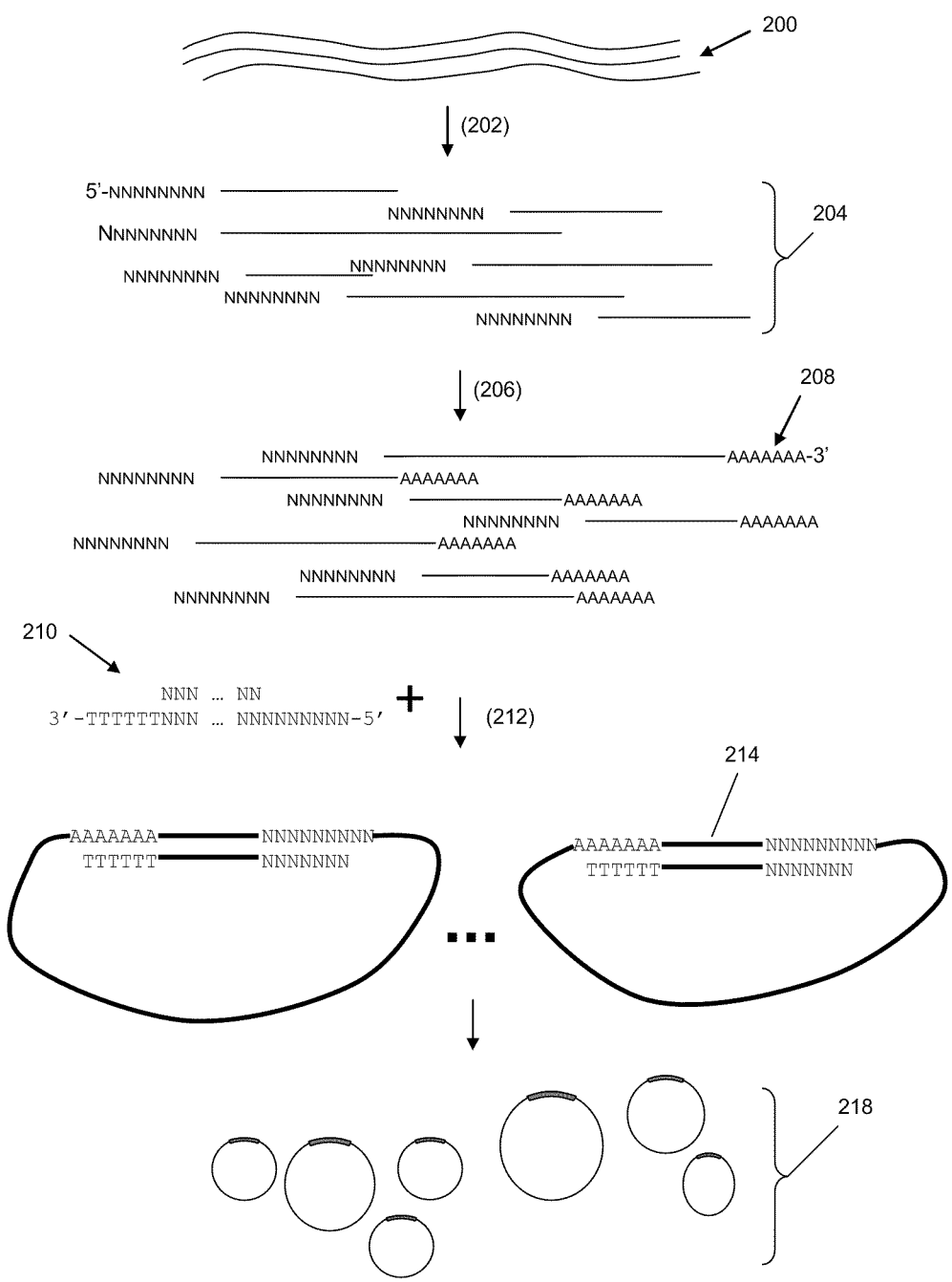
FIGS. 2A-2G illustrate various methods of inserting adaptors in a nucleic acid fragment to produce a target polynucleotide containing interspersed adaptors.
Figure 2B:
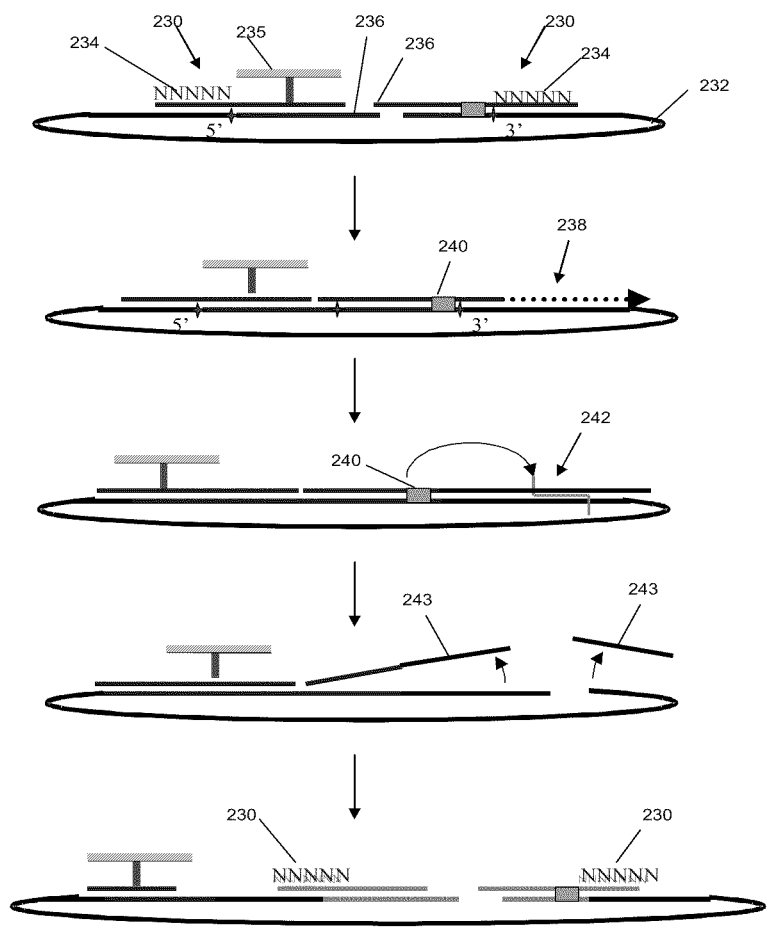
Figure 2C:
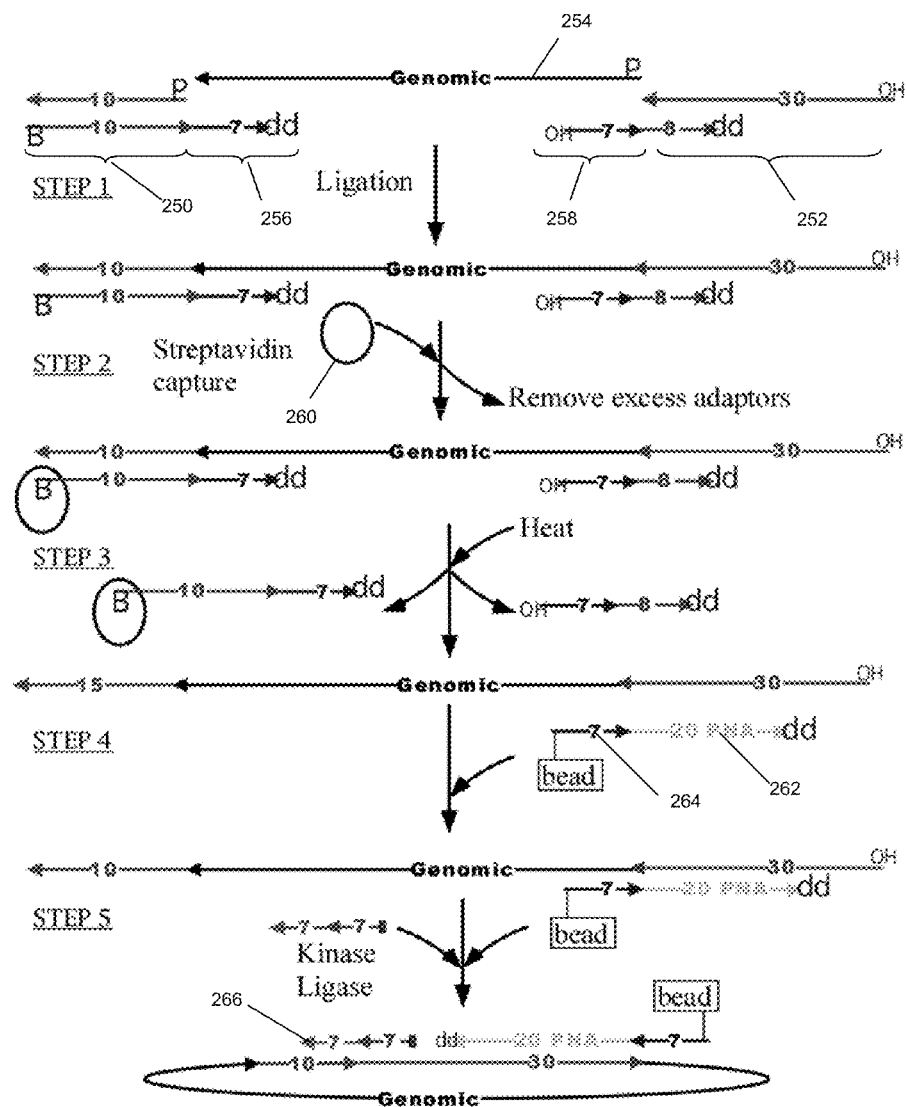
Figure 2D:
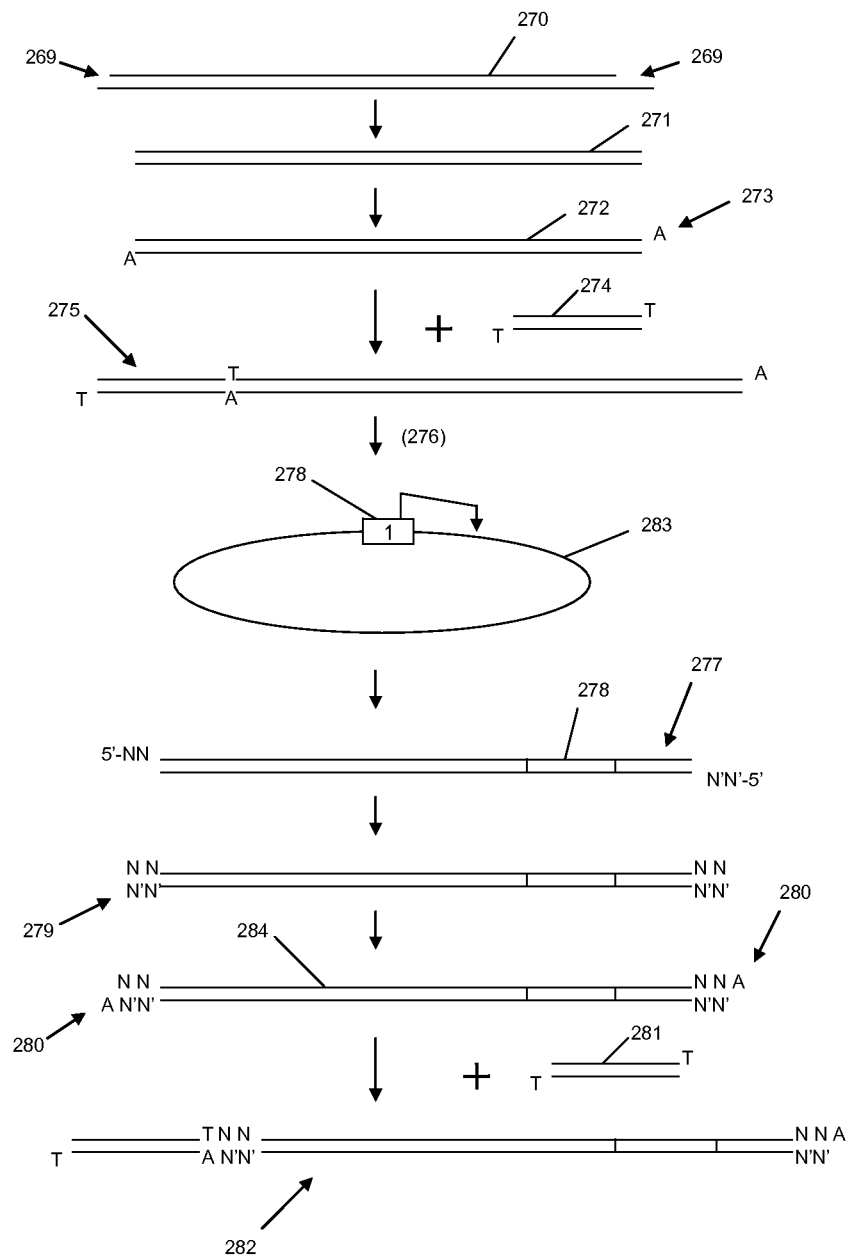

Another exemplary method of inserting interspersed adaptors is illustrated in FIG. 2D. This method generates segments of target polynucleotide with predetermined lengths adjacent to interspersed adaptors. The predetermined lengths are selected by selecting and positioning type IIs restriction endonucleases within the interspersed adaptors. In one aspect of this method, each different interspersed adaptor from the initial adaptor to the penultimate adaptor has a recognition site of a different type IIs restriction endonuclease. Double stranded DNA (dsDNA) is fragmented to produce target polynucleotides (270) having frayed ends (269), after which such ends are repaired using conventional techniques to form fragments (271) with blunt ends. To the 3' ends of blunt end fragments (271) a single nucleotide (273) is added, e.g. dA, using Taq polymerase, or like enzyme, to produce augmented fragments (272). Augmented fragments (272) are combined with interspersed adaptors (274) that have complementary nucleotide overhangs, e.g. dT, in the presence of a ligase so that multiple ligation products form, including product (275) that comprises a single interspersed adaptor and a single fragment. Conditions can be adjusted to promote the circularization (276) of product (275) so that dsDNA circles (283) are formed. Other products, such as conjugates with interspersed adaptors at both ends or unligated fragments and adaptors, will not generally have the ability to form circles and can be removed through digestion with a single stranded exonuclease after circularization of product (275).

dsDNA circles (283) are treated with a type IIs restriction endonuclease recognizing a site in adaptor (278) to cleave dsDNA circles (283) to leave segment (277) of target polynucleotide (270) adjacent to adaptor (278). In this embodiment, cleavage by the type IIs restriction endonuclease leaves 3' indented ends that are extended by a DNA polymerase to form blunt ends (279), after which fragment (284) is treated to add a single nucleotide to its 3' ends, as above. To fragment (284), a second interspersed adaptor (281) having complementary overhangs is ligated, and the process repeated to incorporate additional interspersed adaptors. In one embodiment, each cycle of interspersed adaptor incorporation includes an amplification step of the desired product to generate sufficient material for subsequent processing steps.

Figure 2E:
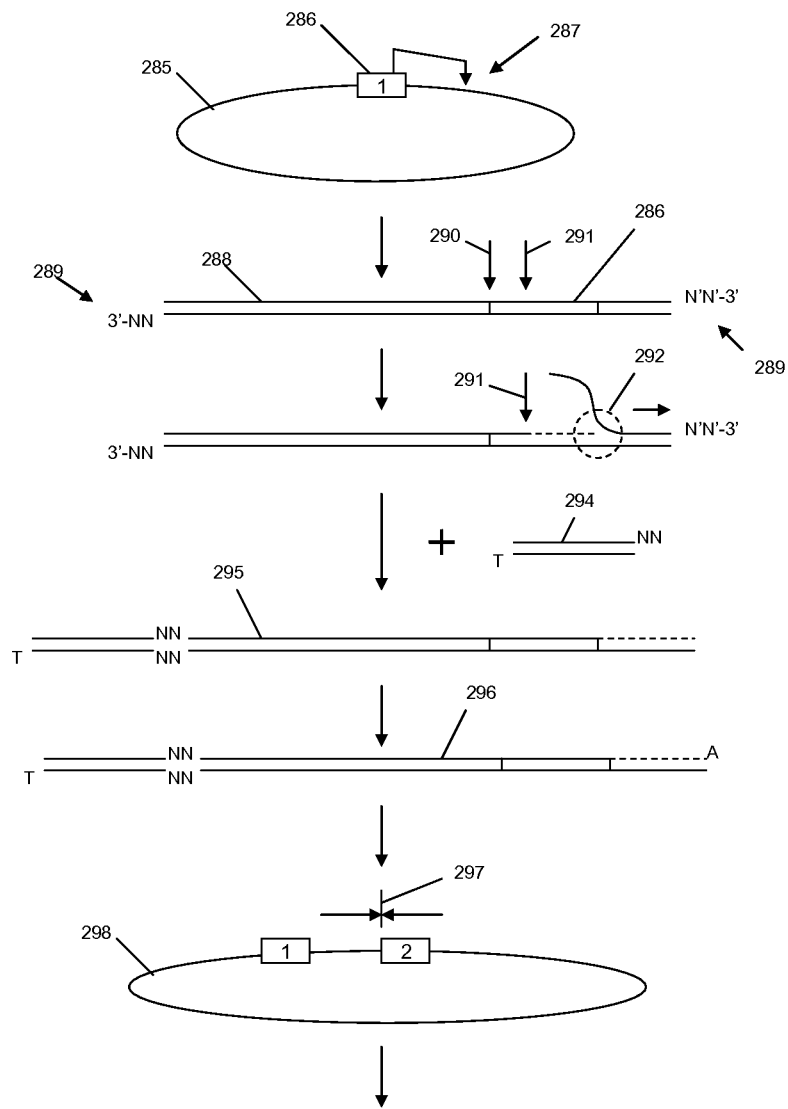

In FIG. 2E, another exemplary method is illustrated for incorporating interspersed adaptors at predetermined sites in a target polynucleotide. Fragments are generated as in FIG. 2D and dsDNA circles (285) are produced that have an initial interspersed adaptor (286) containing a type IIs recognition site, as described above, that cleaves dsDNA circle (285) at a predetermined site (287) to give fragment (288) having 3' overhangs (289), which may have lengths different than two. Interspersed adaptor of fragment (288) either contains a nick (290) at the boundary of the adaptor and the fragment or it contains the recognition site for a nicking endonuclease that permits the introduction of a nick (291) at the interior of the adaptor. In either case, fragment (288) is treated with a DNA polymerase (292) that can extend the upper strand from a nick (e.g. 291) to the end of the lower strand of fragment (288) to form a fragment having a 3' overhang at one end and a blunt end at the other. To this fragment is ligated an interspersed adaptor (294) that has degenerate nucleotide overhang at one end and a single 3' nucleotide (e.g. dT) overhang at the other end to form fragment (295), which is treated (e.g. with Taq polymerase) to add a 3' dA to its blunt end forming fragment (296). Fragment (296) is then circularized by ligation at site (297) to form dsDNA circle (298) and other ligation products are digested, as described above. Additional cycles of this process may be carried out to incorporate additional interspersed adaptors, and as above, optional steps of amplification may be added in each cycle, or as needed.

Figure 2F:
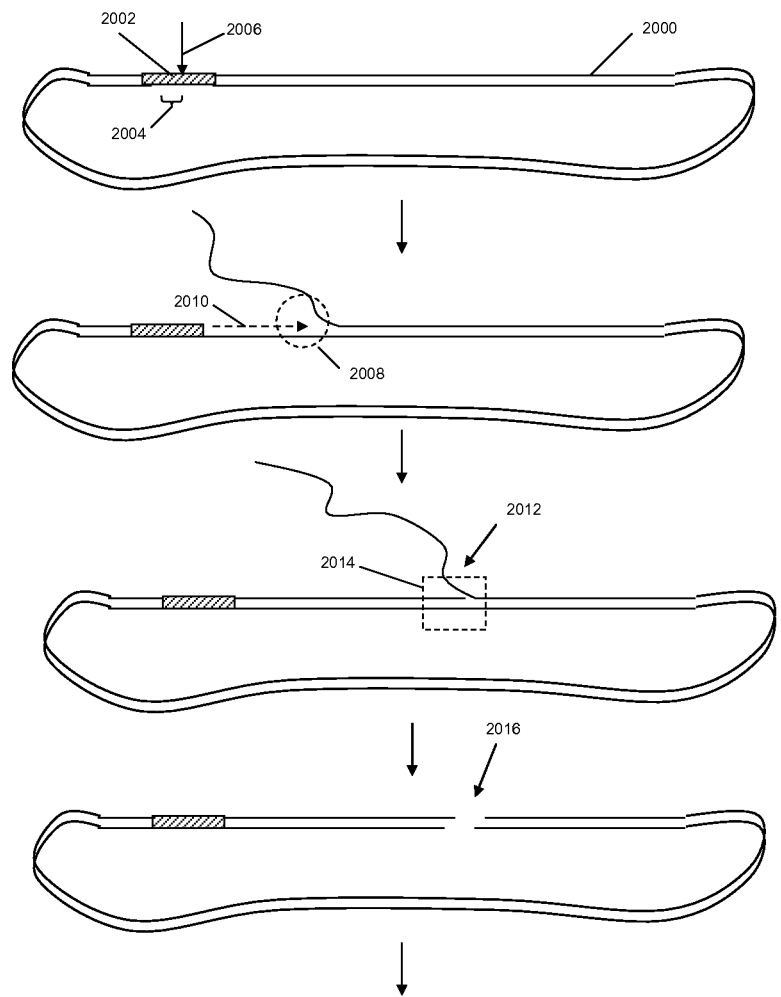
Figure 2G:
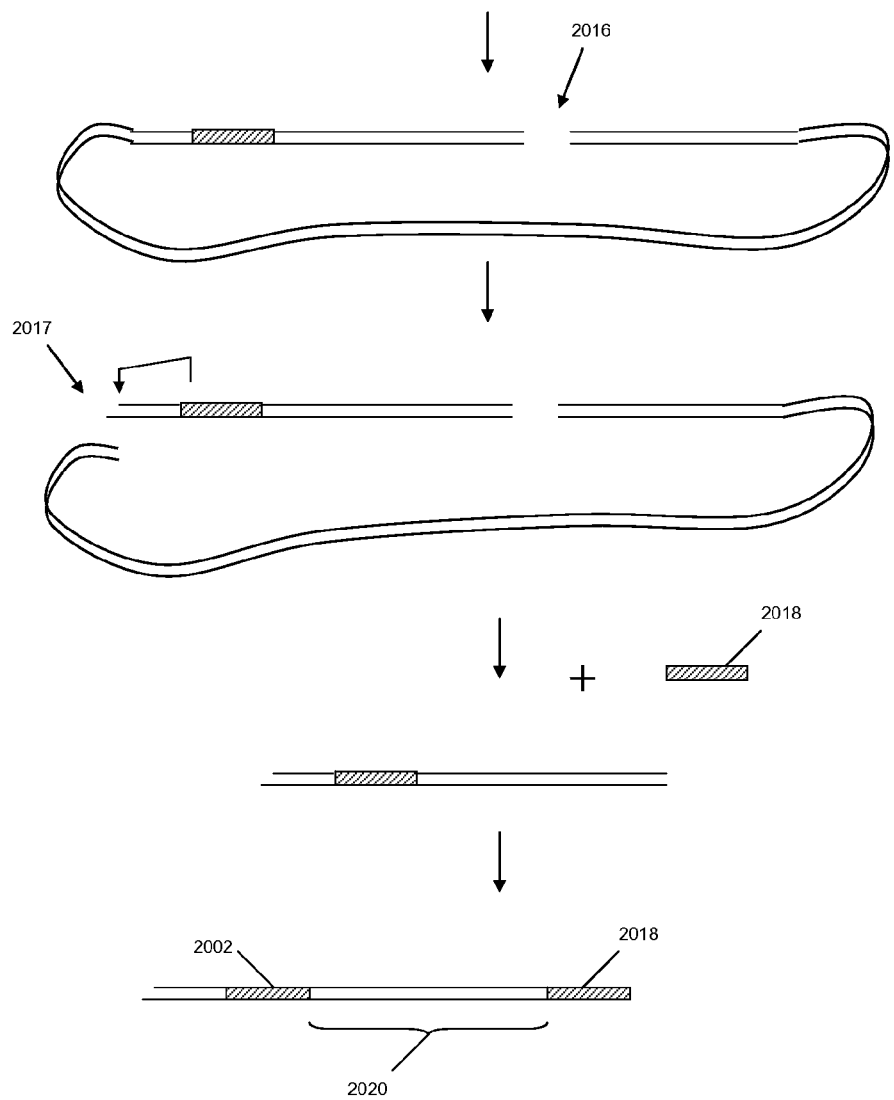

In FIG. 2F, another method of incorporating interspersed adaptors is illustrated that provides segments of variable lengths between interspersed adaptors. That is, interspersed adaptors are incorporated in a predetermined order, but at spacings that are not precisely known. This method allows incorporation of adaptors at distances longer than those provided by known restriction enzymes. As above, dsDNA circles (2000) are prepared having an initial adaptor (2002) (that may or may not be an interspersed adaptor) containing a recognition site (2004) for a nicking enzyme. After creation of nick (2006), dsDNA circle (2000) is treated with a DNA polymerase (2008) that extends (2010) the free 3' strand and displaces or degrades the strand with the free 5' end at nick site (2006). The reaction is stopped after a predetermined interval, which is selected to be shorter than the expected time to synthesize more than a few hundred bases. Such extension may be halted by a variety of methods, including changing reaction conditions such as temperature, salt concentration, or the like, to disable the polymerase being used. This leaves dsDNA circle with a nick or other gap (2012), which is recognized and cleaved by a variety of enzymes having nuclease activities, such as DNA polymerases, FEN-1 endonucleases, S1 nuclease (2014), and the like, which may be used alone or in combination, e.g. Lieber, BioEssays, 19: 233-340 (1997). After cleavage at nick or gap (2012), the ends of the target polynucleotide may be repaired using techniques employed in shotgun sequencing, after which target polynucleotide (2000) may be cleaved (2017) to the left of adaptor (2002) using a type IIs restriction endonuclease that leaves a staggered, or sticky, end. To the blunt end, the next interspersed adaptor is attached, after which the resulting construct may be circularized using conventional techniques for further insertions of interspersed adaptors. In one embodiment, the distances between successive interspersed adaptors, e.g. (2002) and (2018), are not known precisely and depend on the cleaving enzyme employed, the polymerase employed, the time interval allowed for synthesis, the method of stopping synthesis, reaction conditions, such as dNTP concentrations, and the like.

In one embodiment, at step (2010), nick translation can be used instead of strand displacement. In one aspect, in the polynucleotide break (2016) second adaptor may be ligated only to the sided connected to the first adaptor. This method can be combined with a second cut on the opposite side of the adaptor (2006) to create a mate-pair structure with various lengths of two segments such as (10-50)+(30-300) bases.

In one aspect, the invention provides a method for inserting adaptors using CircLigase™ to close single stranded polynucleotide circles without template. This enzyme provides the ability to use adaptors as single oligonucleotides and to use only one template. In this method, after an adaptor is ligated to the 5' end of the target polynucleotide using standard ligase such as T4 DNA ligase, the excess adaptor and template is removed. CircLigase™ (and kinase if the adaptor is not phosphorylated at the 5' end) can then be used to close single stranded polynucleotide circles.

In one embodiment, after the initial adaptor is inserted into the polynucleotide, it may need to be released from the support to be able to form a single stranded circle. The polynucleotide can then be re-hybridized to the support; in one embodiment, this re-hybridization occurs on a capture oligonucleotide which is bound to the surface of the support. A primer is added together with polymerase after closing the cycle for generating local dsDNA and allowing the cutting with type IIS restriction enzymes:

```
|-NNNNNNNUUUUUUUUUU-|
```

```
GGGGGGGGGGGGGG.UUUUUUUUUUUUUUUUUUUUUUUUU-5'OH  3'OH-GGGGGGGGG ...
```

Ligation of multiple adaptors may be prevented by starting with 5'OH or by having long blocking template possibly in the form of a hairpin:

```
|-NNNNNNNNUUUUUUUUUUUUUUUUUUUUUUUUUUUUUUUUUUU-Solid

UUUUUUUUUUUUUUUUUUUUUUUUUUUUUU-P  |-UUUUUU-|
where U = common base, N = degenerate base,
P = phosphate, G = genomic or DNA of interest.
```

Figure 9:
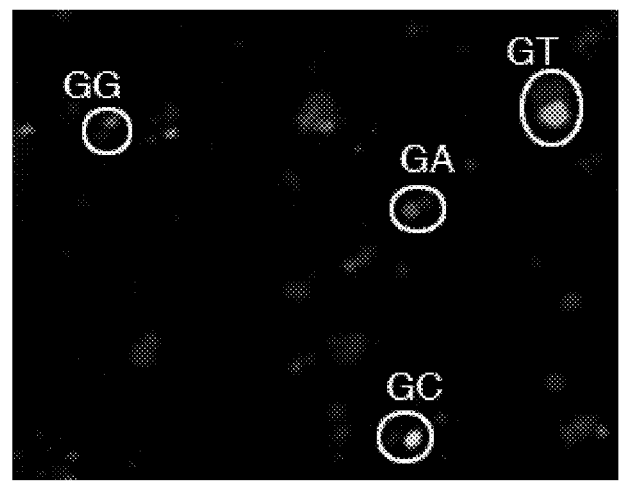
FIG. 9 shows five array images overlaid with slight shifts.
Figure 10:
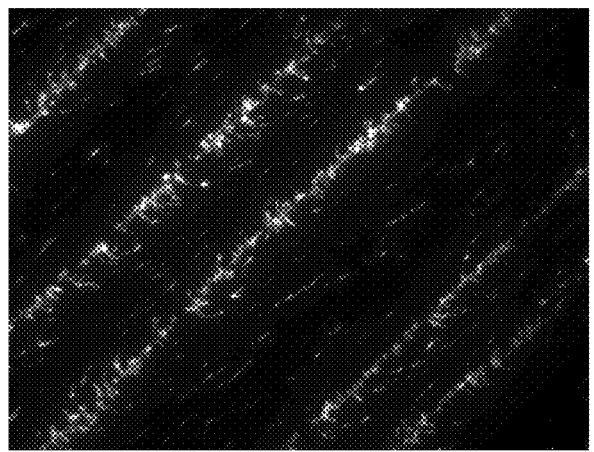
FIG. 10 shows an image of an array in which lines of capture probe across the surface of the coverslip were used to specifically bind to DNBs.

Once circle formation has occurred, a primer already prehybridized to the adaptor is extended with a polymerase to create enough double stranded DNA for type IIs restriction enzyme cutting allowing precise insertion of additional adaptors (FIG. 9). A polymerase such as Klenow may be used, along with a level of ddNTPs to control extension length to about 20-30 bases.

Inserting two additional adaptors can in some embodiments of the invention take 2-3 hours if each enzymatic step is accomplished in less than 30 minutes. Sporadic errors created in the adaptor insertion process can be tolerated because of the redundant tens of overlapping sequences generated for each base and because of probe-probe data that is generated on more than 100 bases of each DNA fragment that is not subjected to adaptor insertion.

In one exemplary method, multiple adaptors can be inserted by preparing dsDNA circles with a 50-100 bases +25 base mate-pair at >1 Kb distance. In this method, a dsDNA circle of a ~1-3 Kb genomic fragment is provided with an adaptor using A/T or blunt-end ligation. In one embodiment, the adaptor has a nicking enzyme binding site or it has one Uracil or other cleavable or photo-cleavable base analogs or one 3' end that is not ligated and recognition sites for two different IIS binding enzymes.

In one embodiment, the DNA is cut using a nicking enzyme or at Uracil sites and the available 3' end is extended (or just extended if adaptor ligation has left a nick) by ~75 bases with strand-displacement enzyme or nick translation enzyme; in the case of using a unligated 3' site, the displacement would be through the adaptor, e.g. the length would be 75 bases plus the length of the adaptor. The available 3' end may be removed by nick translation or by DNA synthesis with strand displacement. The cut can be at a nick or at a branched structure by one of several enzymes including single stranded cutting enzymes. This process results in a dsDNA fragment 30-110 bases next to one end of the initial adaptor. The DNA can then be cut with a Type IIS restriction endonuclease that has a long cutting distance. In one embodiment, the cutting distance is from 18 to 25 bases. The circle can be closed without adaptor (blunt end ligation of genomic fragments) or by directional blunt end ligation of a second adaptor. Both adaptors may be used for further insertion of additional adaptors using different or the same enzymes. If the first adaptor site is methylated before insertion of the second adaptor the second adaptor can use the same restriction site positioned at the proper distance from the adaptor end to obtain cutting at the specific position in the genomic DNA.

Methods of Circularization

Various standard DNA circle formation procedures may be used. One example is blunt end ligation of the adaptor. A problem with this approach is orientation and ligation of multiple incorporated adaptors. One strand of the cassette may have both the 5' and 3' ends blocked to ligation. Orientation of the cassette will determine which DNA strand will have a free 3' end to initiate RCR. This will allow each strand to be replicated in about 50% of cases.

```
DDDDDDDDDXLLLLLLLLLLLLLXDDDDDDDDDDD

DDDDDDDDDOLLLLLLLLLLLLLODDDDDDDDDDD

DDDDDDDDDOLLLLLLLLLLLLLODDDDDDDDDDD

DDDDDDDDDXLLLLLLLLLLLLLXDDDDDDDDDDD
D = DNA, L = adaptor, X = blocked ligation
site, O = open to ligation
```

As will be appreciated by those in the art, there are several ways to form circularized adaptor/target sequence components. In one embodiment, a CircLigase™ enzyme is used to close single stranded polynucleotide circles without template. Alternatively, a bridging template that is complementary to the two termini of the linear strand is used. In some embodiments, the addition of a first adaptor to one termini of the target sequence is used to design a complementary part of the bridging template. The other end may be universal template DNA containing degenerate bases for binding to all genomic sequences. Hybridization of the two termini followed by ligation results in a circularized component. Alternatively, the 3' end of the target molecule may be modified by addition of a poly-dA tail using terminal transferase. The modified target is then circularized using a bridging template complementary to the adaptor and to the oligo-dA tail.

In another embodiment, biotin is incorporated into each template oligonucleotide used to guide ligation. This allows for easy removal of templates, for example by applying high temperature melting, which removes the templates without removing formed circles. These longer oligonucleotides can serve as primers for RCR or be used for other purposes such as inserting additional cassettes.

In another embodiment, the target DNA may be attached to some solid support such as magnetic beads or tube/plate well walls to allow removal of all templates or adaptors that are not covalently ligated to the target DNA. Target ssDNA may be attached using a support with random primers to extend and create about 20-80 bases of dsDNA. The extension length may be controlled by time or by the amount of ddNTPs. Another approach is to ligate an adaptor to one end of the ssDNA and then size select DNA with the adaptor ligated to the ssDNA, and at the same time removing free adaptor. In this case an anchor sequence about 10-50 bases in length complementary to part of the adaptor may be attached to the support to capture DNA and use it for subsequent steps. This anchor molecule may have additional components to increase hybrid stability, such as the incorporation of a peptide nucleic acid. Another method for attaching single stranded DNA is by utilizing a single stranded DNA binding protein attached to the support.

In one method of circularization, illustrated in FIG. 2A, after genomic DNA (200) is fragmented and denatured (202), single stranded DNA fragments (204) are first treated with a terminal transferase (206) to attach a poly dA tails (208) to 3-prime ends. This is then followed by ligation (212) of the free ends intra-molecularly with the aid of bridging oligonucleotide (210) that is complementary to the poly dA tail at one end and complementary to any sequence at the other end by virtue of a segment of degenerate nucleotides. Duplex region (214) of bridging oligonucleotide (210) contains at least a primer binding site for RCR and, in some embodiments, sequences that provide complements to a capture oligonucleotide, which may be the same or different from the primer binding site sequence, or which may overlap the primer binding site sequence. The length of capture oligonucleotides may vary widely, In one aspect, capture oligonucleotides and their complements in a bridging oligonucleotide have lengths in the range of from 10 to 100 nucleotides; and more preferably, in the range of from 10 to 40 nucleotides. In some embodiments, duplex region (214) may contain additional elements, such as an oligonucleotide tag, for example, for identifying the source nucleic acid from which its associated DNA fragment came. That is, in some embodiments, circles or adaptor ligation or concatemers from different source nucleic acids may be prepared separately during which a bridging adaptor containing a unique tag is used, after which they are mixed for concatemer preparation or application to a surface to produce a random array. The associated fragments may be identified on such a random array by hybridizing a labeled tag complement to its corresponding tag sequences in the concatemers, or by sequencing the entire adaptor or the tag region of the adaptor. Circular products (218) may be conveniently isolated by a conventional purification column, digestion of non-circular DNA by one or more appropriate exonucleases, or both.

DNA fragments of the desired sized range, e.g. 50-600 nucleotides, can be circularized using circularizing enzymes, such as CircLigase, as single stranded DNA ligase that circularizes single stranded DNA without the need of a template. A preferred protocol for forming single stranded DNA circles comprising a DNA fragment and one or more adaptors is to use a standard ligase, such as T4 ligase, for ligating an adaptor to one end of a DNA fragment followed by application of CircLigase to close the circle.

In an exemplary method, a DNA circle comprising an adaptor oligonucleotide and a target sequence is generated using T4 ligase utilizes a target sequence that is a synthetic oligonucleotide T1N (sequence: 5'-NNNNNNNNGCATAN-CACGANGTCATNATCGTNCAAACGT-CAGTCCANGAATCNAGATCCACTTA-GANTGNCGNNNNNN-3') (SEQ ID NO: 1). The adaptor is made up of 2 separate oligonucleotides. The adaptor oligonucleotide that joins to the 5' end of T1N is BR2-ad (sequence: 5'-TATCATCTGGATGTTAGGAAGACAAAAG-GAAGCTGAGGACATTAACGGAC-3') (SEQ ID NO: 2) and the adaptor oligonucleotide that joins to the 3' end of T1N is UR3-ext (sequence: 5'-ACCTTCAGACCAGAT-3') (SEQ ID NO: 3).

UR3-ext contains a type IIs restriction enzyme site (Acu I: CTTCAG) to provide a way to linearize the DNA circular for insertion of a second adaptor. BR2-ad is annealed to BR2-temp (sequence 5'-NNNNNNNGTCCGTTAATGTCCT-CAG-3') (SEQ ID NO: 4) to form a double-stranded adaptor BR2 adaptor. UR3-ext is annealed to biotinylated UR3-temp (sequence 5'-[BIOTIN]ATCTGGTCTGAAGGT-NNNNNNN-3') (SEQ ID NO: 5) to form a double-stranded adaptor UR3 adaptor. 1 pmol of target T1N is ligated to 25 pmol of BR2 adaptor and 10 pmol of UR3 adaptor in a single ligation reaction containing 50 mM Tris-Cl, pH7.8, 10% PEG, 1 mM ATP, 50 mg/L BSA, 10 mM MgCl$_2$, 0.3 unit/µl T4 DNA ligase (Epicentre Biotechnologies, WI) and 10 mM DTT) in a final volume of 10 µl. The ligation reaction is incubated in a temperature cycling program of 15° C. for 11 min, 37° C. for 1 min repeated 18 times. The reaction is terminated by heating at 70° C. for 10 min. Excess BR2 adaptors are removed by capturing the ligated products with streptavidin magnetic beads (New England Biolabs, MA). 3.3 µl of 4× binding buffer (2M NaCl, 80 mM Tris HCl pH 7.5) is added to the ligation reaction, which is then combined with 15 µg of streptavidin magnetic beads in a 1× binding buffer (0.5M NaCl, 20 mM Tris HCl pH 7.5). After a 15 minute incubation in room temperature, the beads are washed twice with 4 volumes of low salt buffer (0.15M NaCl, 20 mM Tris HCl pH 7.5). Elution buffer (10 mM Tris HCl pH 7.5) is pre-warmed to 70 deg, 10 µl of which is added to the beads at 70° C. for 5 min. After magnetic separation, the supernatant is retained as primary purified sample. This sample can be further purified by removing the excess UR3 adaptors with magnetic beads pre-bound with a biotinylated oligonucleotide BR-rc-bio (sequence: 5'-[BIOTIN]CTTTTGTCTTCCTAA-CATCC-3') (SEQ ID NO: 6) that is reverse complementary to BR2-ad similarly as described above.

The concentration of the adaptor-target ligated product in the final purified sample can be estimated by urea polyacrylamide gel electrophoresis analysis. The circularization is carried out by phosphorylating the ligation products using 0.2 unit/µl T4 polynucleotide kinase (Epicentre Biotechnologies) in 1 mM ATP and standard buffer provided by the supplier, and circularized with ten-fold molar excess of a splint oligonucleotide UR3-closing-88 (sequence 5'-AGAT-GATAATCTGGTC-3') (SEQ ID NO: 7) using 0.3 unit/µl of T4 DNA ligase (Epicentre Biotechnologies) and 1 mM ATP. The circularized product is validated by performing RCR reactions.

In another exemplary embodiment, which is illustrated in FIG. 2A, adaptor oligonucleotides (1604), are used to form (1608) a population (1608) of DNA circles by the method illustrated in FIG. 2A. In one aspect, each member of population (1608) has an adaptor with an identical anchor probe binding site and type IIs recognition site attached to a DNA fragment from source nucleic acid (1600). The adaptor also may have other functional elements including, but not limited to, tagging sequences, sequences for attachment to a solid surface, restriction sites, functionalization sequences, and the like. Classes of DNA circles may be created by providing adaptors having different anchor probe binding sites.

After DNA circles (FIG. (2A) 1608) are formed, further interspersed adaptors are inserted as illustrated generally in FIG. (2A) to form circles (1612) containing interspersed adaptors. To these circles, a primer and rolling circle replication (RCR) reagents can be added to generate (1614) in a conventional RCR reaction a population (1616) of concatemers (1617) of the complements of the adaptor oligonucleotide and DNA fragments. This population can then be isolated or otherwise processed (e.g. size selected) (1618) using conventional techniques, e.g. a conventional spin column, or the like, to form population (1620) for analysis.

To demonstrate that the formation of multiple-adaptor DNA circles is feasible a synthetic target DNA of 70 bases in length and a PCR derived fragment of 200-300 bp in length may be obtained. A single stranded PCR fragment can be simply derived from a double stranded product by phosphorylation of one of the primers and treatment with lambda exonuclease to remove the phosphorylated strand. The single stranded fragment may be ligated to an adaptor for circularization. Polymerization, type IIs restriction enzyme digestion and re-ligation with a new adaptor may be performed as described herein.

Demonstration that the process was successful may proceed by RCR amplification of the final derived circles. Briefly, the DNA circles are incubated with primer complementary to the last introduced adaptor and phi29 polymerase for 1 hour at 30° C. to generate a single concatemer molecule comprising hundreds of repeated copies of the original DNA circle. Attachment of the RCR products to the surface of coverslips may proceed by utilizing an adaptor sequence in the concatemer that is complementary to an attached oligonucleotide on the surface. Hybridization of adaptor unique probes may be used to demonstrate that the individual adaptors were incorporated into the circle and ultimately the RCR product. To demonstrate that the adaptors were incorporated at the expected positions within the circle, sequence specific probes (labeled 5-mers) may be used for the synthetic or PCR derived sequence such that ligation may occur to an unlabeled anchor probe that recognizes the terminal sequence of the adaptor. Cloning and sequencing may also be used to verify DNA integrity.

In one embodiment, a template used for circle formation can also be used as a primer to create localized dsDNA. The schema is simplified by generating clean ssDNA after each circle cutting which allows the use of the same circle closing chemistry for each adaptor incorporations.

In one embodiment, a solution of DNA fragments with sticky ends or blunt ends is prepared for making DNA circles. The traditional method to avoid making circles with more than one DNA molecule is to perform ligation in a large volume at a low concentration of DNA fragments where intermolecular ligation is unlikely.

In a preferred embodiment, the ligation reaction does not require a large volume. This embodiment involves a slow addition of aliquots of DNA fragments into a regular size ligation reaction. Fast mixing of the DNA aliquot and the reaction minimizes multi-mer formation. The DNA fragments can be prepared in a ligation mix without ligase or in water or TE-like buffer. Typically, the DNA volume is equal to or lower than the initial volume of ligation reaction. DNA may be in a large volume in water or simple buffer (such as TE buffer) if the ligation reaction evaporates with the speed of adding the DNA sample. The evaporation may be simplified by using thermo-stabile ligase.

In one embodiment, the method of circularization involves diluting a small aliquot of DNA into a regular ligation reaction (such as 0.1-0.5 µl in 10-50 µl provides over 100 fold dilution) and waiting for sufficient time to allow a majority of the DNA to form circles, followed by addition of a second aliquot. In another embodiment, DNA fragments are slowly and continuously added.

Various physical implementations of the process are possible, such as manual or automated pipetting at a certain frequency, the use of drippers (gravity or positive pressure), piezo or acoustic spiting or nanodroppers, cavro-pumps that can deliver drops as small as 30 nl. In one embodiment 10 pmols in 100 µl reaction having maximal temporal concentration of 1 fmol/µl is processed using a consecutive addition of 100 aliquots. In another embodiment, 10 pmols are in 30-50 µl aliquots. The time to circularize >70-80% of DNA fragments in one aliquot depends on ligase concentration, type of ends (sticky 1, 2, or 4 bases or blunt) and to some extent temperature (movements and hybrid stability of sticky ends). In a preferred embodiment, the total time of the reaction is approximately 4-16 hours.

In one embodiment, a ligase enzyme is immobilized on a solid support, such as beads. DNA fragments are then diffused into ligation reaction from a gel block or other porous container using methods known in the art. To prevent ligation between fragments (rather than circularization), methods known in the art for temporarily blocking the DNA may be used, including but not limited to the use of non-ligatable DNA with matching sticky ends or ssDNA end binding proteins.

To increase the efficiency of flow-through of a small reaction volume, in one embodiment the reaction volume is dispensed under non-evaporating conditions, for example by using small droplets. Non-evaporating conditions can also be established by regulating humidity, temperature of the support ambient, and through design of the composition of reaction buffer. In en exemplary embodiment, 10 pl drops are dispensed by piezo spitting (~20×20×20 microns). With no spreading this is equivalent to a 20 micron thick flow cell. Spreading can be promoted to further reduce thickness of the volume to about 5-10 microns. To cover one $cm^2$ using 10 pl drops with zero spreading, 100×50×50=250,000 drops can be used.

In addition to piezo approach other forms of delivery of low amount of buffer per large surface can be used, such as by contacting the support with a porous material filled with reaction buffer or to move a long slit across the surface with a few 10-30 micron openings allowing dispensation of the buffer.

One exemplary method of circularization involves ligation of a single adaptor to dsDNA using two blocked complementary strands. In this method, two complementary strands of an adaptor are independently prepared. A matching blocking oligo that has uracils and can not be ligated to target DNA is also made for each of the two complementary strands. A dsDNA product comprising of one adaptor strand and one blocking oligo is assembled. Two assembled dsDNA constructs are designed that can not ligate or hybridize one to another; the constructs may be blunt end or may have a T overhang or other overhangs for ligation to DNA targets. A mixture of these two constructs is ligated to blunt end dsDNA or DNA with corresponding sticky ends. About 50% of DNA will have one of each construct; the other 50% will have two of the same construct. The blocking oligo is then degraded, and the circle is closed by hybridization of complimentary strands and ligation.

In one embodiment, the adaptor may be palindromic to avoid distinction of orientation. Such an approach can provide a better yield than A/T ligation approach, depending on blunt end ligation efficiency and concentration of DNA in A/T ligation reaction. In a further embodiment, four instead of two ssDNA adaptor components are used.

Methods for Creating Concatemers

In one aspect of the invention, single molecules comprise concatemers of polynucleotides, usually polynucleotide analytes, i.e. target sequences, that have been produce in a conventional rolling circle replication (RCR) reaction. Guidance for selecting conditions and reagents for RCR reactions is available in many references available to those of ordinary skill, as evidence by the following that are incorporated by reference: Kool, U.S. Pat. No. 5,426,180; Lizardi, U.S. Pat. Nos. 5,854,033 and 6,143,495; Landegren, U.S. Pat. No. 5,871,921; and the like. Generally, RCR reaction components comprise single stranded DNA circles, one or more primers that anneal to DNA circles, a DNA polymerase having strand displacement activity to extend the 3' ends of primers annealed to DNA circles, nucleoside triphosphates, and a conventional polymerase reaction buffer. Such components are combined under conditions that permit primers to anneal to DNA circles and be extended by the DNA polymerase to form concatemers of DNA circle complements. An exemplary RCR reaction protocol is as follows: In a 50 µL reaction mixture, the following ingredients are assembled: 2-50 pmol circular DNA, 0.5 units/µL phage φ29 DNA polymerase, 0.2

µg/µL BSA, 3 mM dNTP, 1×φ29 DNA polymerase reaction buffer (Amersham). The RCR reaction is carried out at 30° C. for 12 hours. In some embodiments, the concentration of circular DNA in the polymerase reaction may be selected to be low (approximately 10-100 billion circles per ml, or 10-100 circles per picoliter) to avoid entanglement and other intermolecular interactions.

Preferably, concatemers produced by RCR are approximately uniform in size; accordingly, in some embodiments, methods of making arrays of the invention may include a step of size-selecting concatemers. For example, in one aspect, concatemers are selected that as a population have a coefficient of variation in molecular weight of less than about 30%; and in another embodiment, less than about 20%. In one aspect, size uniformity is further improved by adding low concentrations of chain terminators, such ddNTPs, to the RCR reaction mixture to reduce the presence of very large concatemers, e.g. produced by DNA circles that are synthesized at a higher rate by polymerases. In one embodiment, concentrations of ddNTPs are used that result in an expected concatemer size in the range of from 50-250 Kb, or in the range of from 50-100 Kb. In another aspect, concatemers may be enriched for a particular size range using a conventional separation techniques, e.g. size-exclusion chromatography, membrane filtration, or the like.

An exemplary method for producing concatemers is illustrated in FIG. 2A. After DNA circles (1608) are formed, further interspersed adaptors are inserted as illustrated generally in FIG. (2A) to form circles (1612) containing interspersed adaptors. To these circles, a primer and rolling circle replication (RCR) reagents can be added to generate (1614) in a conventional RCR reaction a population (1616) of concatemers (1617) of the complements of the adaptor oligonucleotide and DNA fragments. This population can then be isolated or otherwise processed (e.g. size selected) (1618) using conventional techniques, e.g. a conventional spin column, and the like, to form population (1620) for analysis.

Target polynucleotides may be generated from a source nucleic acid, such as genomic DNA, by fragmentation to produce fragments 0.2-2 kb in size, or more preferably, 0.3-0.6 kb in size, which then may be circularized for an RCR reaction.

Figure 1C:
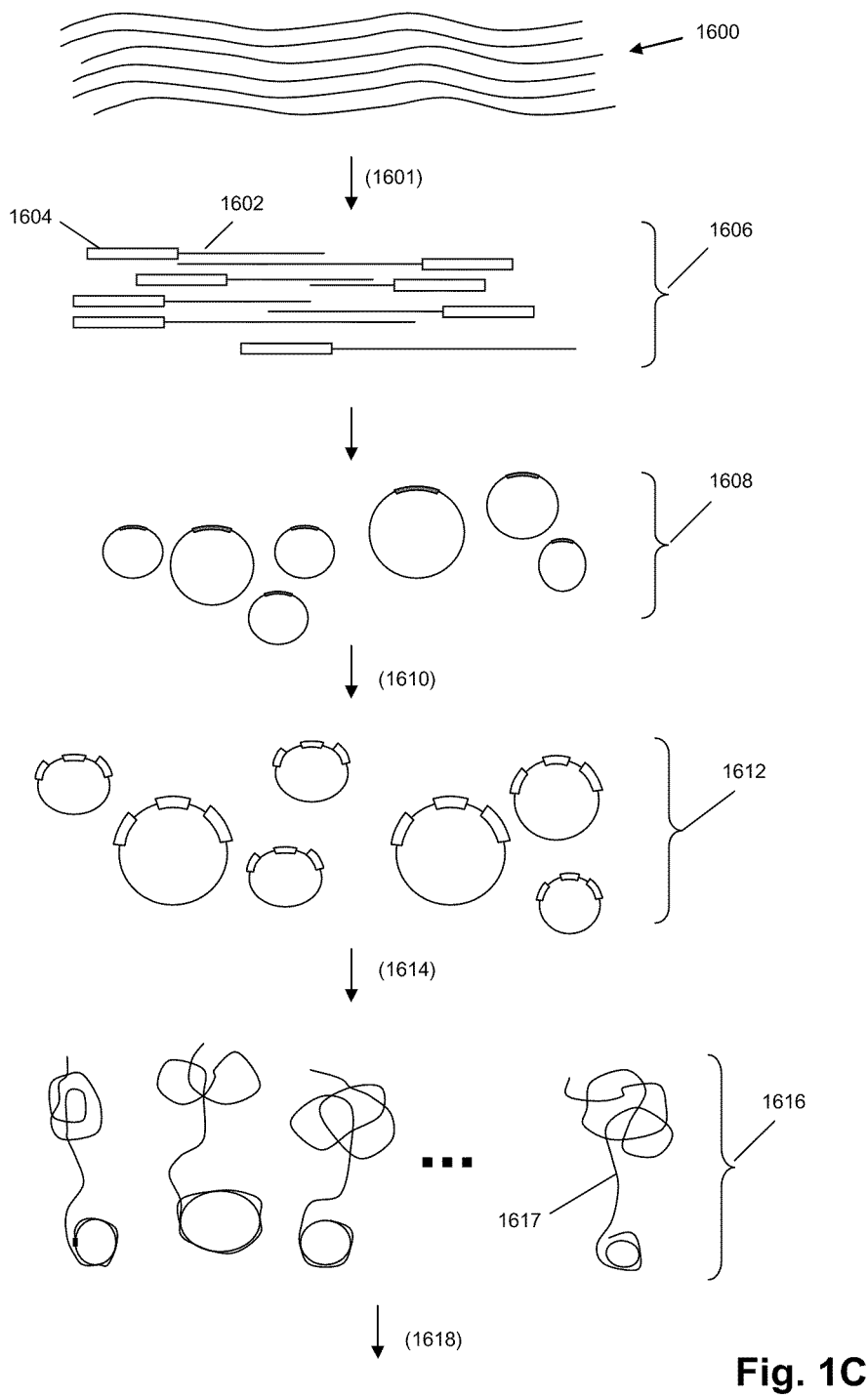
Figure 1D:
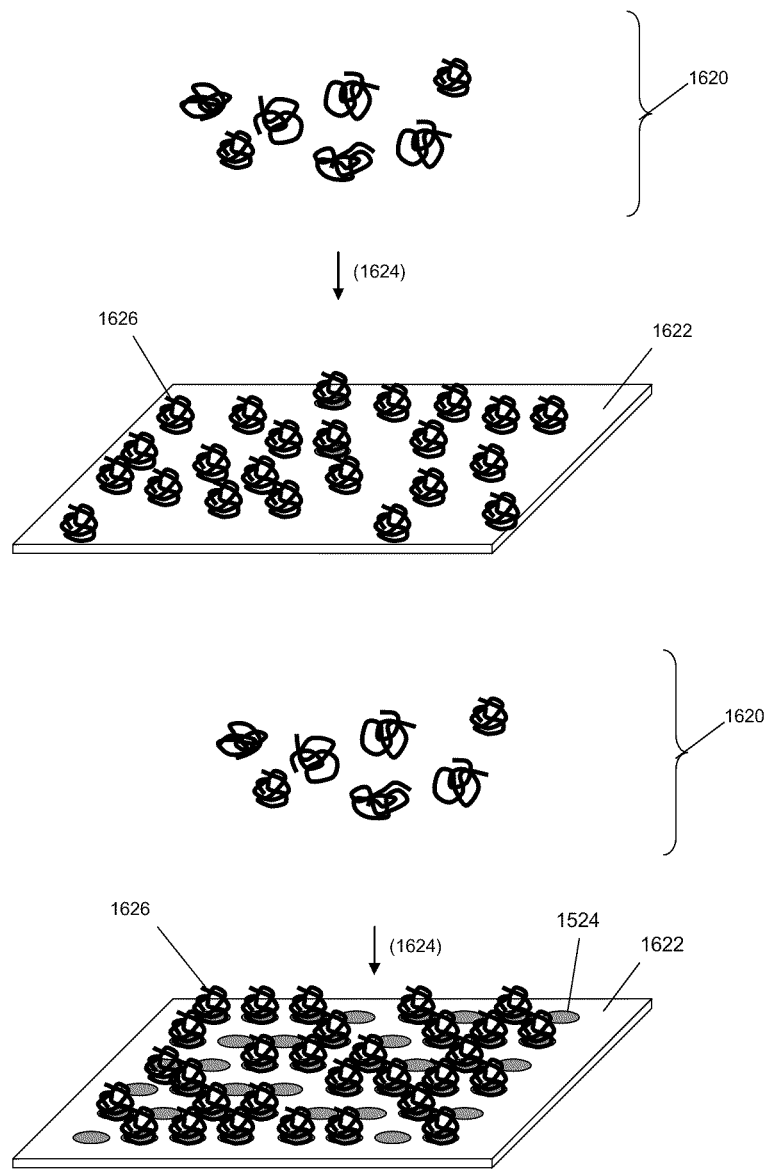
Figure 1E:
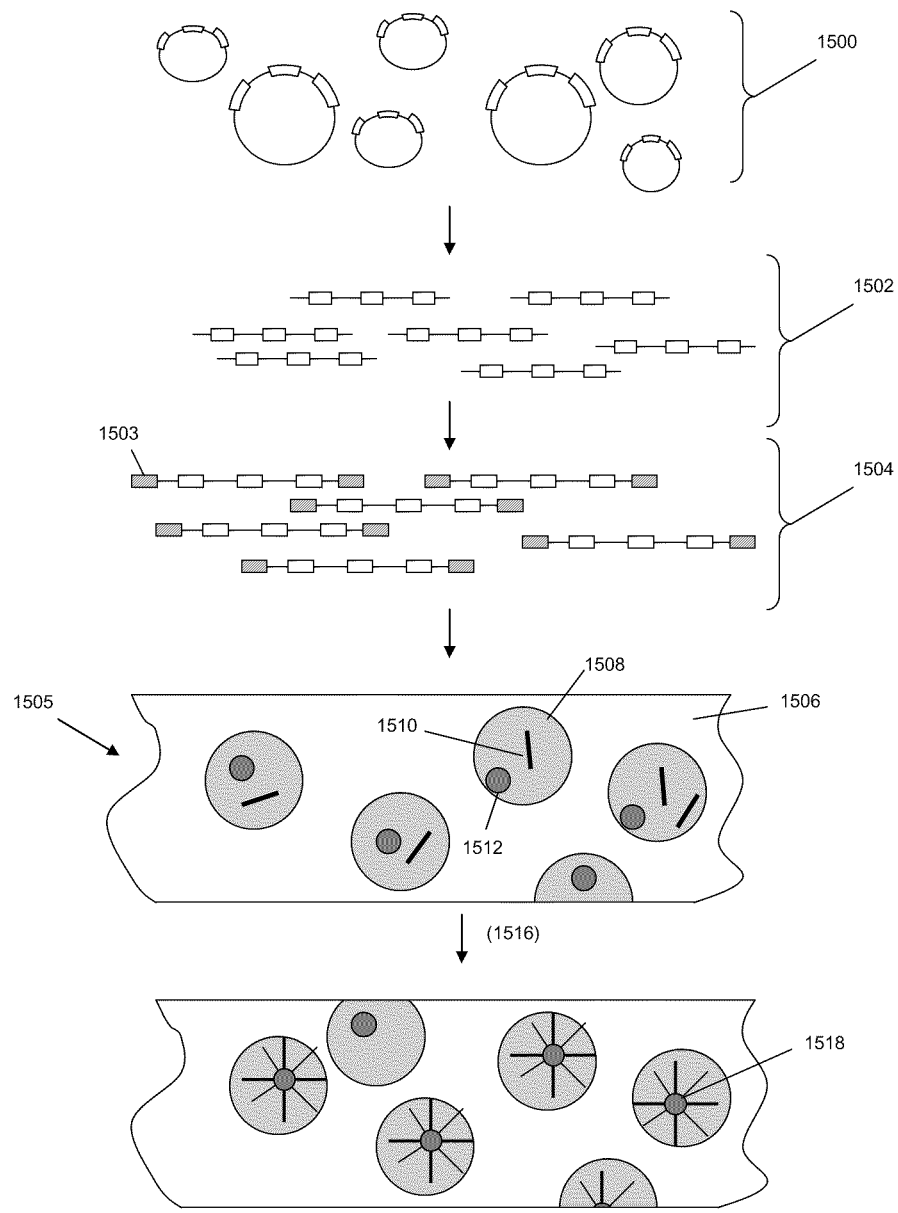

In another aspect, the invention provides methods and compositions for generating concatemers of a plurality of target polynucleotides containing interspersed adaptors. In one embodiment, such concatemers may be generated by RCR, as illustrated in FIGS. 1C-1D.

Rolling circle replication is a preferred method of creating concatemers of the invention. The RCR process has been shown to generate multiple continuous copies of the M13 genome. (Blanco, et al., (1989) *J Biol Chem* 264:8935-8940). In this system, the desired DNA fragment is "cloned" into a DNA adaptor and replicated by linear concatemerization. The target DNA is immediately in a form suitable for hybridization and enzymatic methodologies without the need to passage through bacteria.

The RCR process relies upon the desired target molecule first being formed into a circular substrate. This linear amplification uses the original DNA molecule, not copies of a copy, thus ensuring fidelity of sequence. As a circular entity, the molecule acts as an endless template for a strand displacing polymerase that extends a primer complementary to a portion of the circle. The continuous strand extension creates long, single-stranded DNA consisting of hundreds of concatemers comprising multiple copies of sequences complementary to the circle.

Methods for Creating Arrays

Figure 1F:
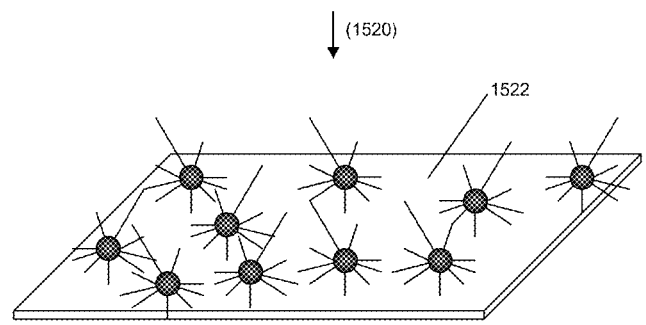
Figure 1G:
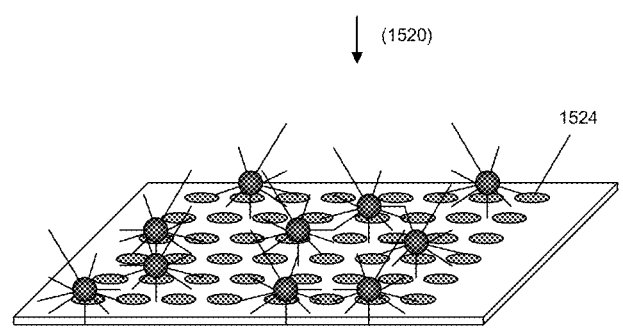

In one embodiment, emulsion PCR is used to generate amplicons for disposal onto an array. As illustrated in FIG. (1B) after breaking emulsion (1505), beads containing clones of the adaptored sequences may be arrayed (1520) on a solid surface (1522) for sequence analysis. Such array of beads may be random, as illustrated in FIG. 1F, where the locations of the beads are not determined prior to arraying, or the array may be in accordance with a predetermined pattern of binding sites (1524), even though the distribution of beads on such sites is randomly determined. Both of such distributions are referred to herein as "random arrays."

To achieve compact, dense bundles of the DNA in the form of sub-micron spots, a region of the amplified molecule for hybridization to a capture probe attached to the glass surface can be utilized. Hundreds of capture probe molecules (spaced about 10 nm apart) can keep hundreds of concatenated copies of a target molecule tightly bound to a glass surface area of less than 500 nm in diameter. In one embodiment, glass activation chemistry is applied that creates a monolayer of isothiocyanate reactive groups for attaching amine modified capture oligonucleotides.

Generally, densities of single molecules are selected that permit at least twenty percent, or at least thirty percent, or at least forty percent, or at least a majority of the molecules to be resolved individually by the signal generation and detection systems used. In one aspect, a density is selected that permits at least seventy percent of the single molecules to be individually resolved. In one aspect, whenever scanning electron microscopy is employed, for example, with molecule-specific probes having gold nanoparticle labels, e.g. Nie et al (2006), Anal. Chem., 78: 1528-1534, which is incorporated by reference, a density is selected such that at least a majority of single molecules have a nearest neighbor distance of 50 nm or greater; and in another aspect, such density is selected to ensure that at least seventy percent of single molecules have a nearest neighbor distance of 100 nm or greater. In another aspect, whenever optical microscopy is employed, for example with molecule-specific probes having fluorescent labels, a density is selected such that at least a majority of single molecules have a nearest neighbor distance of 200 nm or greater; and in another aspect, such density is selected to ensure that at least seventy percent of single molecules have a nearest neighbor distance of 200 nm or greater. In still another aspect, whenever optical microscopy is employed, for example with molecule-specific probes having fluorescent labels, a density is selected such that at least a majority of single molecules have a nearest neighbor distance of 300 nm or greater; and in another aspect, such density is selected to ensure that at least seventy percent of single molecules have a nearest neighbor distance of 300 nm or greater, or 400 nm or greater, or 500 nm or greater, or 600 nm or greater, or 700 nm or greater, or 800 nm or greater. In still another embodiment, whenever optical microscopy is used, a density is selected such that at least a majority of single molecules have a nearest neighbor distance of at least twice the minimal feature resolution power of the microscope. In another aspect, polymer molecules of the invention are disposed on a surface so that the density of separately detectable polymer molecules is at least 1000 per $\mu m^2$, or at least 10,000 per $\mu m^2$, or at least 100,000 per $\mu m^2$.

In another aspect of the invention, the requirement of selecting densities of randomly disposed single molecules to ensure desired nearest neighbor distances is obviated by providing on a surface discrete spaced apart regions that are substantially the sole sites for attaching single molecules. That is, in such embodiments the regions on the surface between the discrete spaced apart regions, referred to herein as "inter-regional areas," are inert in the sense that concatemers, or other macromolecular structures, do not bind to such regions. In some embodiments, such inter-regional areas may be treated with blocking agents, e.g. DNAs unrelated to concatemer DNA, other polymers, and the like. Generally, the area of discrete spaced apart regions is selected, along with attachment chemistries, macromolecular structures employed, and the like, to correspond to the size of single molecules of the invention so that when single molecules are applied to surface substantially every region is occupied by no more than one single molecule. The likelihood of having only one single molecule per discrete spaced apart region may be increased by selecting a density of reactive functionalities or capture oligonucleotides that results in fewer such moieties than their respective complements on single molecules. Thus, a single molecule will "occupy" all linkages to the surface at a particular discrete spaced apart region, thereby reducing the chance that a second single molecule will also bind to the same region. In particular, in one embodiment, substantially all the capture oligonucleotides in a discrete spaced apart region hybridize to adaptor oligonucleotides a single macromolecular structure. In one aspect, a discrete spaced apart region contains a number of reactive functionalities or capture oligonucleotides that is from about ten percent to about fifty percent of the number of complementary functionalities or adaptor oligonucleotides of a single molecule. The length and sequence(s) of capture oligonucleotides may vary widely, and may be selected in accordance with well known principles, e.g. Wetmur, Critical Reviews in Biochemistry and Molecular Biology, 26: 227-259 (1991); Britten and Davidson, chapter 1 in Hames et al, editors, Nucleic Acid Hybridization: A Practical Approach (IRL Press, Oxford, 1985). In one aspect, the lengths of capture oligonucleotides are in a range of from 6 to 30 nucleotides, and in another aspect, within a range of from 8 to 30 nucleotides, or from 10 to 24 nucleotides. Lengths and sequences of capture oligonucleotides are selected (i) to provide effective binding of macromolecular structures to a surface, so that losses of macromolecular structures are minimized during steps of analytical operations, such as washing, etc., and (ii) to avoid interference with analytical operations on analyte molecules, particularly when analyte molecules are DNA fragments in a concatemer. In regard to (i), in one aspect, sequences and lengths are selected to provide duplexes between capture oligonucleotides and their complements that are sufficiently stable so that they do not dissociate in a stringent wash. In regard to (ii), if DNA fragments are from a particular species of organism, then databases, when available, may be used to screen potential capture sequences that may form spurious or undesired hybrids with DNA fragments. Other factors in selecting sequences for capture oligonucleotides are similar to those considered in selecting primers, hybridization probes, oligonucleotide tags, and the like, for which there is ample guidance, as evidenced by the references cited below in the Definitions section.

In one aspect, the area of discrete spaced apart regions is less than 1 $\mu m^2$; and in another aspect, the area of discrete spaced apart regions is in the range of from 0.04 $\mu m^2$ to 1 $\mu m^2$; and in still another aspect, the area of discrete spaced apart regions is in the range of from 0.2 $\mu m^2$ to 1 $\mu m^2$. In another aspect, when discrete spaced apart regions are approximately circular or square in shape so that their sizes can be indicated by a single linear dimension, the size of such regions are in the range of from 125 nm to 250 nm, or in the range of from 200 nm to 500 nm. In one aspect, center-to-center distances of nearest neighbors of such regions are in the range of from 0.25 µm to 20 µm; and in another aspect, such distances are in the range of from 1 µm to 10 µm, or in the range from 50 to 1000 nm. Preferably, spaced apart regions for immobilizing concatemers are arranged in a rectilinear or hexagonal pattern.

In one embodiment, spacer DNBs are used to prepare a surface for attachment of test DNBs. The surface is first covered by the capture oligonucleotide complementary to the binding site present on two types of synthetic DNBs; one is a capture DNB, the other is a spacer DNB. The spacer DNBs do not have DNA segments complementary to the adaptor used in preparation of test DNBs and they are used in about 5-50, preferably 10× excess to capture DNBs. The surface with capture oligonucleotide is "saturated" with a mix of synthetic DNBs (prepared by chain ligation or by RCR) in which the spacer DNBs are used in about 10-fold (or 5 to 50-fold) excess to capture DNBs. Because of the ~10:1 ratio between spacer and capture DNBs, the capture DNBs are mostly individual islands in a sea of spacer DNBs. The 10:1 ratio provides that two capture DNBs are on average separated by two spacer DNBs. If DNBs are about 200 nm in diameter, then two capture DNBs are at about 600 nm center-to-center spacing. This surface is then used to attach test DNBs or other molecular structures that have a binding site complementary to a region of the capture DNBs but not present on the spacer DNBs.

Capture DNBs may be prepared to have fewer copies than the number of binding sites in test DNBs to assure single test DNB attachment per capture DNB spot. Because the test DNA can bind only to capture DNBs, an array of test DNBs may be prepared that have high site occupancy without congregation. Due to random attachment, some areas on the surface may not have any DNBs attached, but these areas with free capture oligonucleotide may not be able to bind test DNBs since they are designed not to have binding sites for the capture oligonucleotide. Arrays of the invention may or may not be arranged in a grid pattern.

In one aspect, a high density array of capture oligonucleotide spots of sub micron size is prepared using a printing head or imprint-master prepared from a bundle, or bundle of bundles, of about 10,000 to 100 million optical fibers with a core and cladding material. By proper pulling and fusing fibers, a unique material may be produced that has about 50-1000 nm cores separated by a similar or 2-5 fold smaller or larger size cladding material. In one embodiment, differential etching (dissolving) of cladding material provides a nanoprinting head having a very large number of nano-sized posts. This printing head may be used for depositing oligonucleotides or other biological (proteins, oligopeptides, DNA, aptamers) or chemical compounds such as silane with various active groups.

In one embodiment the glass fiber tool may be used as a patterned support to deposit oligonucleotides or other biological or chemical compounds. In this case only posts created by etching may be contacted with material to be deposited. In another embodiment, a flat cut of the fused fiber bundle may be used to guide light through cores and allow light-induced chemistry to occur only at the tip surface of the cores, thus eliminating the need for etching. In both embodiments, the same support may then be used as a light guiding/collection device for imaging fluorescence labels used to tag oligonucleotides or other reactants. This device provides a large field of view with a large numerical aperture (potentially >1).

Stamping or printing tools that perform active material or oligonucleotide deposition may be used to print 2 to 100 different oligonucleotides in an interleaved pattern. This type of oligonucleotide array may be used for attaching 2 to 100 different DNA populations, such as populations derived from different source DNA. They also may be used for parallel reading from sub-light resolution spots by using DNA specific anchors or tags. Information can be accessed by DNA specific tags, e.g. 16 specific anchors for 16 DNAs and read 2 bases by a combination of 5-6 colors and using 16 ligation cycles or one ligation cycle and 16 decoding cycles.

In embodiments of the invention, photolithography, electron beam lithography, nano imprint lithography, and nano printing may be used to generate such patterns on a wide variety of surfaces, e.g. Pirrung et al, U.S. Pat. No. 5,143,854; Fodor et al, U.S. Pat. No. 5,774,305; Guo, (2004) Journal of Physics D: Applied Physics, 37: R123-141; which are incorporated herein by reference. These techniques can be used to generate patterns of features on the order of $1/10^{th}$ of a micron and have been developed for use in the semiconductor industry. In a preferred embodiment, a single "masking" operation is performed on the DNA array substrate, as opposed to the 20 to 30 masking operations typically needed to create even a simple semiconductor. Using a single masking operation eliminates the need for the accurate alignment of many masks to the same substrate. There is also no need for doping of materials. Minor defects in the pattern may have little to no effect on the usability of the array, thus allowing production yields to approach 100%.

Figure 4:
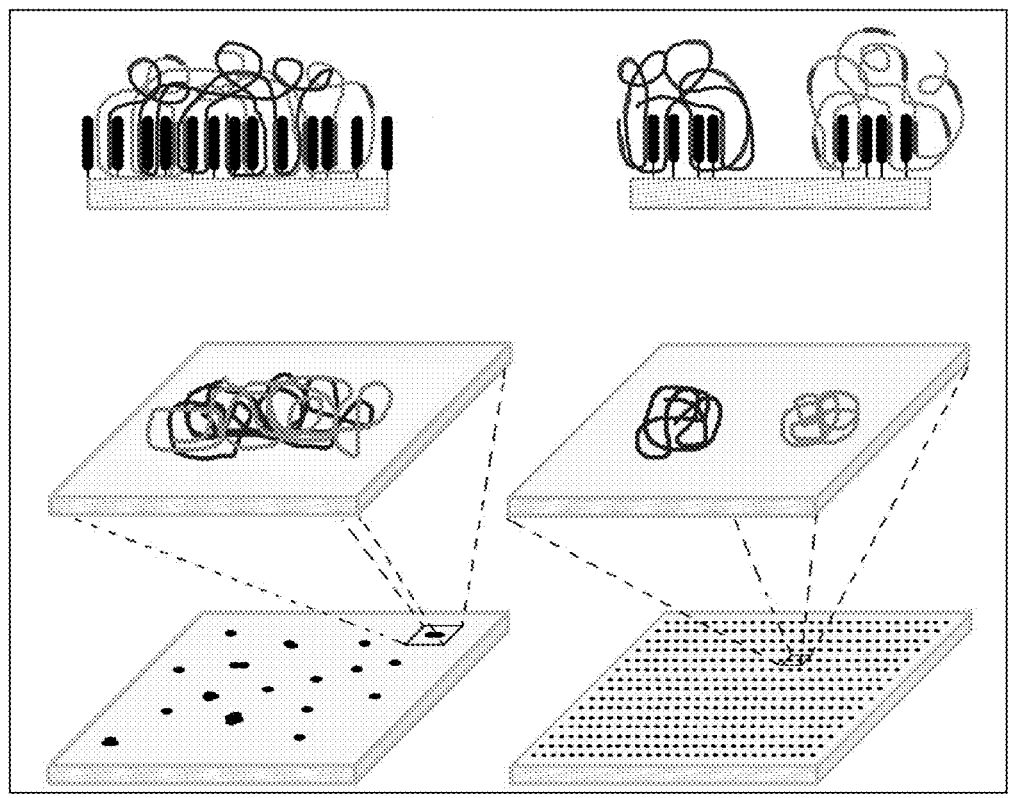
FIG. 4 provides a comparison of structured and standard random DNA arrays made by attaching RCR products.

In one embodiment, high density structured random DNA array chips have capture oligonucleotides concentrated in small, segregated capture cells aligned into a rectangular grid formation (FIG. 4). Preferably, each capture cell or binding site is surrounded by an inert surface and may have a sufficient but limited number of capture molecules (100-400). Each capture molecule may bind one copy of the matching adaptor sequence on the RCR produced DNA concatemer. Since each concatemer contains over 1000 copies of the adaptor sequence, it is able to quickly saturate the binding site upon contact and prevent other concatemers from binding, resulting in exclusive attachment of one RCR product per binding site or spot. By providing enough RCR products almost every spot on the array may contain one and only one unique DNA target.

RCR "molecular cloning" allows the application of the saturation/exclusion (single occupancy) principle in making random arrays. The exclusion process is not feasible in making single molecule arrays if an in situ amplification is alternatively applied. RCR concatemers provide an optimal size to form small non-mixed DNA spots. Each concatemer of about 100 kb is expected to occupy a space of about $0.1 \times 0.1 \times 0.1$ μm, thus allowing RCR products to fit into 100 nm capture cells. One advantage of RCR products is that the single stranded DNA is ready for hybridization and is very flexible for forming a randomly coiled ball of DNA. The 1000 copies of DNA target produced by RCR provide much higher specificity than is possible with analysis of a single molecule.

There are methods known in the art for generating a patterned DNA chip. In a preferable embodiment, all spots on the chip have the same capture oligonucleotides and a 0.2-0.3 micron spot size at 0.5 micron pitch. Nano-printing approaches may be used for producing such patterns, as they do not require development of new oligonucleotide attachment chemistry.

Nano-imprint technologies rely on classic photolithographic techniques to produce a master mold. The master mold is then replicated using polymers such as PMMA or PDMS. These polymers, upon curing, form a negative mold of the master. The mold is then used to "print" patterns of material on a substrate. The nano-imprint technique can be used to create protein features on glass, silicon, and gold surfaces. In an exemplary embodiment, a master mold is used to generate many stamping devices and each stamping device can generate many prints of chemicals (such as oligonucleotide solution, oligonucleotide binding or glass activation chemicals). Advanced nano-printing techniques can produce features as small as 10 nm, thus, features appropriate for fluorescent detection that are >200 nm in size, including features 300-500 nm at 1000 microns center to center, can be produced routinely.

Various chemical modifications can be used to alter surface properties, increasing the compatibility of the master mold with a wide range of materials, thus allowing the use of a small feature, low-density mold to create high density arrays. In one embodiment, a mold with a 4 um feature pitch can be used to create a one um feature pitch on the substrate by printing the same substrate 16 times in a 4 by 4 grid.

In one aspect, a method of creating DNA arrays involves the use of a thin layer of photo-resist to protect portions of the substrate surface during a functionalization process. The patterned photo-resist is removed after functionalization, leaving an array of activated areas. The second approach involves attaching a monolayer of modified oligonucleotides to the substrate. The oligonucleotides are modified with a photocleavable protecting group. These protecting groups can be removed by exposure to an illumination source, allowing patterned ligation of a capture oligonucleotide for attachment of DNBs by hybridization.

In another embodiment, a commercially available, optically flat, quartz wafer is spin coated with a 100-500 nm thick layer of photo-resist. The photo-resist is baked on to the quartz wafer, and an image of a reticle with a pattern of spots to be activated is projected onto the surface of the photo-resist, using a machine commonly called a stepper. After exposure, the photo-resist is developed, removing the areas of the projected pattern which were exposed to the UV source. This is accomplished by plasma etching, a dry developing technique capable of producing very fine detail. The wafer is then baked to strengthen the remaining photo-resist.

After baking, the quartz wafer is ready for functionalization. The wafer is then subjected to vapor-deposition of 3-aminopropyldimethylethoxysilane, the same monomer used in the current functionalization process. The density of the amino functionalized monomer can be tightly controlled by varying the concentration of the monomer and the time of exposure of the substrate. Only areas of quartz exposed by the plasma etching process may react with and capture the monomer. The wafer is then baked again to cure the monolayer of amino-functionalized monomer to the exposed quartz. After baking, the remaining photo-resist may be removed using acetone. Because of the difference in attachment chemistry between the resist and silane, aminosilane-functionalized areas on the substrate may remain intact through the acetone rinse. These areas can be further functionalized by reacting them with p-phenylenediisothiocyanate in a solution of pyridine and N—N-DiMethlyFormamide. The substrate may then be compatible with amine-modified oligonucleotides. Alternatively, oligonucleotides can be prepared with a 5'-carboxy-modifier-c10 (Glen Research: http://www.glenres.com/ProductFiles/10-1935.html). This technique allows the oligonucleotide to be attached directly to the amine modified support, thereby avoiding additional functionalization steps.

In another embodiment, a nano-imprint lithography (NIL) process is used which starts with the production of a master imprint tool. This tool is produced using high-resolution e-beam lithography, and can be used to create a large number of imprints, depending on the NIL polymer utilized. For DNA array production, the quartz substrate would be spin coated with a layer of resist, this layer commonly called the transfer layer. A second type of resist is then applied over the transfer layer, this layer is commonly called the imprint layer. The master imprint tool then makes an impression on the imprint layer. The overall thickness of the imprint layer is then reduced by plasma etching until the low area's of the imprint reach the transfer layer. Because the transfer layer is harder to remove than the imprint layer, it remains largely untouched. The imprint and transfer layers are then hardened by heating. The substrate is then put back into the plasma etcher until the low areas of the imprint reach the quartz. The substrate is then derivatized by vapor deposition as described in method 1a.

In another embodiment, a nano-printing method is used. Such a process uses photo, imprint, or e-beam lithography to create a master mold. There are many variations on the techniques used to manufacture the nano-imprint tools. In one exemplary method, the master mold is created as a negative image of the features required on the print head. The print heads are usually made of a soft, flexible polymer such as polydimethylsiloxane (PDMS). This material, or layers of materials having different properties, are spin coated onto a quartz substrate. The mold is then used to emboss the features onto the top layer of resist material under controlled temperature and pressure conditions. The print head is then subjected to a plasma based etching process to improve the aspect ratio of the print head, and eliminate distortion of the print head due to relaxation over time of the embossed material. The print head is used to deposit a pattern of amine modified oligonucleotides onto a homogenously derivatized surface. These oligo-nucleotides serve as capture probes for the DNB's. One advantage to nano-printing is the ability to print interleaved patterns of different capture probes onto the random array support. This can be accomplished by successive printing with multiple print heads, each head having a differing pattern, and all patterns fitting together to form the final structured support pattern. Such methods allow for positional encoding of DNA elements within the random array. For example, control DNBs containing a specific anchor sequence can be bound at regular intervals throughout a random array.

Electron beam lithography can also be used to create the substrate. This process is very similar to photolithography, except the pattern is drawn directly on a special resist material using an electron beam gun. The benefit of this process is that the feature size can be much smaller and more precise than with UV photolithographic methods. A potential drawback is the amount of time required to create the pattern is on the order of hours per substrate, as opposed to a couple of seconds using photolithographic methods or less than a minute for NIL.

In one embodiment, the arrays are produced using photo-cleavable modifiers, also referred to as protecting groups. In such a method, capture cells can be created by using commercially available photo-cleavable modifiers to oligonucleotides, such as the PC Linker Phosphoramidite, available from Glen Research. An oligonucleotide with a 5 prime photo-cleavable protection group, in this case DMTO, is attached to a fully functionalized piece of quartz at the 3' terminus. The exposed areas lose their protecting group, leaving a 5' phosphate. Using oligonucleotide ligation, a capture oligonucleotide complementary to the adaptor region of RCR products is ligated to exposed phosphate groups if a template oligonucleotide is provided as depicted below:

```
(oligonucleotide on the surface)
|------cttactgtgc (SEQ. ID No. 10)-P OH-ggactaccgtttagg..cccgtgg (SEQ. ID NO. 11)
(capture oligonucleotide)

gaatgacacg (SEQ. ID NO. 12).......cctgatggca (SEQ. ID NO. 13)
(single template oligonucleotide;)
```

After ligation of the capture oligonucleotide to the deprotected surface oligonucleotides, the entire substrate can be exposed to a UV source to remove the remaining protecting groups. The free phosphate groups may be blocked by ligating hairpin like oligonucleotides to prevent ligation of labeled probes used in the sequencing process to the support oligonucleotide.

The photo-resist material used in fabrication methods is generally quite hydrophobic, and the patterns made in that material consist of very small holes. It is possible that the exposed surface of the quartz may not come into contact with aqueous solutions of the amino functionalized monomer due to the hydrophobic effect of the photo-resist. To avoid this problem, one embodiment of the invention is to use ultra-sound to force the liquid past the small openings in the mask. It is also possible to put a small amount of surfactant, acetone, or other additive to the solution to break the surface tension of the water. The use of solvents in this manner might swell the mask material slightly, but it would not dissolve it. In the event that the resist material is incompatible with the amino-functionalized surface during the resist removal process, for instance it might react with and destroy the amine, it is possible to perform a mechanical peel of the resist material using a strong acrylic based adhesive on a polymer sheet.

After each batch of DNA array substrates is made, it may be important to determine if the batch is up to specification. Specifications may be determined during the mask design and biochemistry optimization phase. Quality control of each batch of substrates can be performed by attaching FITC or a amine-modified oligonucleotide with any fluorescent label to the reactive surface and observing the intensity and pattern of the fluorescence on the substrate surface. The overall intensity of the active regions may be proportional to the density of reactive sites in the capture cells. The current microscopy system has a 100×, 1.4NA lens that has a theoretical resolving power of about 180 nm. The sensitivity of the current image acquisition system is about 3 dye molecules per pixel, with each pixel imaging a 60×60 nm area of the substrate. It is expected to be able to attach between 10-50 capture oligonucleotides per 60 nm square area. This allows directly measuring, with high accuracy, the attachment efficiency and grid properties of the substrate. Each capture cell may be imaged by roughly 10 pixels.

Using the QC data, it is possible to determine which substrate preparation steps need improvement. Intensity variation between capture cells, at this point in the process, would point to uneven reaction conditions during the functionalization process or non-uniform development of the photo-resist layer. If there is bridging between cells, it would suggest that the photo-resist material delaminated from the surface of the quartz, or that something went wrong during the exposure process. Problems with signal intensity would point to poor control of the functionalization step. Additional metrics may necessarily be developed as the process matures.

Replica Arrays

In one aspect of the invention, complementary polynucleotides synthesized on a master array are transferred to a replica array. To achieve such a transfer, two surfaces may be contacted in the presence of heating to denature dsDNA and free newly made DNA strands. In another embodiment, the transfer is achieved by applying an electric field to discriminatively transfer only the replicated DNA that has about 5-50 times more charge than primers. In a further embodiment, after hybridizing the transferred strand a reverse field is combined with a reduction in temperature to move primers back to the master array. In an embodiment in which the transfer is achieved by applying an electric field, porous glass is preferably used to allow the application of the electric field.

In one embodiment, a capture oligonucleotide is designed to correspond to the end of an amplicon opposite to the priming site to assure exclusive retention of the full length copies. Having a pattern of nine or more different capture oligonucleotides minimizes the chance of "cross talk" during DNA transfer from the master array. In one embodiment, the transfer is achieved without further amplification of DNA on the replica array; multiple transfers to the same replica may also be used to generate a stronger signal. In another embodiment, multiple replicas may be generated by partial transfer from the master array, with DNA amplification performed in each replica array.

In an exemplary embodiment, the substrate for the replica array contains primers for initiating DNA synthesis using template DNA attached on the first array. After contacting surfaces of the master array and support of the "to be formed" replica array in the presence of DNA polymerase, dNTPs and suitable buffer at optimum temperature, primer molecules hybridize to the template DNA on the master array and become extended by the polymerase. A stopping agent such as dsDNA may be used to stop DNA at the end of one copy. By increasing temperature, or by using other DNA denaturing agents, DNA strands may separate and the replica array can be separated form the first array. To prevent removal of original DNA from the master array, the original DNA may be directly (or indirectly via capture oligonucleotide) covalently attached to the master array support.

Any incomplete DNA that is attached to the replica array may be specifically removed after completion of the replication reaction using various methods known in the art, such as through protective ligation of the completed molecules that have specific ends—the incomplete molecules can then be removed without losing the completed molecules.

In one embodiment, primers cover the entire substrate surface for array preparation. A primer density of 10,000 per micron square provides a local concentration in one micron, between two supports, of similar or about 10 times higher concentration than used in PCR. Primers may have very long attachment linkers to be able to reach to the DNA template on the first array's support. In this process there is no possibility for DNA diffusion and replica DNA spots may be only slightly larger than original spots. A very flat surface may be used to assure close proximity of two surfaces. In one embodiment, DNBs provide enough DNA loops of about 300-500 nm and when combined with 100 nm primer linkers, allowing tolerance of surface imperfections.

Replica arrays may be used to produce additional replicas. Second generation replicas would have the same DNA strand as the original array.

Replica arrays may be used for parallel analysis of the same set of DNA fragments such as hybridization with a large number of probes or probe pools. In another embodiment, self-assembled DNA master chips containing genomic fragments may be replicated to generate many detection arrays that do not need to be decoded because they match the same master chip that was already decoded. Thus, replication of arrays allows us preparation of self-assembled DNA arrays with minimal decoding costs, because one master and its replicas may be used to produce thousands of final arrays.

Structure of Capture Oligos

In one embodiment, surface (FIGS. 1C & D—1622) may have attached capture oligonucleotides that form complexes, e.g. double stranded duplexes, with a segment of an adaptor oligonucleotide in the concatemers, such as an anchor binding site or other elements. In other embodiments, capture oligonucleotides may comprise oligonucleotide clamps, or like structures, that form triplexes with adaptor oligonucleotides, e.g. Gryaznov et al, U.S. Pat. No. 5,473,060. In another embodiment, surface (1622) may have reactive functionalities that react with complementary functionalities on the concatemers to form a covalent linkage, e.g. by way of the same techniques used to attach cDNAs to microarrays, e.g. Smirnov et al (2004), Genes, Chromosomes & Cancer, 40: 72-77; Beaucage (2001), Current Medicinal Chemistry, 8: 1213-1244, which are incorporated herein by reference.

In one aspect, when enzymatic processing is not required, capture oligonucleotides may comprise non-natural nucleosidic units and/or linkages that confer favorable properties, such as increased duplex stability; such compounds include, but not limited to, peptide nucleic acids (PNAs), locked nucleic acids (LNA), oligonucleotide N3'→P5' phosphoramidates, oligo-2'-O-alkylribonucleotides, and the like.

Structure of Random Arrays

In one aspect, concatemers (1620—FIGS. 1C & D) may be fixed to surface (1622) by any of a variety of techniques, including covalent attachment and non-covalent attachment. In one embodiment, surface (1622) may have attached capture oligonucleotides that form complexes, e.g. double stranded duplexes, with a segment of an adaptor oligonucleotide in the concatemers, such as an anchor binding site or other elements. In other embodiments, capture oligonucleotides may comprise oligonucleotide clamps, or like structures, that form triplexes with adaptor oligonucleotides, e.g. Gryaznov et al, U.S. Pat. No. 5,473,060. In another embodiment, surface (1622) may have reactive functionalities that react with complementary functionalities on the concatemers to form a covalent linkage, e.g. by way of the same techniques used to attach cDNAs to microarrays, e.g. Smirnov et al (2004), Genes, Chromosomes & Cancer, 40: 72-77; Beaucage (2001), Current Medicinal Chemistry, 8: 1213-1244, which are incorporated herein by reference. Long DNA molecules, e.g. several hundred nucleotides or larger, may also be efficiently attached to hydrophobic surfaces, such as a clean glass surface that has a low concentration of various reactive functionalities, such as —OH groups.

In one embodiment, complete genome sequencing uses an array comprising a 50 to 200× genome coverage of the analyzed polynucleotide fragments. For example 6 billion DNBs with an average fragment length of 100 bases would contain 600 billion bases representing 100× genome coverage. In one embodiment, the array comprises 6 billion DNBs composed of 300-600 base long DNA fragments. The DNBs may be bound to the array substrate in a square pack arrangement at a pitch of one micron and the array substrate may be split across 16 segments. In a further embodiment, each segment contains 24 unit sub arrays with each unit sub array containing 16 million bound DNBs over a 2×2 square millimeter area.

A sequencing assay which uses 8 segments and DNB's 250 bases long may require 350 probe pools for sequencing. Various tradeoffs between fragment length, DNB count, pool sets, and overlap can be made to optimize sequence quality versus imaging time. For example, the same random array segmented into 16 segments may require 225 probe pools for sequencing. This would require fewer probe pool cycles, reducing imaging time. Additionally, DNBs can be composed of 500 base long fragments, requiring 3 billion DNB's to be assayed against 350 probe pools using 16 segments tested in 16 reaction chambers. This format would produce a random array with 256× genome coverage, thus reducing the unit array size to two square millimeters. In one embodiment, each probe pool is combinatorially labeled using 2 of 6 fluorophores producing up to 21 possible fluorescent label combinations. This labeling schema allows assaying against many probes simultaneously, reducing hybridization time by an order of magnitude.

A wide variety of supports may be used for arrays of the invention. In one aspect, supports are rigid solids that have a surface, preferably a substantially planar surface so that single molecules to be interrogated are in the same plane. The latter feature permits efficient signal collection by detection optics.

In another aspect, solid supports of the invention are nonporous, particularly when random arrays of single molecules are analyzed by hybridization reactions requiring small volumes. Suitable solid support materials include materials such as glass, polyacrylamide-coated glass, ceramics, silica, silicon, quartz, various plastics, and the like.

In one aspect, the area of a planar surface may be in the range of from 0.5 to 4 cm$^2$. In one aspect, the solid support is glass or quartz, such as a microscope slide, having a surface that is uniformly silanized. This may be accomplished using conventional protocols, e.g. acid treatment followed by immersion in a solution of 3-glycidoxypropyl trimethoxysilane, N,N-diisopropylethylamine, and anhydrous xylene (8:1:24 v/v) at 80° C., which forms an epoxysilanized surface. e.g. Beattie et a (1995), Molecular Biotechnology, 4: 213. Such a surface is readily treated to permit end-attachment of capture oligonucleotides, e.g. by providing capture oligonucleotides with a 3' or 5' triethylene glycol phosphoryl spacer prior to application to the surface. Many other protocols may be used for adding reactive functionalities to glass and other surfaces, as evidenced by the disclosure in Beaucage (cited above).

Arrays of DNA targets with interspersed adaptor(s) are not limited to single molecule or concatemers, and can include arrays of in situ amplified DNA spots or arrays of particles, each comprising multiple copies of a target nucleic acid (for example beads used in emulsion-PCR). Furthermore, methods as described herein which utilize multiple anchors or primers that can be differentially removed or otherwise discriminated are not limited to interspersed adaptors, i.e. they can be accomplished on samples with two "standard", i.e. end-ligated adaptors having a total of 4 anchor sites.

Structure of Probes

The term "probes" is used in a broad sense of oligonucleotides used in direct hybridization, or as in ligation of two probes, or as in probe with an anchor, or as in a probe with an anchor probe. Probes may have only a few specific bases and many degenerate bases: for example BNNNNNNN or BBNNNNNN or NNBBNNNN. Anchor probes may be designed as U5-10B1-4 to read 1-4 bases adjacent to an adaptor sequence complementary to an anchor U5-10 sequence.

The oligonucleotide probes of the invention can be labeled in a variety of ways, including the direct or indirect attachment of radioactive moieties, fluorescent moieties, calorimetric moieties, chemiluminescent moieties, and the like. Many comprehensive reviews of methodologies for labeling DNA and constructing DNA adaptors provide guidance applicable to constructing oligonucleotide probes of the present invention. Such reviews include Kricka, Ann. Clin. Biochem., 39: 114-129 (2002); Schaferling et al, Anal. Bioanal. Chem., (Apr. 12, 2006); Matthews et al, *Anal. Biochem.*, Vol 169, pgs. 1-25 (1988); Haugland, Handbook of Fluorescent Probes and Research Chemicals, Tenth Edition (Invitrogen/Molecular Probes, Inc., Eugene, 2006); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26: 227-259 (1991); Hermanson, Bioconjugate Techniques (Academic Press, New York, 1996); and the like. Many more particular methodologies applicable to the invention are disclosed in the following sample of references: Fung et al, U.S. Pat. No. 4,757,141; Hobbs, Jr., et al U.S. Pat. No. 5,151,507; Cruickshank, U.S. Pat. No. 5,091,519; (synthesis of functionalized oligonucleotides for attachment of reporter groups); Jablonski et al, Nucleic Acids Research, 14: 6115-6128 (1986)(enzyme-oligonucleotide conjugates); Ju et al, Nature Medicine, 2: 246-249 (1996); Bawendi et al, U.S. Pat. No. 6,326,144 (derivatized fluorescent nanocrystals); Bruchez et al, U.S. Pat. No. 6,274,323 (derivatized fluorescent nanocrystals); and the like.

In one aspect, one or more fluorescent dyes are used as labels for the oligonucleotide probes, e.g. as disclosed by Menchen et al, U.S. Pat. No. 5,188,934 (4,7-dichlorofluorscein dyes); Begot et al, U.S. Pat. No. 5,366,860 (spectrally resolvable rhodamine dyes); Lee et al, U.S. Pat. No. 5,847,162 (4,7-dichlororhodamine dyes); Khanna et al, U.S. Pat. No. 4,318,846 (ether-substituted fluorescein dyes); Lee et al, U.S. Pat. No. 5,800,996 (energy transfer dyes); Lee et al, U.S. Pat. No. 5,066,580 (xanthene dyes): Mathies et al, U.S. Pat. No. 5,688,648 (energy transfer dyes); and the like. Labeling can also be carried out with quantum dots, as disclosed in the following patents and patent publications, incorporated herein by reference: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. As used herein, the term "fluorescent signal generating moiety" means a signaling means which conveys information through the fluorescent absorption and/or emission properties of one or more molecules. Such fluorescent properties include fluorescence intensity, fluorescence life time, emission spectrum characteristics, energy transfer, and the like.

Commercially available fluorescent nucleotide analogues readily incorporated into the labeling oligonucleotides include, for example, Cy3-dCTP, Cy3-dUTP, Cy5-dCTP, Cy5-dUTP (Amersham Biosciences, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY°R-14-dUTP, BODIPY®TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others). FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes. Biotin, or a derivative thereof, may also be used as a label on a detection oligonucleotide, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP residue may be incorporated into a detection oligonucleotide and subsequently coupled to an N-hydroxy succinimide (NHS) derivitized fluorescent dye, such as those listed supra. In general, any member of a conjugate pair may be incorporated into a detection oligonucleotide provided that a detectably labeled conjugate partner can be bound to permit detection. As used herein, the term antibody refers to an antibody molecule of any class, or any subfragment thereof, such as an Fab. Other suitable labels for detection oligonucleotides may include fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr), or any other suitable label. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM. As described in schemes below, probes may also be indirectly labeled, especially with a hapten that is then bound by a capture agent, e.g. as disclosed in Holtke et al, U.S. Pat. Nos. 5,344,757; 5,702,888; and 5,354,657; Huber et al, U.S. Pat. No. 5,198,537; Miyoshi, U.S. Pat. No. 4,849,336; Misiura and Gait, PCT publication WO 91/17160; and the like. Many different hapten-capture agent pairs are available for use with the invention. Exemplary, haptens include, biotin, des-biotin and other derivatives, dinitrophenol, dansyl, fluorescein, CY5, and other dyes, digoxigenin, and the like. For biotin, a capture agent may be avidin, streptavidin, or antibodies. Antibodies may be used as capture agents for the other haptens (many dye-antibody pairs being commercially available, e.g. Molecular Probes).

In one aspect, pools of probes are provided which preferably have from about 1 to about 3 bases, allowing for an even and optimized signal for different sequences at degenerate positions. In one embodiment, a concentration adjusted mix of 3-mer building blocks is used in the probe synthesis.

Probes may be prepared with nucleic acid tag tails instead of being directly labeled. Tails preferably do not interact with test DNA. These tails may be prepared from natural bases or modified bases such as isoC and isoG that pair only between themselves. If isoC and isoG nucleotides are used, the sequences may be separately synthesized with a 5' amino-linker, which allows conjugation to a 5' carboxy modified linker that is synthesized on to each tagged probe. This allows separately synthesized tag sequences to be combined with known probes while they are still attached to the column. In one embodiment, 21 tagged sequences are used in combination with 1024 known probes.

The tails may be separated from probes by 1-3 or more degenerated bases, abasic sites or other linkers. One approach to minimize interaction of tails and target DNA is to use sequences that are very infrequent in the target DNA. For example, CGCGATATCGCGATAT (SEQ. ID NO. 14) or CGATCGATCGAT (SEQ. ID NO. 15) is expected to be infrequent in mammalian genomes. One option is to use probe with tails pre-hybridized with unlabeled tags that would be denaturated and maybe washed away after ligation and before hybridization with labeled tags. Uracil may be used to generate degradable tails/tags and to remove them before running a new cycle instead of using temperature removal;

In one aspect high-plex multiplex ligation assays of probes are used which are not labeled with fluorescent dyes, thus reducing background and assay costs. For example for 8 colors 4×8=32 different encoding tails may be prepared and 32 probes as a pool may be used in hybridization/ligation. In the decoding process, four cycles each with 8 tags are used. Thus, each color is used for 4 tags used in 4 decoding cycles. After each cycle, tags may be removed or dyes photo bleached. The process requires that the last set of probes to be decoded has to stay hybridized through 4 decoding cycles.

In one embodiment, additional properties are included to provide the ability to distinguish different probes using the same color, for example Tm/stability, degradability by incorporated uracil bases and UDG enzyme, and chemically or photochemically cleavable bonds. A combination of two properties, such as temperature stability directly or after cutting or removing a stabilizer to provide 8 distinct tags for the same color; more than one cut type may be used to create 3 or more groups; to execute this 4-8 or 6-12 exposures of the same color may be required, demanding low photo-bleaching conditions such as low intensity light illumination that may be detected by intensified CCDs (ICCDs). For example if one property is melting temperature (Tm) and there are 4 tag-oligos or anchors or primers with distinct Tm, another set of 4 oligos can be prepared that has the first 4 probes connected to or intractable with a stabilizer that shifts the Tm of these 4 oligos above the most stable oligo in the first group without stabilizer. After resolving 4 oligos from the first group by consecutive melting off, the temperature may be reduced to the initial low level, the stabilizer may be cut or removed, and 4 tagged-oligos or anchors or primers can then be differentially melted using the same temperature points as for the first group.

In one aspect, probe-probe hybrids are stabilized through ligation to another unlabeled oligonucleotide.

Methods of Sequencing Using Interspersed Adaptors

In one aspect, the invention includes a method of determining a nucleotide sequence of a target polynucleotide, the method comprising the steps of: (a) generating a plurality of interspersed adaptors within a target polynucleotide, each interspersed adaptor having at least one boundary with the target polynucleotide; and (b) determining the identity of at least one nucleotide adjacent to at least one boundary of at least two interspersed adaptors, thereby determining a nucleotide sequence of the target polynucleotide. As is more fully outlined below, the target sequence comprises a position for which sequence information is desired, generally referred to herein as the "detection position". In general, sequence information (e.g. the identification of the nucleotide at a particular detection position) is desired for a plurality of detection positions. By "plurality" as used herein is meant at least two. In some cases, however, for example in single nucleotide polymorphism (SNP) detection, information may only be desired for a single detection position within any particular target sequence. As used herein, the base which basepairs with the detection position base in a hybrid is termed the "interrogation position".

An important feature of the invention is the use of interspersed adaptors in target polynucleotide amplicons to acquire sequence information related to the target polynucleotides. A variety of sequencing methodologies may be used with interspersed adaptors, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, and sequencing by synthesis methods, e.g. Nyren et al, U.S. Pat. No. 6,210,891; Ronaghi, U.S. Pat. No. 6,828,100; Ronaghi et al (1998), Science, 281: 363-365; Balasubramanian, U.S. Pat. No. 6,833,246; Quake, U.S. Pat. No. 6,911,345; Li et al, Proc. Natl. Acad. Sci., 100: 414-419 (2003); Smith et al, PCT publication WO 2006/074351; and ligation-based methods, e.g. Shendure et al (2005), Science, 309: 1728-1739, Macevicz, U.S. Pat. No. 6,306,597; which references are incorporated by reference.

In one aspect, a method of determining a nucleotide sequence of a target polynucleotide in accordance with the invention comprises the following steps: (a) generating a plurality of target concatemers from the target polynucleotide, each target concatemer comprising multiple copies of a fragment of the target polynucleotide and the plurality of target concatemers including a number of fragments that substantially covers the target polynucleotide; (b) forming a random array of target concatemers fixed to a surface at a density such that at least a majority of the target concatemers are optically resolvable; (c) identifying a sequence of at least a portion of each fragment in each target concatemer; and (d) reconstructing the nucleotide sequence of the target polynucleotide from the identities of the sequences of the portions of fragments of the concatemers. Usually, "substantially covers" means that the amount of DNA analyzed contains an equivalent of at least two copies of the target polynucleotide, or in another aspect, at least ten copies, or in another aspect, at least twenty copies, or in another aspect, at least 100 copies. Target polynucleotides may include DNA fragments, including genomic DNA fragments and cDNA fragments, and RNA fragments. Guidance for the step of reconstructing target polynucleotide sequences can be found in the following references, which are incorporated by reference: Lander et al, Genomics, 2: 231-239 (1988); Vingron et al, J. Mol. Biol., 235: 1-12 (1994); and like references.

In one aspect of the invention, a ligation-based sequencing method may be used as illustrated in FIGS. 3A-3E. Many different variations of this sequencing approach may be selected by one of ordinary skill in the art depending on factors, such as, the volume of sequencing desired, the type of labels employed, the type of target polynucleotide amplicons employed and how they are attached to a surface, the desired speed of sequencing operations, signal detection approaches, and the like. The variations shown in FIGS. 3A-3E are only exemplary.

In one aspect of the invention, a labeled probe is able to form a stable hybrid only after ligation to a pairing probe. The use of probe ligation improves data specificity over standard sequencing by hybridization methods. Probe ligation also has application in position specific base identification (e.g. DNA ends) or in a whole sequence scanning methodology (e.g. all internal overlapping sequences).

To identify sequences at a specific site in the unknown sequence, such as at the ends of the sequence, the labeled probes can be designed to allow ligation to an anchor probe. The longer anchor probe is hybridized to a known adaptor sequence that is adjacent to the end of the unknown sequence to be determined, e.g. the detection positions. Labeled probes can have various numbers of specific and degenerated bases. For example, 2 end bases can be determined with the probe BBNNNNNN (A=anchor, D=adaptor, G=genomic, B=probe defining bases, N=degenerate bases. *=label):

AAAAAAAA.BBNNNNNN*

DDDDDDDDDDDDDGGGGGGGGGGGGGGGG

For such a probe structure there are 16 sequence-reading probes, each consisting of 2 specific bases at the 5-prime end. If all 16 probes are tested, only one would efficiently ligate to the anchor probe and give a strong signal, after removing probes that are not ligated the to anchor probe. Such a positive probe detects two bases at the end of genomic DNA fragment, with a high specificity provided by the strong preference of T4 DNA ligase for complementary bases close to the ligation site.

Figure 3A:
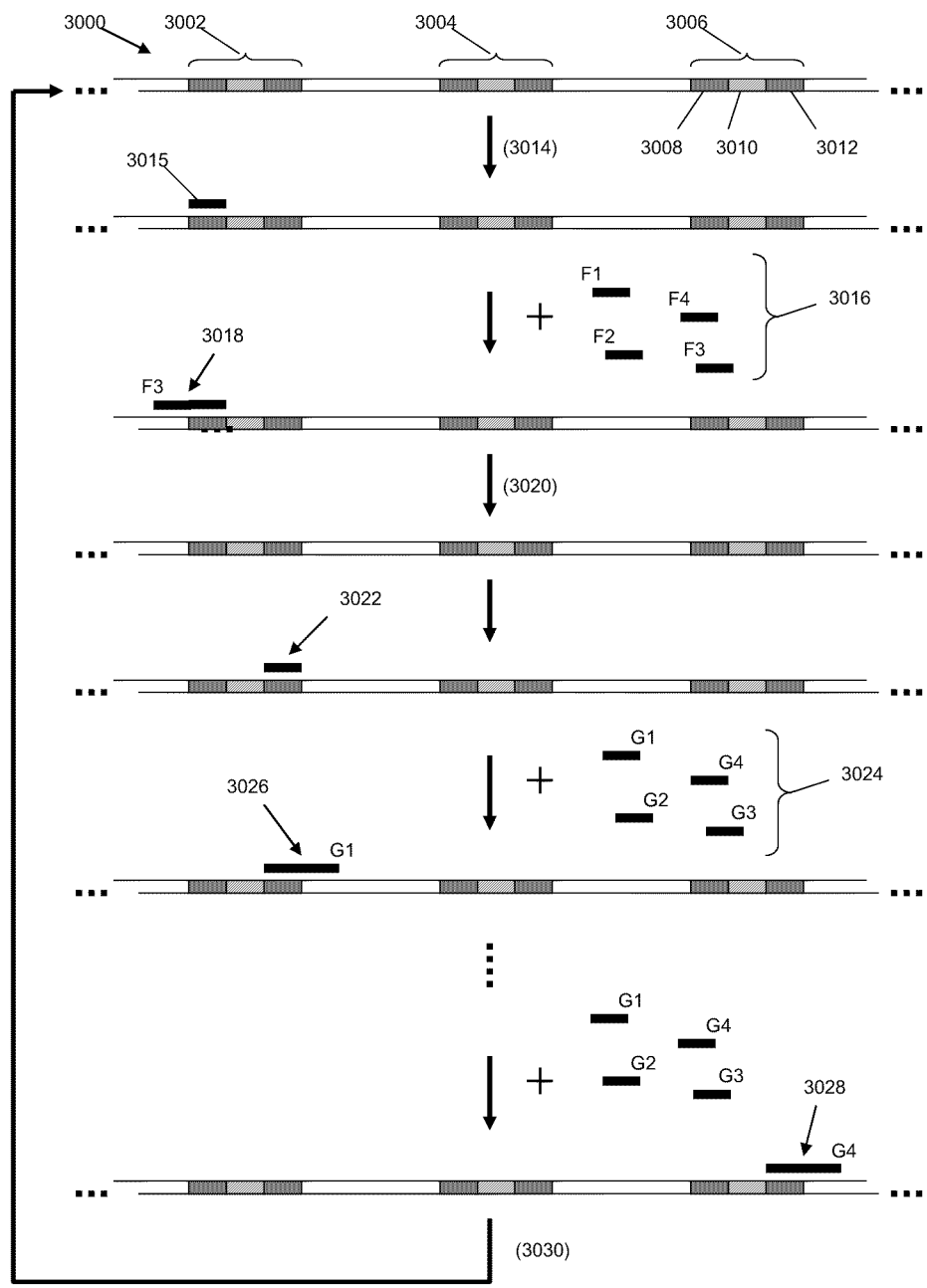
FIGS. 3A-3E illustrate a method of high-throughput sequencing that can be implemented on target polynucleotides containing interspersed adaptors.

In one aspect of the invention, a single stranded target polynucleotide is provided that contains a plurality of interspersed adaptors. In FIG. 3A, three interspersed adaptors (3002, 3004, and 3006) are shown, which may be part of an amplicon, such as a concatemer, comprising multiple copies of target polynucleotide (3000). Each interspersed adaptor has a region (e.g. 3008 and 3012) at each end that has a unique sequence (in this example six such unique sequences among three interspersed adaptors in all) designed as a binding site for a corresponding anchor probe, which is an oligonucleotide (which may or may not carry a label) to which a sequencing probe is ligated. Such end regions may have lengths in the range of from 6 to 14 nucleotides, and more usually, from 8 to 12 nucleotides. Interspersed adaptors optionally have central region (3010), which may contain additional elements such as recognition sites for various enzymes (when in double stranded form) or binding sites for capture oligonucleotides for immobilizing the target polynucleotide amplicons on a surface, and so on. In one aspect, a sequencing operation with interspersed adaptors (3002-3006) comprises six successive routines of hybridizing anchor probes to each of the different unique anchor probe binding sites. Each such routine comprises a cycle of hybridizing the anchor probe to its end site of its interspersed adaptor, combining with sequencing probes under conditions that permit hybridization of only perfectly matched probes, ligating perfectly matched sequencing probes to juxtaposed anchor probes, detecting ligated sequencing probes, identifying one or more bases adjacent to the anchor probe by the signal generated by the sequencing probe, and removing the sequencing probe and the anchor probe from the target polynucleotide amplicon.

A further embodiment includes creating a DNA circle of 300-3000 bases in length and inserting 2-3 adaptors on each side of the initial adaptor. In this way a mating pair of two, 20-60 base long sequences, separated by 300-3000 bases is generated. In addition to providing twice the level of sequence data, this method provides valuable mapping information. Mate pairs can bridge over repeats in de novo sequence assembly, and can also be used to accurately position mutations in repeats longer than 20-50 bases in genome re-sequencing. One, or a mating pair of two, ~20-50 base sequences can be complemented with probe hybridization or probe-probe ligation data. A partial set of ⅛ to 1/16 of all 5-mers, 6-mers, 7-mers or 8-mers may be scored to provide mapping information for 200-4000 base length fragments. In addition, all probes of a given length (such as all 6-mers) may be scored in 4-16 reaction chambers containing 4-16 sections of the total DNA array for a given genome. In each chamber ¼ to 1/16 of all probes may be scored. After mapping individual DNA fragments all probes can be compiled to provide 100 to 1000 reads per base in overlapped probes in overlapped fragments.

In one embodiment, the six successive routines are repeated from 1 to 4 times, preferably from 2 to 3 times, so that nucleotides at different distances from the interspersed adaptor may be identified. In another embodiment, the six successive routines are carried out once, but each cycle of anchor probe hybridization, sequencing probe hybridization, ligating, etc., is repeated from 1 to 4, or from 2 to 3 times. The former is illustrated in FIG. 3A, so that after anchor probe (3015) hybridizes to its binding site in interspersed adaptor (3002), labeled sequencing probes (3016) are added to the reaction mixture under conditions that permit ligation to anchor probe (3015) if a perfectly matched duplex is formed.

Sequencing probes may have a variety of different structures. Typically, they contain degenerate sequences and are either directly or indirectly labeled. In the example of FIG. 3A, sequencing probes are directly labeled with, e.g. fluorescent dyes F1, F2, F3, and F4, which generate signals that are mutually distinguishable, and fluorescent dyes G1, G2, G3, and G4, which also generate signals that are mutually distinguishable. In this example, since dyes of each set, i.e. F and G, are detected in different cycles, they may be the same dyes. When 8-mer sequencing probes are employed, a set of F-labeled probes for identifying a base immediately adjacent to an interspersed adaptor may have the following structure: 3'-F1-NNNNNNNAp, 3'-F2-NNNNNNNCp, 3'-F3-NNNNNNNGp, 3'-F4-NNNNNNNT. Here it is assumed that sequence (3000) is in a 5'→3' orientation from left to right; thus, the F-labeled probes must carry a phosphate group on their 5' ends, as long as conventional ligase-mediated ligation reactions are used. Likewise, a corresponding set of G-labeled probes may have the following structure: 3'-ANNNNNNN-G1,3'-CNNNNNNN-G2,3'-GNNNNNNN-G3,3'-TNNNNNNN-G4, and for ligation of these probes, their associated anchor probe must have a 5'-phosphate group. F-labeled probes in successive cycles may have the following structures: 3'-F1-NNNNNNANp, 3'-F2-NNNNNNCNp, 3'-F3-NNNNNNGNp, 3'-F4-NNNNNNTN, and 3'-F1-NNNNNANNp, 3'-F2-NNNNNCNNp, 3'-F3-NNNNNGNNp, 3'-F4-NNNNNTNN, and so on.

Returning to FIG. 3A, after ligated probe (3018) is identified, it is removed from the target polynucleotide amplicon (3020), and the next anchor probe (3022) is hybridized to its respective binding site. G-labeled sequencing probes are hybridized to the target polynucleotide so that those forming perfectly match duplexes juxtaposed to the anchor probe are ligated and identified. This process continues for each anchor probe binding site until the last ligated probe (3028) is identified. The whole sequence of cycles is then repeated (3030) using F-labeled sequencing probes and G-labeled sequencing probes that are design to identify a different base adjacent to its respective anchor probe.

Figure 3B:
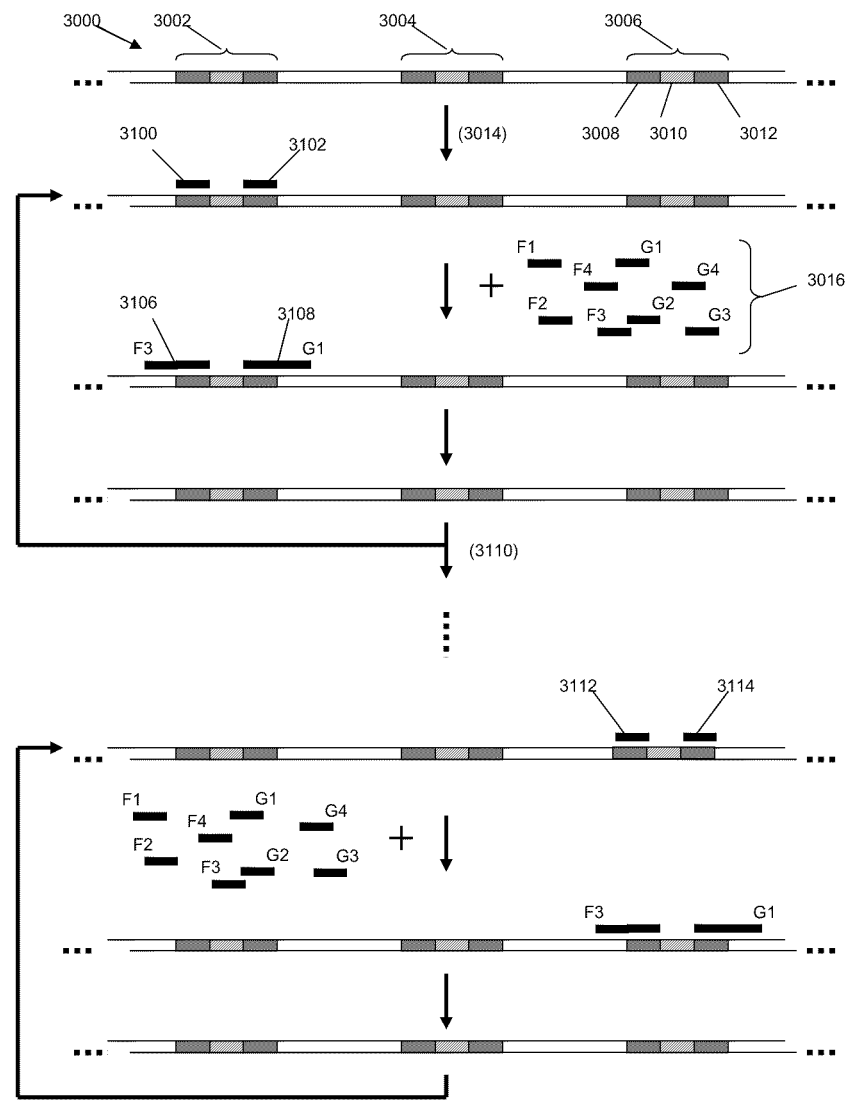

FIG. 3B illustrates a variant of the method of FIG. 3A in which anchor probes are hybridized to their respective binding sites two-at-a-time. Any pair of anchor probes may be employed as long as one member of the pair binds to a 3' binding site of an interspersed adaptor and the other member of the pair binds to a 5' binding site of an interspersed adaptor. For directly labeled sequencing probes, as shown, this embodiment requires the use of eight distinguishable labels; that is, each of the labels F1-F4 and G1-G4 must be distinguishable from one another. In FIG. 3B, anchor probes (3100 and 3102) are hybridized to their respective binding sites in interspersed adaptor (3002), after which a set of sequencing probes (3104) is added under stringent hybridization conditions. Probes that form perfectly matched duplexes are ligated, unligated probes are washed away, after which the ligated probes are identified. Cycles of such hybridization, ligation and washing are repeated (3110) with sets of sequencing probes designed to identify bases at different sites adjacent to interspersed adaptor (3002). The process is then repeated for each interspersed adaptor.

Figure 3C:
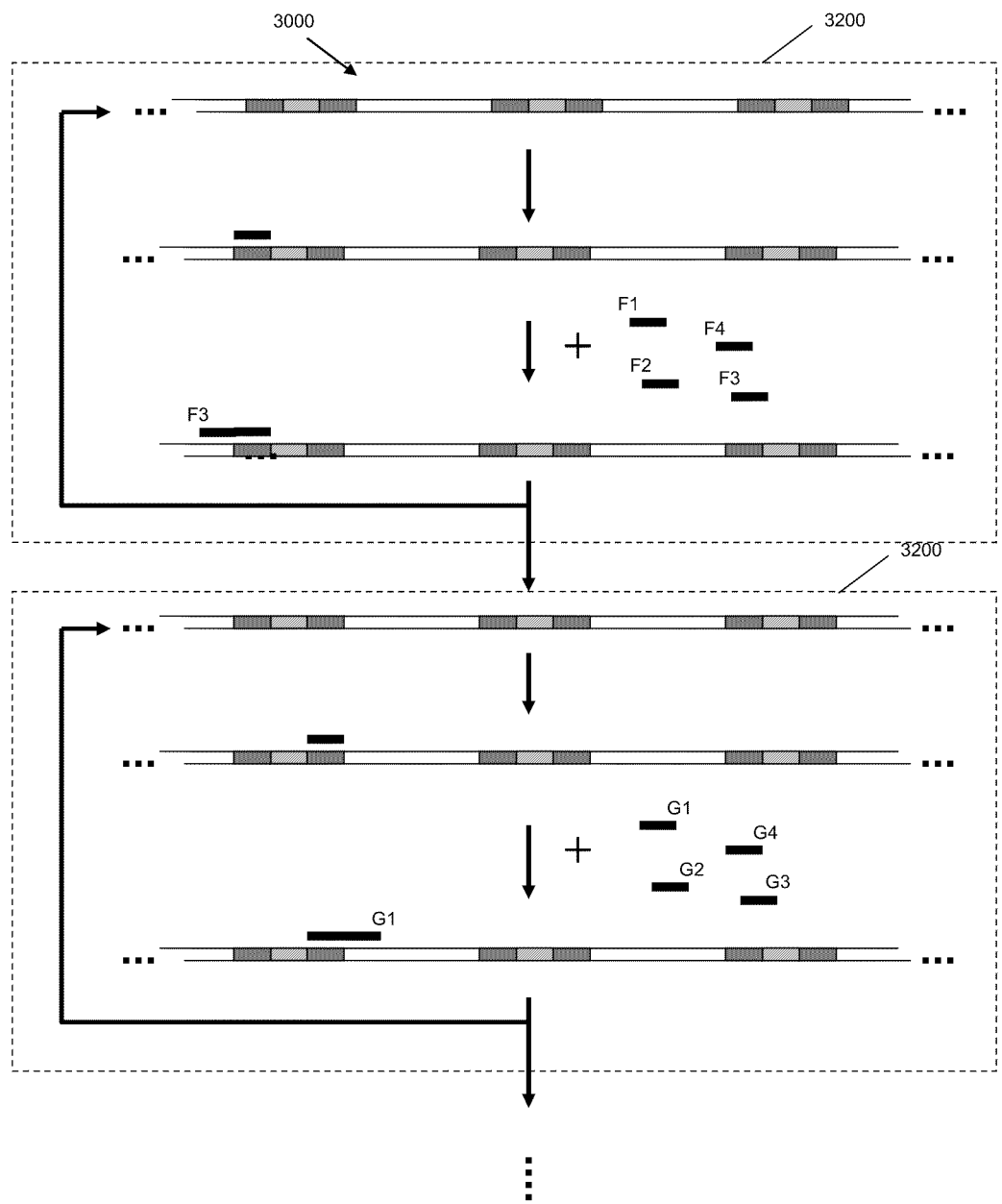

FIG. 3C illustrates another variant of the embodiment of FIG. 3A, in which sequencing probes for identify bases at every site adjacent to an anchor probe are carried out to completion before an anchor probe for any other interspersed adaptor is used. Briefly, the steps within each dashed box (3200) are carried out for each anchor probe binding site, one at a time; thus, each dashed box corresponds to a different anchor probe binding site. Within each box, successive cycles are carried out comprising the steps of hybridizing an anchor probe, ligating sequencing probes, identifying ligated sequencing probes.

Figure 3D:
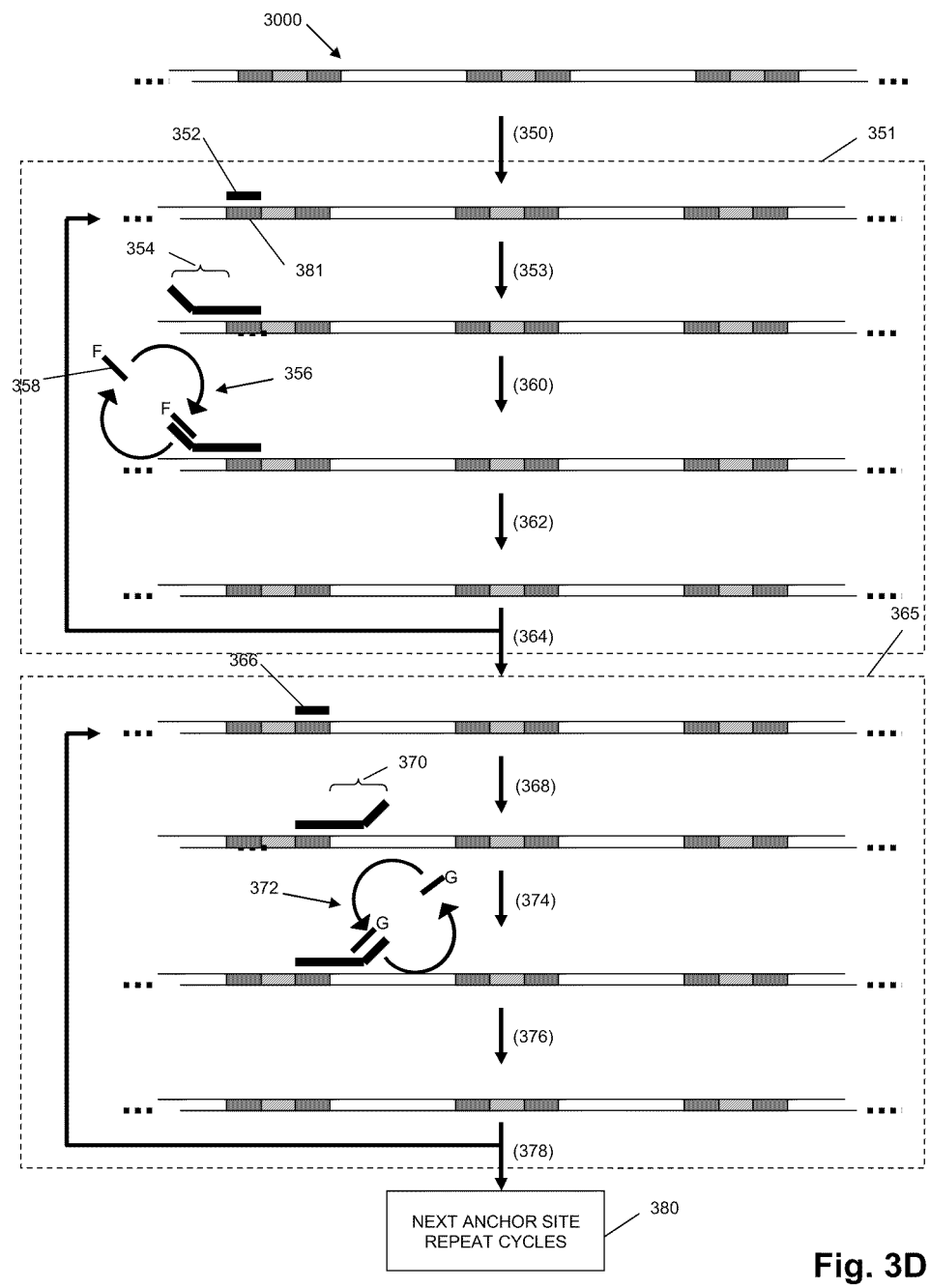

FIG. 3D illustrates an embodiment that employs encoded label, similar to those used with the encoded adaptors disclosed by Albrecht et al, U.S. Pat. No. 6,013,445, which is incorporated herein by reference. The process is similar to that described in FIG. 3C, except that instead of directly labeled sequencing probes, such probes are indirectly labeled with oligonucleotide tags. By using such tags, the number of ligation steps can be reduced, since each sequencing probe mixture may contain sequences to identify many more than four bases. For example, non-cross-hybridizing oligonucleotide tags may be selected that correspond to each of sixteen pairs of bases, so that after ligation, ligated sequencing probes may be interrogated with sets of labeled anti-tags until each two-base sequence is identified. Thus, the sequence of a target polynucleotide adjacent to an anchor probe may be identified two-at-a-time, or three-at-a-time, or more, using encoded sequencing probes. Going to FIG. 3D, anchor probe (352) is hybridized to anchor binding site (381), after which encoded sequencing probes are added under conditions that permit only perfectly complementary sequencing probes (354) to be ligated to anchor probes (352). After such ligation and washing away of un-ligated sequencing probes, labeled anti-tags (358) are successively hybridized to the oligonucleotide tags of the sequencing probes under stringent conditions so that only labeled anti-tags forming perfectly matched duplexes are detected. A variety of different labeling schemes may be used with the anti-tags. A single label may be used for all anti-tags and each anti-tag may be separately hybridized to the encoded sequencing tags. Alternatively, sets of anti-tags may be employed to reduce the number of hybridizations and washings that must be carried out. For example, where each sequencing probe identifies two bases, two sets of four anti-tags each may be applied, wherein each tag in a given set carries a distinct label according to the identity of one of the two bases identified by the sequencing probe. Likewise, if a sequencing probe identifies three bases, then three sets of four anti-tags each may be used for decoding. Such cycles of decoding may be carried out for each interspersed adaptor, after which additional cycles may be carried out using sequencing probes that identify bases at different sites.

Figure 3E:
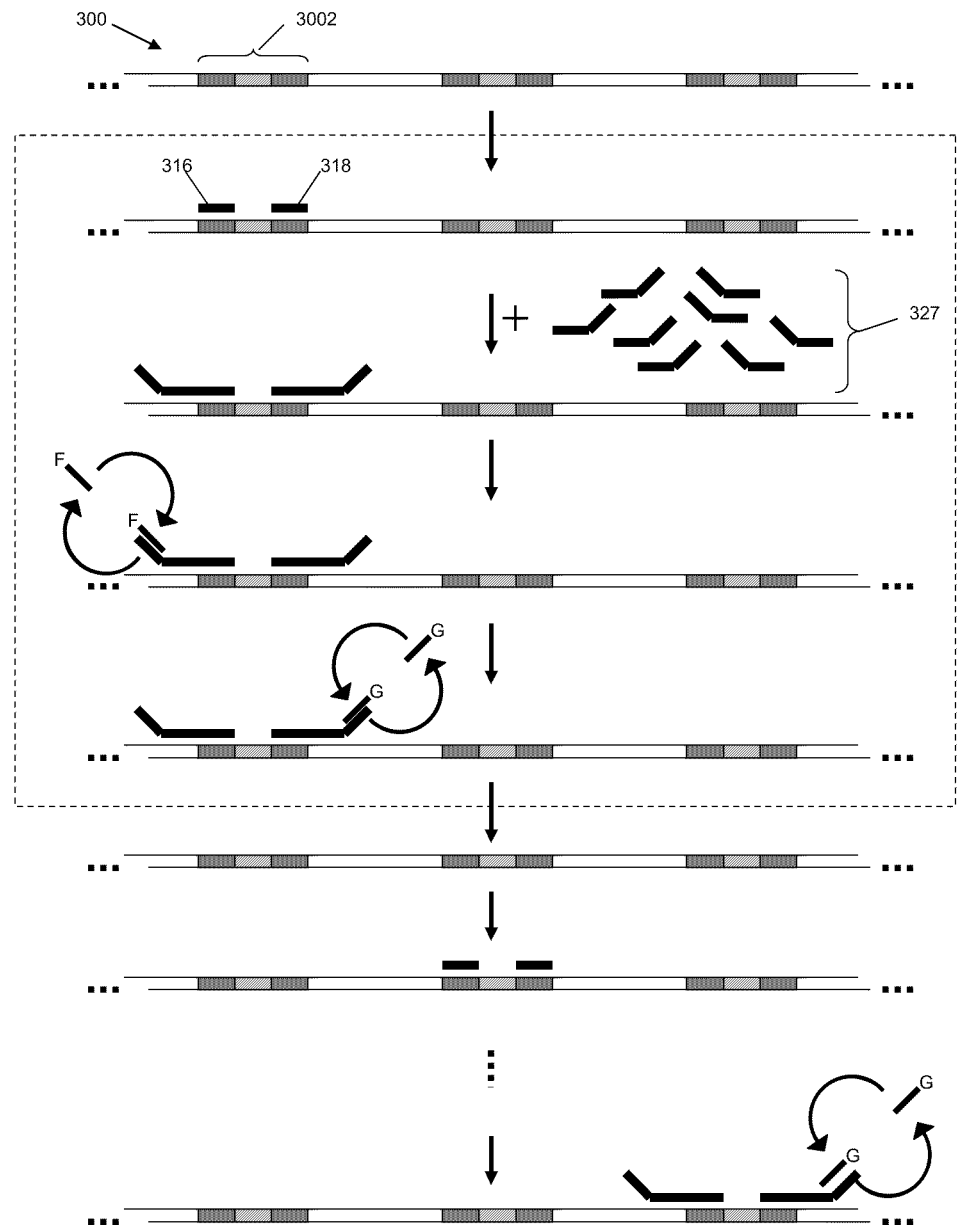

FIG. 3E illustrates an embodiment similar to that described in FIG. 3B, except that here encoded sequencing probes are employed. Thus, two anchor probes are hybridized to a target polynucleotide at a time and the corresponding sequencing probes are identified by decoding with labeled anti-tags. As shown, anchor probes (316 and 318) are hybridized to their respective binding sites on interspersed adaptor (3002), after which two sets of encoded sequencing probes (327) are added under conditions that permit only such probes forming perfectly matched duplexes to be ligated. After removal of unligated probes, the oligonucleotide tags of the ligated probes are decoded with labeled anti-tags. As above, a variety of schemes are available for decoding the ligated sequencing probes.

In another aspect, a sequencing method for use with the invention for determining sequences in a plurality of DNA or RNA fragments comprises the following steps: (a) generating a plurality of polynucleotide molecules each comprising a concatemer of a DNA or RNA fragment; (b) forming a random array of polynucleotide molecules fixed to a surface at a density such that at least a majority of the target concatemers are optically resolvable; and (c) identifying a sequence of at least a portion of each DNA or RNA fragment in resolvable polynucleotides using at least one chemical reaction of an optically detectable reactant. In one embodiment, such optically detectable reactant is an oligonucleotide. In another embodiment, such optically detectable reactant is a nucleoside triphosphate, e.g. a fluorescently labeled nucleoside triphosphate that may be used to extend an oligonucleotide hybridized to a concatemer. In another embodiment, such optically detectable reagent is an oligonucleotide formed by ligating a first and second oligonucleotide to form adjacent duplexes on a concatemer. In another embodiment, such chemical reaction is synthesis of DNA or RNA, e.g. by extending a primer hybridized to a concatemer.

In one aspect, parallel sequencing of concatemers of target polynucleotides on a random array is accomplished by combinatorial SBH (cSBH), as disclosed by Drmanac in the above-cited patents. In one aspect, a first and second sets of oligonucleotide probes are provide, wherein each sets has member probes that comprise oligonucleotides having every possible sequence for the defined length of probes in the set. For example, if a set contains probes of length six, then it contains 4096 (=$4^6$) probes. In another aspect, first and second sets of oligonucleotide probes comprise probes having selected nucleotide sequences designed to detect selected sets of target polynucleotides. Sequences are determined by hybridizing one probe or pool of probe, hybridizing a second probe or a second pool of probes, ligating probes that form perfectly matched duplexes on their target sequences, identifying those probes that are ligated to obtain sequence information about the target sequence, repeating the steps until all the probes or pools of probes have been hybridized, and determining the nucleotide sequence of the target from the sequence information accumulated during the hybridization and identification steps.

For sequencing operations, in some embodiments, the sets may be divided into subsets that are used together in pools, as disclosed in U.S. Pat. No. 6,864,052. Probes from the first and second sets may be hybridized to target sequences either together or in sequence, either as entire sets or as subsets, or pools. In one aspect, lengths of the probes in the first or second sets are in the range of from 5 to 10 nucleotides, and in another aspect, in the range of from 5 to 7 nucleotides, so that when ligated they form ligation products with a length in the range of from 10 to 20, and from 10 to 14, respectively.

In another aspect, using such techniques, the sequence identity of each attached DNA concatemer may be determined by a "signature" approach. About 50 to 100 or possibly 200 probes are used such that about 25-50% or in some applications 10-30% of attached concatemers will have a full match sequence for each probe. This type of data allows each amplified DNA fragment within a concatemer to be mapped to the reference sequence. For example, by such a process one can score 64 4-mers (i.e. 25% of all possible 256 4-mers) using 16 hybridization/stripoff cycles in a 4 colors labeling schema. On a 60-70 base fragment amplified in a concatemer about 16 of 64 probes will be positive since there are 64 possible 4-mers present in a 64 base long sequence (i.e. one quarter of all possible 4-mers). Unrelated 60-70 base fragments will have a very different set of about 16 positive decoding probes. A combination of 16 probes out of 64 probes has a random chance of occurrence in 1 of every one billion fragments which practically provides a unique signature for that concatemer. Scoring 80 probes in 20 cycles and generating 20 positive probes create a signature even more likely to be unique: occurrence by chance is 1 in billion billions. Previously, a "signature" approach was used to select novel genes from cDNA libraries. An implementation of a signature approach is to sort obtained intensities of all tested probes and select up to a predefined (expected) number of probes that satisfy the positive probe threshold. These probes will be mapped to sequences of all DNA fragments (sliding window of a longer reference sequence may be used) expected to be present in the array. The sequence that has all or a statistically sufficient number of the selected positive probes is assigned as the sequence of the DNA fragment in the given concatemer. In another approach an expected signal can be defined for all used probes using their pre measured full match and mismatch hybridization/ligation efficiency. In this case a measure similar to the correlation factor can be calculated.

A preferred way to score 4-mers is to ligate pairs of probes, for example: $N_{(5-7)}$BBB with $BN_{(7-9)}$, where B is the defined base and N is a degenerate base. For generating signatures on longer DNA concatemer probes, more unique bases will be used. For example, a 25% positive rate in a fragment 1000 bases in length would be achieved by $N_{(4-6)}$BBBB and $BBN_{(6-8)}$. Note that longer fragments need the same number of about 60-80 probes (15-20 ligation cycles using 4 colors).

In one embodiment all probes of a given length (e.g. 4096 $N_{2-4}$BBBBBB$N_{2-4}$) or all ligation pairs may be used to determine complete sequence of the DNA in a concatemer. For example, 1024 combinations of $N_{(5-7)}B_3$ and $BBN_{(6-8)}$ may be scored (256 cycles if 4 colors are used) to determine sequence of DNA fragments of up to about 250 bases, preferably up to about 100 bases.

The decoding of sequencing probes with large numbers of Ns may be prepared from multiple syntheses of subsets of sequences at degenerated bases to minimize difference in the efficiency. Each subset is added to the mix at a proper concentration. Also, some subsets may have more degenerated positions than others. For example, each of 64 probes from the set $N_{(5-7)}$BBB may be prepared in 4 different synthesis. One is regular all 5-7 bases to be fully degenerated; second is N0-3(A,T)5BBB; third is N0-2(A,T)(G,C)(A,T)(G,C)(A,T)BBB, and the fourth is N0-2(G,C)(A,T)(G,C)(A,T)(G,C)BBB.

Oligonucleotide preparation from the three specific syntheses is added in to regular synthesis in experimentally determined amounts to increase hybrid generation with target sequences that have in front of the BBB sequence an AT rich (e.g. AATAT) or (A or T) and (G or C) alternating sequence (e.g. ACAGT or GAGAC). These sequences are expected to be less efficient in forming a hybrid. All 1024 target sequences can be tested for the efficiency to form hybrid with $N_{0-3}$NNNNNBBB probes and those types that give the weakest binding may be prepared in about 1-10 additional synthesis and added to the basic probe preparation.

In another embodiment, a smaller number of probes is used for a small number of distinct samples; for example, 5-7 positive out of 20 probes (5 cycles using 4 colors) has the capacity to distinguish about 10-100 thousand distinct fragments In one aspect, 8-20-mer RCR products are decoded by providing arrays formed as random distributions of unique 8 to 20 base recognition sequences in the form of DNA concatemers. The probes are decoded to determine the sequence of the 8-20 base probe region using a number of possible methods. In an exemplary method, one half of the sequence is determined by utilizing the hybridization specificity of short probes and the ligation specificity of fully matched hybrids. Six to ten bases adjacent to the 12 mer are predefined and act as a support for a 6 mer to 10-mer oligonucleotide. This short 6 mer will ligate at its 3-prime end to one of 4 labeled 6-mers to 10-mers. These decoding probes consist of a pool of 4 oligonucleotides in which each oligonucleotide consists of 4-9 degenerate bases and 1 defined base. This oligonucleotide will also be labeled with one of four fluorescent labels. Each of the 4 possible bases A, C, G, or T will therefore be represented by a fluorescent dye. For example these 5 groups of 4 oligonucleotides and one universal oligonucleotide (Us) can be used in the ligation assays to sequence first 5 bases of 12-mers: B=each of 4 bases associated with a specific dye or tag at the end:

```
UUUUUUUU.BNNNNNNN*
UUUUUUUU.NBNNNNNN
UUUUUUUU.NNBNNNNN
UUUUUUUU.NNNBNNNN
UUUUUUUU.NNNNBNNN
```

Six or more bases can be sequenced with additional probe pools. To improve discrimination at positions near the center of the 12-mer the 6-mer oligonucleotide may be positioned further into the 12-mer sequence. This will necessitate the incorporation of degenerate bases into the 3' end of the non-labeled oligonucleotide to accommodate the shift. This is an example of probes for position 6 and 7 in the 12-mer:

```
UUUUUUNN.NNNBNNNN
UUUUUUNN.NNNNBNNN
```

In a similar way the 6 bases from the right side of the 12-mer can be decoded by using a fixed oligonucleotide and 5-prime labeled probes. In the above described system 6 cycles are required to define 6 bases of one side of the 12-mer. With redundant cycle analysis of bases distant to the ligation site this may increase to 7 or 8 cycles. Complete sequencing of the 12-mer can thus be accomplished with 12-16 cycles of ligation.

In one embodiment, the invention provides a method for partial or complete sequencing of arrayed DNA by combining two distinct types of libraries of detector probes. In this approach one set has probes of the general type $N_{3-8}B_{4-6}$ (anchors) that are ligated with the first 2 or 3 or 4 probes/probe pools from the set $BN_{6-8}$, $NBN_{5-7}$, $N_2BN_{4-6}$, and $N_3BN_{3-5}$. In an exemplary method, 1-4 4-mers or more are hybridized to 5-mer anchors to obtain 1 or 2 anchors per DNA for about 70%-80% of the molecules. In one embodiment, the positive anchor is determined by mixing specific probes with distinct hybrid stability (maybe different number of Ns in addition). Anchors may be also tagged to determine which anchor from the pool is hybridized to a spot. Tags, as additional DNA segments, may be used for adjustable displacement as a detection method. For example, EEEEEEEENNNAAAAA and FFFFFFFFNNNCCCCC probes can be after hybridization or hybridization and ligation differentially removed with two corresponding displacers: EEEEEEEENNNNN and FFFFFFFFNNNNNNNN where the second is more efficient. In another embodiment, separate cycles may be used to determine which anchor is positive. For this purpose anchors labeled or tagged with multiple colors may be ligated to unlabeled N7-N10 supporter oligonucleotides.

The BNNNNNNNN probe is then hybridized with 4 colors corresponding to 4 bases. A discriminative wash or displacement by complement to the tag is used to read which of two scored bases is associated to an anchor if two anchors are positive in one DNA. Thus, two 7-10 base sequences can be scored at the same time. 2-4 cycles can be used to extend to a 4-6 base anchor for an additional 2-4 base run of 16 different anchors per each array (32-64 physical cycles if 4 colors are used) to determine about 16 possible 8-mers (~100 bases total) per each fragment. This is sufficient to map it to the reference probability that a 100-mer will have a set of 10 8-mers is less than 1 in trillion trillions; ($10 \ e^{-28}$). By combining data from different anchors scored in parallel on the same fragment in another array complete sequence of that fragment and by extension to entire genomes may be generated from overlapping 7-10-mers.

In one aspect, the invention provides methods for tagging probes with DNA tags for larger multiplex of decoding or sequence determination probes. Instead of a direct label, the probes can be tagged with different oligonucleotide sequences made of natural bases or new synthetic bases (such as isoG and isoC). Tags can be designed to have very precise binding efficiency with their anti-tags using different oligonucleotide lengths (about 6-24 bases) and/or sequence including GC content. For example 4 different tags may be designed that can be recognized with specific anti-tags in 4 consecutive cycles or in one hybridization cycle followed by a discriminative wash. In the discriminative wash, the initial signal is reduced to 95-99%, 30-40%, 10-20% and 0-5% for each tag, respectively. In this case by obtaining two images 4 measurements are obtained assuming that probes with different tags will rarely hybridize to the same dot. Another benefit of having many different tags even if they are consecutively decoded (or 2-16 at a time labeled with 2-16 distinct colors) is the ability to use a large number of individually recognizable probes in one assay reaction. This way a 4-64 times longer assay time (that may provide more specific or stronger signal) may be affordable if the probes are decoded in short incubation and removal reactions.

The decoding process requires the use of 48-96 or more decoding probes. These pools will be further combined into 12-24 or more pools by encoding them with four fluorophores, each having different emission spectra. Using a 20× objective, each 6 mm×6 mm array may require roughly 30 images for full coverage by using a 10 mega pixel camera. Each 1 micrometer array area is read by about 8 pixels. Each image can be acquired in 250 milliseconds: 150 ms for exposure and 100 ms to move the stage. Using this fast acquisition it will take ~7.5 seconds to image each array, or 12 minutes to image the complete set of 96 arrays on each substrate.

In one embodiment of an imaging system, a high image acquisition rate is achieved by using four ten-megapixel cameras, each imaging the emission spectra of a different fluorophore. The cameras are coupled to the microscope through a series of dichroic beam splitters. The autofocus routine, which takes extra time, runs only if an acquired image is out of focus. It will then store the Z axis position information to be used upon return to that section of that array during the next imaging cycle. By mapping the autofocus position for each location on the substrate we will drastically reduce the time required for image acquisition.

Typically, each array requires about 12-24 cycles to decode. Each cycle consists of a hybridization, wash, array imaging, and strip-off step. These steps, in their respective orders, may take for the above example 5, 2, 12, and 5 minutes each, for a total of 24 minutes each cycle, or roughly 5-10 hours for each array, if the operations are performed linearly. The time to decode each array can be reduced by a factor of two by allowing the system to image constantly. To accomplish this, the imaging of two separate substrates on each microscope is staggered, i.e., while one substrate is being reacted, the other substrate is imaged.

An exemplary decoding cycle using cSBH includes the following steps: (i) set temperature of array to hybridization temperature (usually in the range 5-25° C.); (ii) use robot pipetter to pre mix a small amount of decoding probe with the appropriate amount of hybridization buffer; (iii) pipette mixed reagents into hybridization chamber; (iv) hybridize for predetermined time; (v) drain reagents from chamber using pump (syringe or other); (vi) add a buffer to wash mismatches of non-hybrids; (vii) adjust chamber temperature to appropriate wash temp (about 10-40° C.); (viii) drain chamber; (ix) add more wash buffer if needed to improve imaging; (x) image each array, preferably with a mid power (20×) microscope objective optically coupled to a high pixel count high sensitivity CCD camera, or cameras; plate stage moves chambers (or perhaps flow-cells with input funnels) over object, or objective-optics assembly moves under chamber; certain optical arrangements, using dichroic mirrors/beam-splitters can be employed to collect multi-spectral images simultaneously, thus decreasing image acquisition time; arrays can be imaged in sections or whole, depending on array/image size/pixel density; sections can be assembled by aligning images using statistically significant empty regions pre-coded onto substrate (during active site creation) or can be made using a multi step nano-printing technique, for example sites (grid of activated sites) can be printed using specific capture probe, leaving empty regions in the grid; then print a different pattern or capture probe in that region using separate print head; (xi) drain chamber and replace with probe strip buffer (or use the buffer already loaded) then heat chamber to probe strip off temperature (60-90° C.); high pH buffer may be used in the strip-off step to reduce stripoff temperature; wait for the specified time; (xii) remove buffer; (xiii) start next cycle with next decoding probe pool in set.

Combinatorial Probe Ligation for Sequencing by Hybridization

In a preferred aspect of the invention, information on the sequence of a target polynucleotide is obtained through a sequencing by hybridization method which utilizes combinatorial probe ligation. In this aspect of the invention, two complete, universal sets of short probes are exposed to target DNA in the presence of DNA ligase (R. Drmanac, U.S. Pat. No. 6,401,267, 2002). Typically one probe set is attached to a solid support such as a glass slide, while the other set, labeled with fluorophores, is mobile in solution. When attached and labeled probes hybridize to the target at precisely adjacent positions, they are ligated, generating a long, labeled probe that is covalently linked to the slide surface. A positive signal at a given position indicates the presence of a sequence within the target that complements the two probes that were combined to generate the signal.

In a preferred embodiment a universal sequencing chip, such as the HyChip™ slide developed by Complete Genomics, is used in the combinatorial sequencing by hybridization methods of the present invention. In one embodiment, each HyChip™ comprises a regular microscope glass slide containing eight replica arrays of attached 6-mers, allowing analysis using a complete set of over four million 11-mer probes per sample using 4096 arrayed 6-mers and 1024 labeled 5-mer probes. In a preferred embodiment, the sequencing method utilizing the HyChip™ system is used to sequence mixtures of separate, unrelated DNA fragments.

DNA samples for use with the sequencing methods of the present invention can be prepared by PCR.

In a preferred aspect, the invention provides an array of millions of individual polynucleotide molecules, randomly disposed on an optically clear surface at density of about one spot per square micron. These polynucleotide molecules serve as templates for hybridization and ligation of fluorescent-tagged probe pools. In one embodiment, probe pools are mixed with DNA ligase and presented to the random array. When probes hybridize to adjacent sites on a target fragment, they are ligated together, forming a stable hybrid. A sensitive mega pixel CCD camera with advanced optics can be used to simultaneously detect millions of these individual hybridization/ligation events on the entire array. Once signals from the first pool pair are detected, the probes are removed and successive ligation cycles are used to test different probe combinations. In preferred aspects of the invention, a 3.2×3.2 mm array will have the capacity to hold 10 million fragments, or approximately 1-10 billion DNA bases.

Combinatorial Labeling Using Labeled Tags

In one aspect, a single hybridization/ligation cycle can be used to test all 16 possible probes by using 16 fluorescent colors. Such a test may also be accomplished using methodologies to create fluorescent signatures from fewer fluorescent colors. In fluorescent in-situ hybridization (FISH) chromosomal "painting", combinations of fluorescent probes can be utilized to create new fluorescent signatures for that combination of probes. For example, combinations of two probes from a set of 4 can create 10 possible signature fluorescent signals, 5 can create 15, 6 can create 21 and so on. Therefore, in a single hybridization cycle it would be possible to distinguish which one of 16 probes was hybridized to the anchor probe.

Alternatively, if one of the BBNNNNNN probes was left unlabeled (and inferred by lack of signals for all other probes), 5 colors would be sufficient to label all of the remaining 15 dinucleotides. Four colors may be used to label 4 probes that read a single base, or 8 probes (out of all 16 needed probes) to read two bases. In this latter case all 16 probes could be scored in two cycles (see below). Thus, a 5 or 6 color system may be much easier to implement than 16 colors required by non-combinatorial labeling.

For efficient combinatorial labeling, 2-mer probes may be prepared with a tail sequence containing tag binding sites. Tail sequences can be combinatorially designed for binding 2 out of 5 (or 6) labeled oligonucleotide tags or 16 tags with one or two fluorescent dyes can be synthesized for each of the 16 tails. Use of labeled tags instead of directly labeled probes has additional advantages. Testing all 16 BBNNNNNN probes would require about 1024-fold more probe (assuming low discrimination at positions further from the ligation site) than for a single probe. For example, to have the probe AGCTANNN at 1 μM concentration within a probe mix of BBNNNNNN, the mix should need to be at 1024 μM. Since labeled probes are much costlier to synthesize than unlabeled probes, the unlabeled probes could be detected with a tail sequence, with the labeled tag probe used at a low concentration since it may be perfectly complementary to the tail sequence. Additionally, using unlabeled tailed probes would be advantageous in maintaining a lower background because the fluorophore would be at low concentration. An overall 100-fold cost reduction is expected by using 6 labeled tags (without degenerate bases) instead of the equivalent 1024 labeled probes.

Tags also provide an efficient option to use only 4 colors to read all 16 dinucleotides in a single ligation reaction. In such an embodiment, two sets of 4 distinct tags may be designed for decoding 8 2-mers each. All 16 2-mers can be decoded in two decoding cycles. This strategy can be expanded to use the same 4 colors for reading 2 bases on each end of an adaptor. In this case, 4 groups of 4 tags may be used in 4 decoding steps for each ligation cycle that reads 4 bases. Performing multiple decoding cycles instead of multiple ligation cycles is less expensive (less enzyme is used), and ligation cycles may be extended for longer time, with lower probe concentration, to reduce mismatch ligation.

Tags may also be designed to minimize interference with the analyzed DNA, for example by using isoC and isoG base pairs that do not pair with natural bases. Another option is to use standard DNA chemistry but design sequences that are very infrequent in the human genome. Yet another option is to use a probe with tails pre-hybridized with unlabeled tags that would be removed after ligation and before hybridization with labeled tags.

Expanding the Number of Bases that can be Decoded

To read further than 2 nucleotides from the anchor probe can in some aspects of the invention utilize additional rounds of probe-anchor ligation, with removal of the anchor/label probe from the target prior to the initiation of the next cycle. The ligated probe-anchor can be removed using a number of methods known in the art, including by heating, or by temperature or light cleavable bonds in the anchor probe, such that the anchor is fragmented and destabilized in the heating step. Since the bases to be sequenced are now 3 and 4 bases from the adaptor, modifications need to be made to the anchor probe or labeled probe. In the case of the anchor probe, it can in one embodiment of the invention be prepared with 2 additional degenerate bases at the ligation end. To ensure that the efficiency of the subsequent ligation is maintained, in one embodiment the anchor is constructed through ligation of two shorter oligonucleotides on the template DNA. Alternatively, the sequencing probe can be prepared with two degenerate bases at the ligating end in the manner of: NNBBNNNN-tag. In another aspect of the invention, the assay may be designed to read an additional 2 bases using 16 anchor probes.

The specificity of probe-anchor ligation is very high because only 2-4 bases around the ligation site are tested. The average discrimination for these bases is 50-100 fold. Some mismatches such as GT are considerably stronger, having discriminations of only 5-20 fold. In an embodiment of the invention, software is provided that can take the differences in discrimination of certain mismatches into account.

In an aspect of the invention, each probe, anchor and tag is optimized (for example, by concentration, number of degenerated bases, sequence and length of tags) to maximally equalize full match signals. Overlapped and shifted pairs of probes and anchors may be designed in one embodiment of the invention to read each base 2-3 times to increase base calling accuracy.

The insertion of additional internal adaptors with anchor regions at precise short distances expands the sequencing capability of bases at defined positions in the genomic fragment. For example, having the original plus 2 additional adaptors spaced 8 bases apart allows the determination of 20 continuous bases in 10 cycles, by reading 4 bases from 5 consecutive adaptor ends.

```
Initial    First 8        2nd 8              Additional
adaptor    bases    Adaptor 2  bases  Adaptor 3  ~200 bases
DDDDDDDDDDGGGGGGGGDDDDDDDDDDGGGGGGGGDDDDDDDDDDGGGGGGGGGG AAAAAAA.BBNNNNNN-tail AAAAAAA.BBNNNNNN-tail AAAAAAA.BBNNNNNN-tail AAAAAAA.NNBBNNNN-tail AAAAAAA.NNBBNNNN-tail AAAAAAA.NNBBNNNN-tail tail-NNNNBBNN.AAAAAAA tail-NNNNBBNN.AAAAAAA tail-NNNNNNBB.AAAAAAA tail-NNNNNNBB.AAAAAAA
D = adaptor, G = genomic DNA, A = anchor, B = specified probe base,
 N =
degenerate probe base.
```

Multiple adaptors also provide the opportunity to further increase the reading capacity and to be able to determine more than 2 bases per cycle. In one embodiment, 4-12 bases are identified per cycle. In another embodiment, 4-8 bases are identified per cycle. In yet another embodiment, 12-16 or more bases are determined per cycle.

In one embodiment, 3 adaptors are positioned 12 bases apart, allowing for 30 bases of continuous sequence to be obtained by reading 6 bases at each of 5 ends. In another embodiment, a total of 4 adaptors and reading 16 bases between two adaptors generates a continuous sequence of 56 bases in 28 cycles. In other embodiments, two (initial plus one additional) adaptors separated by 16 bases to read 24 bases are used.

In one embodiment, multiple bases are identified per cycle by simultaneously hybridizing probes to multiple or all anchor sites with the same set of 16 dinucleotide probes used at each anchor site but read each anchor site independently. In one embodiment, this simultaneous probe ligation is achieved by designing anchors with different melting temperatures and measuring color intensities at multiple predefined temperatures.

In another embodiment, multiple adaptors are used for cyclical primer extension to provide longer reads with fewer cycles from each individual primer.

In one embodiment, mapping information can be obtained by scoring a sufficient number of short sequences distributed over the entire DNA fragment without any positional information or from a smaller number of short sequences at precise locations. A variant of this process is referred to as "hybridization signature" where expected and observed intensities are compared. In another embodiment, the short sequences may be designed to provide localized (intermittent or continuous) sequence information. Three examples of such short sequences may be represented schematically as follows:
a. (X)aBB(X)bBB(X)cBB(X)dBB(X)eBB(X)f . . .
b1. BBX6BBX4BBX6BBX4BBXa . . .
b2. B16Xa The number of oligonucleotide sequences needed for complete mapping information depends on the size of the target sequence, the size of the DNA fragments used and on the complexity of the source DNA. For human and other similarly complex genomes about 5 positive 8-mers or 10 positive 6-mers may be sufficient for 100 base DNA fragments. To score one positive 8-mer in 2 cycles, about 10 cycles total can be used by employing 3-fold more cycles than anchor sequencing. In one embodiment, this process does not utilize insertion of two anchors and may be done without enzyme using direct hybridization. In such an embodiment, 3000 8-mers can be utilized.

In one embodiment the same set of probes may be used in different group combinations (combinatorial pooling) to decode which probe from the pool of probes with identical labels is positive. For example, all 3000 probes labeled with 300 distinct labels may be scored in two reactions by having 5 probes labeled with the same probe combination. In addition to 6 true positives, some other 30 or more pool-related false positives will be found in these two reactions. By performing another two hybridization cycles where probes will be grouped differently, only true positive probes will be decoded since they are shared positives between two data sets and with less than one false positive probe being shared. Finding positive probes may be performed by using the lower of the two scores for each probe. For true positive probes the lower score is expected to be high. For most negative probes (5×3+3 at a distance of 20-30 bases), and in yet another embodiment 4 times less tags for 3-mers, may need 3 anchors (3×6+3+3 bases).

In one aspect, a high capacity DNA array platform can be used to analyze 100 patient or other DNA samples simultaneously. In the direct hybridization (or combinatorial ligation) approach of mapping, only a subset of probes is used and does not provide tag sequence automatically. For 4-base tags all 256 probes (e.g. NxUxBBBBUxNx) may be used for mapping or as additional probes. If these probes are also used for mapping multiple sets of 256 shifted probes may be needed to identify the tag sequence.

In one aspect, 5-6 colors are used to decode all 16 dinucleotides and read 2-12 bases in one decoding cycle. In one embodiment, a set of 4 tabs is used; in another embodiment, the set is expanded to 6 tags. Multiple decoding cycles alone or in combination with anchors with different melting temperatures can be used to increase the number of bases that can be read in a single decoding cycle.

In one aspect, 4 bases per ligation cycle are read by testing 2 bases on each end of an adaptor and by using two corresponding anchors. Both types of probes B2N6-tail and tail-N6B2 may be used simultaneously. Each probe type may have unique tails and a matching set of 6 unique tags. Two decoding cycles, using two sets of 6 tags, would identify 4 bases. In 11 ligation cycles 42 continuous and 2 redundant bases would be determined. To read a mate-pair of 42+18=60 bases, 15 ligation cycles would be required.

In another aspect, 8 bases are read per ligation cycle. A total of 4 anchors may be used (each of two sides of two adaptors). Probes and tags may be the same as in the first option. Thus, in two decoding cycles 2 bases on each side of one adaptor can be determined. Because an additional 2 anchors may be used for the second adaptor, additional information is needed to discriminate which of the two positive 2-mers belongs to which anchor/adaptor end. This can be achieved by designing the two anchors for the second adaptor with higher melting temperatures (Tm). Thus, schematically, the 4 anchors are:

```
                adaptor 1                      adaptor2
. . . GGGGDDDDDDDDDDDDDDDDDGGGGGGGGGGGGGDDDDDDDDDDDDDDDDDDDDDDDDDDGG
      GGG . . .
                AAAAAAAA AAAAAAAA              AAAAAAAAAAAA AAAAAAAAAAAA
        D = adaptor bases, G = genomic bases, A = anchor bases,
``` at least one score will be very low, and so it will cancel one false positive score. This process helps reduce the number of cycles or number of required labels and may provide enough power for many applications without the need to use combinatorial labeling.

In another embodiment, highly overlapped sets of fragments analyzed in the form of 2-16 subsets on different sub-arrays with different subsets of probes provides a large amount of mapping information. For example 250 base fragments starting at every base on average can be analyzed as 2-16 subsets with 2-16 different subsets of probes. DNA fragments that are shifted only 2-26 bases will be analyzed with a few if not all used probe subsets providing unique chromosomal identification with at least one probe subset.

Typically, twenty specific bases will provide the information necessary for most unique sequences. In one embodiment, this information can be obtained with two anchors in 5 cycles with 256 tags for reading 5×4 bases, or 3 cycles for 24 bases by reading 8 bases per cycle (512 tagging combinations). In another embodiment, 3 cycles×6 bases=18 bases After two standard cycles of decoding and imaging of 5-6 dyes, a stringent wash can be applied that removes low Tm anchors and the tailed probes that are ligated to them, but does not affect high Tm anchors. By repeating two cycles of tag binding and measuring fluorescence, the fluorescence signals specific to the second adaptor with longer (higher Tm) anchors is determined. The difference between the first and second set of measurements gives the signal produced by 2-mers corresponding to the first adaptor. A strip-off wash at even higher temperature would remove higher Tm anchors and free DNA for the next ligation cycle. Higher Tm anchors may be photo, chemically or temperature cleavable for easy strip-off. To read more bases the process can be repeated 3 times to read 24 bases surrounding two adaptors, or 6 times to read 48 bases surrounding 4 adaptors. To read the remaining 12 bases for the fifth adaptor, 3 additional cycles may be required. In these 3 cycles, repeat sequencing of 12 previously sequenced bases with the same or shifted anchor-probe pair may also serve as a control of data quality. In total, 9 ligation cycles and 36 decoding cycles can be used to determine 72 bases (60 unique and 12 repeated).

In another aspect, 12 bases are read per cycle by expanding the process from 2 to 3 levels, providing a read of 12 bases (3×2×2) per ligation cycle. Similarly, 72 bases (60 unique and 12 repeated) can be determined in just 6 ligation cycles. The Tm approach can be used in many other configurations with an increased number of anchors that can be differentially removed one by one. The key advantage of this approach is that in one ligation reaction, probes of one type are ligated to 3 different anchors.

In another aspect, 8 bases are read in one ligation cycle without using Tm differentiation of anchors. To achieve this, the anchor probes are designed to read 2 bases simultaneously with a 2 base read by the non-anchor probes. Two such pairs can be analyzed in one ligation cycles reading a total of 8 bases per cycle as follows.

```
DDDDDDDDGGGGGGGGGGGGGDDDDDDDDDDDDDDDDDDDGGGGGGGGGGGGGDDDDDDDD tail-AAAAAABB.BBNNNNNN-TAIL                TAIL-NNNNNNBB.BBAAAAAA-tail
(cycle 1)

tail-AAANNNNBB.BBNNNNNN-TAIL        TAIL-NNNNNNBB.BBNNNNAAA-tail
(cycle 2)

tail-NNNNNNNBB.BBAAAAAA-TAIL  TAIL-AAAAAABB.BBNNNNNN-tail
(cycle 3)
D = adaptor bases, G = genomic bases, A = anchor bases, B = specified probe
bases, N = degenerate probe bases
```

Decoding would be performed in four cycles having 4 sets of tags specific for each of 4 tail groups. Interestingly, this approach may provide 44+20=64 bases using 5 adaptors (8+4×12+8) in 8 ligation cycles without generating any redundant base reads. Reading 16 instead of 12 bases between two adaptors and a total of 80 bases using 5 adaptors is a natural progression for this system. The main new development that may be required is to implement a stabilization process for the probe-anchor ligation product that is compatible with the encoding tail present at the anchor probe.

These processes coupled with inserting 1-2 additional adaptors 12 bases apart, can increase parallel reading per ligation cycle from 2 to 8 or even 12 bases in just 6-15 ligation cycles. In a further embodiment, 16 bases are read between neighboring adaptors, allowing the use of only the initial +2 inserted adaptors, leading to the ability to determine 40 (2×16+8) bases of continuous sequence.

Multiplex Probe-Anchor Ligation Assay

In one aspect, probe sets comprising 16 probes of the structure BBNNNNNN-tail in which the tail is approximately 15 to 20 bases in length and a complementary tag sequence to the tail labeled with fluorophores are prepared. Tails and tags are designed to minimize interference with the analyzed DNA. In one embodiment, tail and tag sequences are prepared from iso-c and iso-g nucleotides to prevent the tag sequence from interacting with the template DNA.

It is possible to test the efficiency of different BBNNNNNN-tail probes with different tail and tag sequences. Sixteen tail sequences may be required, but only eight of the 16 probes (with 16 different tails) may be analyzed in each decoding cycle since the maximum capacity of the 4-color mixing is 10 possible combinations of two (not including a null signal as a possible probe indicator). Each tail sequence may have the capacity to bind two tags, and each tag in this design may only have one fluorophore attached. An initial design of a set of 4 tags, one for each color may be performed. The complementary sequences of these tags may be combined to create 8 tails (out of a total of 10 possible combinations). The remaining 8 of the 16 tails may also require an additional set of 4 tags but they can carry the same fluorophores as used for the first set of 4 tags.

In one aspect, probes may be prepared with a single fluorophore (e.g., TAMRA) to determine the relative strengths of the different tag combinations (i.e. hybrid strengths). Once this information is obtained it is possible to match the fluorophores to the tags to normalize intensities. A single fluorophore set of tags can also be used to determine the relative efficiencies of the BBNNNNNN region of the probe with a common tail structure. Once these parameters have been determined, a set of 16 BBNNNNNN-tail probes can be prepared. This probe set may be used to hybridize to RCR products derived from the PCR and synthetic target circles or even complex genomic samples.

In one embodiment, arrayed RCR targets are first hybridized with an adaptor probe to determine the DNB locations and relative intensities. This probe is removed using standard techniques, such as by raising the temperature, and a second set of probes can then be hybridized to the array. The second probe set contains an anchor probe and 16 BBNNNNNN-tail probes in a ligation mix. The reaction proceeds for a sufficient length of time, preferably for about 30 minutes, and the unligated, unhybridized probes are then washed away. The next addition to the chamber can include the 4 tag probes that hybridize to the tails of ligated and hybridized BBNNNNNN probes. This hybridization can in some embodiments be as short as 5 minutes to achieve high signal intensities. The chamber is again washed and imaging occurs at the desired wavelengths. The chamber then undergoes heating to remove the tags but maintain the anchor-BBNNNNNN-tail probes in the hybrid. The second group of 4 tags can then be hybridized to score the presence of the second group of 8 BBNNNNNN probes. The level of discrimination between the matching BBNNNNNN probe and the other 15 mismatch BBNNNNNN probes can be determined through the level and combinations of signal intensity.

In one embodiment, to establish a probe-anchor ligation assay, a probe is provided, for example a probe of structure AANNNNNN, to generate enough of a signal for an AATA-TANN DNA spot with a low $\Delta G$ for the TATA sequence. If the signal for the optimal condition is low for some DNA sequences, matching probes can be prepared independently and added into the mix to selectively boost concentrations only for these probes. If 20 sequences out of 256 at the first 4 degenerated positions have to be adjusted, 16×20 additional probes can be prepared.

In one embodiment, development and testing 16 probes for reading 2-base sequences from the other side of the genomic segment between two adaptors is accomplished. Tail and degenerated bases for these probes may be at the 5' end, e.g. Tail-NNNNNNBB.

In one aspect of the invention, the number of dyes that can be differentiated is maximized by using multiple specific excitation patterns and a maximal number of filters for each excitation pattern. For example, 2-4 excitations, each with 4 different wave lengths (total of 16 wave lengths) can be used in combination with 8-16 filters for each excitation. Algorithm and software is used to analyze intensity patterns and deduce the amount of signal from each of the 8-24 dyes.

In one embodiment, direct labeling with dyes is combined with indirect labeling using haptens (such as biotin) to specifically stain multiple probes. Directly attached dyes may be photo-bleached or differences in the intensity may be calculated before and after staining.

In one embodiment, the number of color labels available for use is expanded by light or chemical de-blocking of quenchers or chemical modifications that shift absorption of the given dye. Color intensities are measured before and after de-blocking treatment. After the first imaging is done the dye may be photo-bleached before an increase of signal for the given wave length is measured. With multiple types of quenchers or modifiers (3-4-6) and 8 colors a total of 24-48 non combinatorial labels can be generated. Combinatorial labeling with 2 out of 24-48 labels gives a potential of 276-1128 two-label combinations.

Long stable anchors provide can improve probe hybridization and ligation to different targets. In one embodiment, the number of degenerate bases is increased to minimize the influence of target sequences that form unstable hybrids such as 5'TATA3'. This may increase the stability of probe/target hybrid but a probe that does not have a full match at the first 2-4 positions close to the ligation site may hybridize to the target and prevent ligation. To minimize this negative influence, one embodiment provides a higher starting temperature and/or temperature cycling to increase the number of ligatable probes hybridized next to the anchor.

Sequencing Using Primer Extension

End sequencing may be performed from one anchor/primer end by many consecutive cycles of single base extension using specifically labeled nucleotides. In one embodiment, the process includes a step in which the dye or blocker is removed to repeat the extension. Multiple adaptors provide increased flexibility in this process. In one embodiment, 2-6 or more bases are read by single base primer extension using shifted primers in consecutive reactions. Multiple simultaneous shifted 0+1 or 1+1 primer frames on one adaptor or single frame on multiple adaptors or both may be used.

In one embodiment, using the initial plus 3 additional anchors provides 4 primers. By reading 4 bases of each primer, 16 bases are determined in 16 cycles using 4 standard colors, which can be accomplished without combinatorial labeling or tagging. In this embodiment, the primer extension does not have degenerate bases on the labeled component, thus reducing the concentration of dyes used. Because 16 bases may not be sufficient for mapping, 4 primers×5-6 bases of extension in 20-24 cycles can be used.

Multiplex primer extension is possible by discriminative removal of the primers. Several different methods may be used for such removal based on factors including: primer length, GC content, base or backbone modifications such as LNA or PNA, uracil incorporation, or light sensitive linkage between selected bases. Two to eight stability levels in one group may be designed. Also 2 to 4 distinct groups that may have different stabilizers or protectors can be used. By applying these labeling methods, 20-24 bases may be determined in as few as 3-5 enzymatic cycles. In another embodiment, a primer protection assay for multiplex primer extension one base at a time is used. In such an embodiment, the primer, for example UUUUUUUNNN, used for the fourth extension provides enough signal because mismatches at NNN can occupy over 50% or over 90% of the target and would not be efficiently extended. Primer with higher specificity may be created by ligating UUUUUUU.UUUNNN or UUU-UUUU.UNNNNN.

In one aspect, in order to be able to sequence on each side of the anchor, the attached ssDNA may be converted in dsDNA using the attached primer and removal of the original strand or primer invasion techniques. One approach to remove the original strand is to incorporate in inserted adaptor binding site for a restriction enzyme that cuts only one strand. The fragmented strand would then be denatured and washed away.

For performing consecutive or overlapped frames or reading 2-3 bases a different anchor and or probe design may be used. For example:

```
Cycle 1:
UUUUUUUUUUU.BBNNNNNN

Cycle 2:
UUUUUUUUUNN.BBNNNNNN
or

UUUUUUUUUUU.NNBBNNNN

Cycle 3:
UUUUUUUUUNN.NNBBNNNN
```
Where U represents common pre-defined bases, a specified base and N a degenerate base Anchors that have degenerated bases may be designed in two parts to assure preferential binding of anchors that have matching bases at degenerate positions. Overlapped or shifted frames may be used to read each base multiple times in the same target. Two examples for multiple reading of the first four bases after the anchor are presented below:

```
UUUUUUUUUU.UBBNNNNN

UUUUUUUUUU.BBNNNNNN

UUUUUUUUUN.BBNNNNNN

UUUUUUUUUU.NNBBNNNN

UUUUUUUUNN.BBNNNNNN

UUUUUUUUUN.BBNNNNNN
```
Where U represents common pre-defined bases, B a specified base and N a degenerate base.
The ligation site is indicated with a period (.)

Detection Instrumentation

In one aspect of the invention, hardware is provided to allow detection of the ligation and hybridization events of the sequencing methods. In one embodiment, the system hardware comprises three major components; the illumination system, the reaction chamber, and the detector system. The detection instrument can include several features such as: adjustable laser power, electronic shutter, auto focus, and operating software.

Signals from single molecules on random arrays made in accordance with the invention can generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, Scanning Electron Microscopy: Physics of Image Formation and Microanalysis, 2nd Edition (Springer, 1998); Nie et al, Anal. Chem., 78: 1528-1534 (2006); Hecht et al, Journal Chemical Physics, 112: 7761-7774 (2000); Zhu et al, editors, Near-Field Optics: Principles and Applications (World Scientific Publishing, Singapore, 1999); Drmanac, International patent publication WO 2004/076683; Lehr et al, Anal. Chem., 75: 2414-2420 (2003); Neuschafer et al, Biosensors & Bioelectronics, 18: 489-497 (2003); Neuschafer et al, U.S. Pat. No. 6,289,144; and the like. Of particular interest is TIRFM, for example, as disclosed by Neuschafer et al, U.S. Pat. No. 6,289,144; Lehr et al (cited above); and Drmanac, International patent publication WO 2004/076683.

In one aspect, instruments for use with arrays of the invention comprise three basic components: (i) a fluidics system for storing and transferring detection and processing reagents, e.g. probes, wash solutions, and the like, to an array; (ii) a reaction chamber, or flow cell, holding or comprising an array and having flow-through and temperature control capability; and (iii) an illumination and detection system. In one embodiment, a flow cell has a temperature control subsystem with ability to maintain temperature in the range from about 5-95° C., or more specifically 10-85° C., and can change temperature with a rate of about 0.5-2° C. per second.

In one aspect, a flow cell for 1" square 170 micrometer thick cover slips can be used which have been derivatized to bind macromolecular structures of the invention. The cell encloses the "array" by sandwiching the glass and a gasket between two planes. One plane has an opening of sufficient size to permit imaging, and an indexing pocket for the cover slip. The other plane has an indexing pocket for the gasket, fluid ports, and a temperature control system. One fluid port is connected to a syringe pump which "pulls" or "pushes" fluid from the flow cell the other port is connected to a funnel like mixing chamber. The chamber, in turn is equipped with a liquid level sensor. The solutions are dispensed into the funnel, mixed if needed, then drawn into the flow cell. When the level sensor reads air in the funnels connection to the flow cell the pump is reversed a known amount to back the fluid up to the funnel. This prevents air from entering the flow cell. The cover slip surface may be sectioned off and divided into strips to accommodate fluid flow/capillary effects caused by sandwiching. Such substrate may be housed in an "open air"/"open face" chamber to promote even flow of the buffers over the substrate by eliminating capillary flow effects. Imaging may be accomplished with a 100× objective using TIRF or epi illumination and a 1.3 mega pixel Hamamatsu orca-er-ag on a Zeiss axiovert 200, or like system. This configuration images RCR concatemers bound randomly to a substrate (non-ordered array). Imaging speed may be improved by decreasing the objective magnification power, using grid patterned arrays and increasing the number of pixels of data collected in each image.

In one embodiment, four or more cameras may be used, preferably in the 10-16 megapixel range. Multiple band pass filters and dichroic mirrors may also be used to collect pixel data across up to four or more emission spectra. To compensate for the lower light collecting power of the decreased magnification objective, the power of the excitation light source can be increased. Throughput can be increased by using one or more flow chambers with each camera, so that the imaging system is not idle while the samples are being hybridized/reacted. Because the probing of arrays can be non-sequential, more than one imaging system can be used to collect data from a set of arrays, further decreasing assay time.

During the imaging process, it is preferable that the substrate remain in focus. Some key factors in maintaining focus are the flatness of the substrate, orthogonality of the substrate to the focus plane, and mechanical forces on the substrate that may deform it. Substrate flatness can be well-controlled, and glass plates which have better than ¼ wave flatness are readily obtained. Uneven mechanical forces on the substrate can be minimized through proper design of the hybridization chamber. Orthogonality to the focus plane can be achieved by a well adjusted, high precision stage. Auto focus routines generally take additional time to run, so it is desirable to run them only if necessary. In a preferred embodiment, each image is acquired and then analyzed using a fast algorithm to determine if the image is in focus. If the image is out of focus, the auto focus routine will be triggered. The system will then store the objectives Z position information to be used upon return to that section of that array during the next imaging cycle. By mapping the objective's Z position at various locations on the substrate, it is possible to reduce the time required for substrate image acquisition.

In one aspect, suitable illumination and detection system for fluorescence-based signal is a Zeiss Axiovert 200 equipped with a TIRF slider coupled to an 80 milliwatt 532 nm solid state laser. The slider illuminates the substrate through the objective at the correct TIRF illumination angle. TIRF can also be accomplished without the use of the objective by illuminating the substrate though a prism optically coupled to the substrate. Planar wave guides can also be used to implement TIRF on the substrate Epi illumination can also be employed. The light source can be rastered, spread beam, coherent, incoherent, and originate from a single or multi-spectrum source.

One embodiment for the imaging system includes a 20× lens with a 1.25 mm field of view. A 10 megapixel camera is used for detection. Such a system is able to image approximately 1.5 million concatemers attached to the patterned array at 1 micron pitch. Under such a configuration, there are approximately 6.4 pixels per concatemer. The number of pixels per concatemer can be adjusted by increasing or decreasing the field of view of the objective. For example, a 1 mm field of view yields a value of 10 pixels per concatemer and a 2 mm field of view yields a value of 2.5 pixels per concatemer. The field of view may be adjusted relative to the magnification and numerical aperture of the objective to yield the lowest pixel count per concatemer that is still capable of being resolved by the optics, and image analysis software.

Both TIRF and EPI illumination allow for almost any light source to be used. One illumination schema provides a common set of monochromatic illumination sources (about 4 lasers for 6-8 colors) which is shared amongst imagers. Each imager collects data at a different wavelength at any given time and the light sources would be switched to the imagers via an optical switching system. In such an embodiment, the illumination source preferably produces at least 6, but more preferably 8 different wavelengths. Such sources include gas lasers, multiple diode pumped solid state lasers combined through a fiber coupler, filtered Xenon Arc lamps, tunable lasers, or the more novel Spectralum Light Engine, soon to be offered by Tidal Photonics. The Spectralum Light Engine uses prism to spectrally separate light. The spectrum is projected onto a Texas Instruments Digital Light Processor, which can selectively reflect any portion of the spectrum into a fiber or optical connector. This system is capable of monitoring and calibrating the power output across individual wavelengths to keep them constant so as to automatically compensate for intensity differences as bulbs age or between bulb changes. The following table represents examples of possible lasers, dyes and filters:

| laser | excitation filter | emission filter | Dye | |
|---|---|---|---|---|
| 407 nm | 405/12 | 436/12 | Alexa-405 | 401/421 |
| 407 nm | 405/12 | 546/10 | cascade yellow | 409/558 |
| 488 nm | 488/10 | 514/11 | Alexa-488 | 492/517 |
| 543 nm | 546/10 | 540/565 | Tamra Bodipy | 540/565 |
| 543 nm | 546/10 | 620/12 | 577/618 | 577/618 |
| | 546/10 | 620/12 | Alexa-594 | 594/613 |
| 635 nm | 635/11 | 650/11 | Alexa-635 | 632/647 |
| 635 nm | 635/11 | | Alexa700 | 702/723 |

In one aspect, imaging is accomplished through a 100× objective. The excitation light source is an 80 milliwatt diode pumped solid state laser. This light source has been used successfully with TIRFM and EPI illumination techniques. The images are acquired using a 1.3 mega pixel Hamamatsu orca-er-ag camera and a Ziess axiovert 200 inverted microscope. This configuration currently images DNBs bound randomly to a substrate at a 0.5 seconds exposure time.

For handling multiple hybridization cycles a robotic station that is fully integrated with both the reaction chamber and detection system can be implemented for use with the present invention. Epifluorescence can be used for detecting greater than 10-20 fluorescent molecules per target site. An advantage of using epifluorescence is that it allows the use of probes of multiple colors with standard microscopes.

In one aspect, a two piece flow cell is used to house a 1" square, 170 μm thick cover slip, which has been derivatized and activated to bind DNBs. A side port is connected to a syringe pump that "pulls" or "pushes" fluid from the flow cell. A second port is connected to a funnel like mixing chamber that is equipped with a liquid level sensor. The solutions are dispensed into the mixing chamber, mixed if needed, then drawn into the flow cell. When the level sensor detects air in the funnel's connection to the flow cell, the pump is reversed a known amount to back the fluid up to the funnel. This prevents air from entering the flow cell. This chamber has worked well for cover slip sized substrates and may be used in modified form for the larger substrates. Such a three-axis robotic gantry pipetting system integrated with the hybridization chamber and imaging subsystem can be functionalized for fully automated probe pipetting.

Fiducials

Figure 5:
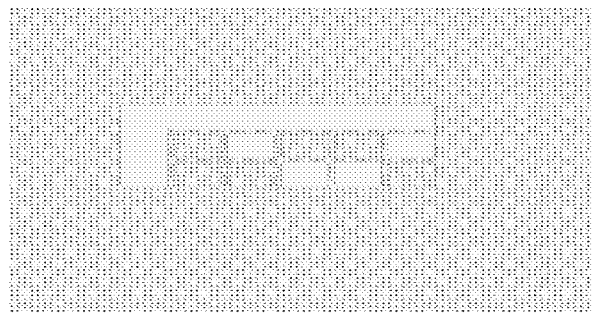
FIG. 5 illustrates reference patterns on an ordered array.

In one embodiment, the regular pattern of capture cells is interrupted in such a way as to encode location information into each acquired image. Approximately 1000 cells per image can be removed from the pattern to create a 10 bit code, which would represent up to 1024 named locations on each substrate (FIG. 5).

The physical features of the coding region can be used as a reference to locate all pixels in the image during image analysis, while the code itself is used to verify that the instrument imaged the correct area of the substrate. A key feature of the coding region is that each element is represented by a no-binding spots "empty area" block. This eliminates the need for fluorescent markers on the substrate. RCR products which are positive for a given probe-set define each element's borders. This means that the region would still be recognizable even if only 5% to 10% of RCR products bound to the surface are positive for a given probe pool. In one embodiment, the code is readable if each coding element represents 50 capture cells Kits of the Invention In the commercialization of the methods described herein, certain kits for construction of random arrays of the invention and for using the same for various applications are particularly useful. Kits for applications of random arrays of the invention include, but are not limited to, kits for determining the nucleotide sequence of target polynucleotides. A kit typically comprises at least one support having a surface and one or more reagents necessary or useful for constructing a random array of the invention or for carrying out an application therewith. Such reagents include, without limitation, nucleic acid primers, probes, adaptors, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In another aspect the invention provides kits for sequencing a target polynucleotide comprising the following components: (i) a support having a planar surface having an array of optically resolvable discrete spaced apart regions, wherein each discrete spaced apart region has an area of less than 1 $\mu m^2$; (ii) a first set of probes for hybridizing to a plurality of concatemers randomly disposed on the discrete spaced apart regions, the concatemers each containing multiple copies of a DNA fragment of the target polynucleotide; and (iii) a second set of probes for hybridizing to the plurality of concatemers such that whenever a probe from the first set hybridizes contiguously to a probe from the second set, the probes are ligated. Such kits may further include a ligase, a ligase buffer, and a hybridization buffer. In some embodiments, the discrete spaced apart regions may have capture oligonucleotides attached and the concatemers may each have a region complementary to the capture oligonucleotides such that said concatemers are capable of being attached to the discrete spaced apart regions by formation of complexes between the capture oligonucleotides and the complementary regions of said concatemers.

In another aspect, the invention includes kits for circularizing DNA fragments. In an exemplary embodiment, such a kit includes the components: (a) at least one adaptor oligonucleotide for ligating to one or more DNA fragments and forming DNA circles therewith (b) a terminal transferase for attaching a homopolymer tail to said DNA fragments to provide a binding site for a first end of said adaptor oligonucleotide, (c) a ligase for ligating a strand of said adaptor oligonucleotide to ends of said DNA fragment to form said DNA circle, (d) a primer for annealing to a region of the strand of said adaptor oligonucleotide, and (e) a DNA polymerase for extending the primer annealed to the strand in a rolling circle replication reaction. In a further embodiment, the above adaptor oligonucleotide may have a second end having a number of degenerate bases in the range of from 4 to 12. The above kit may further include reaction buffers for the terminal transferase, ligase, and DNA polymerase.

In still another aspect, the invention includes a kit for circularizing DNA fragments using a CircLigase™ enzyme (Epicentre Biotechnologies, Madison, Wis.), which kit comprises a volume exclusion polymer. In a further embodiment, the kit includes the following components: (a) reaction buffer for controlling pH and providing an optimized salt composition for CircLigase, and (b) CircLigase cofactors. In another aspect, a reaction buffer for such kit comprises 0.5 M MOPS (pH 7.5), 0.1 M KCl, 50 mM MgCl$_2$, and 10 mM DTT. In another aspect, such kit includes CircLigase, e.g. 10-100 µL CircLigase solution (at 100 unit/µL). Exemplary volume exclusion polymers are disclosed in U.S. Pat. No. 4,886,741, which is incorporated by reference, and include polyethylene glycol, polyvinylpyrrolidone, dextran sulfate, and like polymers. In one aspect, polyethylene glycol (PEG) is 50% PEG4000. In one aspect, a kit for circle formation includes the following:

| Amount | Component | Final Conc. |
|---|---|---|
| 2 µL | CircLigase ™ 10X reaction buffer | 1X |
| 0.5 µL | 1 mM ATP | 25 µM |
| 0.5 µL | 50 mM MnCl$_2$ | 1.25 mM |
| 4 µL | 50% PEG4000 | 10% |
| 2 µL | CircLigase ™ ssDNA ligase (100 units/µL) | 10 units/µL |
|  | single stranded DNA template | 0.5-10 pmol/µL |
|  | sterile water |  |

Final reaction volume: 20 µL.

The above components can be used in a number of different protocols known in the art, for example: (1) Heat DNA at 60-96° C. depending on the length of the DNA (ssDNA templates that have a 5'-phosphate and a 3'-hydroxyl group); (2) Preheat 2.2× reaction mix at 60° C. for about 5-10 min; (3) If DNA was preheated to 96° C. cool it down at 60° C. Mix DNA and buffer at 60° C. without cooling it down and incubate for 2-3 h; (4) Heat-inactivate enzyme to stop the ligation reaction.

The present invention may be better understood by reference to the following non-limiting Examples, which are provided as exemplary of the invention. The following examples are presented in order to more fully illustrate preferred embodiments of the invention, but should in no way be construed as limiting the broad scope of the invention.

EXAMPLES

Example 1

RCR Based Formation and Attachment of DNBs

Two synthetic targets were co-amplified. About one million molecules were captured on the glass surface, and then probed for one of the targets. After imaging and photobleaching the first probe, the second target was probed. Successive hybridization with amplicon specific probes showed that each spot on the array corresponded uniquely to either one of the two amplicon sequences. It was also confirmed that the probe could be removed through heating to 70° C. and then re-hybridized to produce equally strong signals.

Example 2

Validation of Circle Formation and Amplification

Figure 6:
FIG. 6 shows random arrays imaged on a rSBH instrument.

The circle formation and amplification process was validated using E. coli DNA (FIG. 6). A universal adaptor, which also served as the binding site for capture probes and RCR primer, was ligated to the 5' end of the target molecule using a universal template DNA containing degenerate bases for binding to all genomic sequences. The 3' end of the target molecule was modified by addition of a poly-dA tail using terminal transferase. The modified target was then circularized using a bridging template complementary to the adaptor and to the oligo-dA tail.

Example 3

Validation of Ligation with Condensed Concatemers

The ability for probe ligation to occur with the condensed concatemers was tested. Reactions were carried out at 20° C. for 10 min using ligase, followed by a brief wash of the chamber to remove excess probes. The ligation of a 6-mer and a labeled 5-mer produced signal levels comparable to that of an 11-mer. Software modules, including image analysis of random arrays, were tested on simulated data for whole genome sequence reconstruction.

Example 4

Identification of Targets from Multiple Pathogens Using a Single Array

Figure 7:
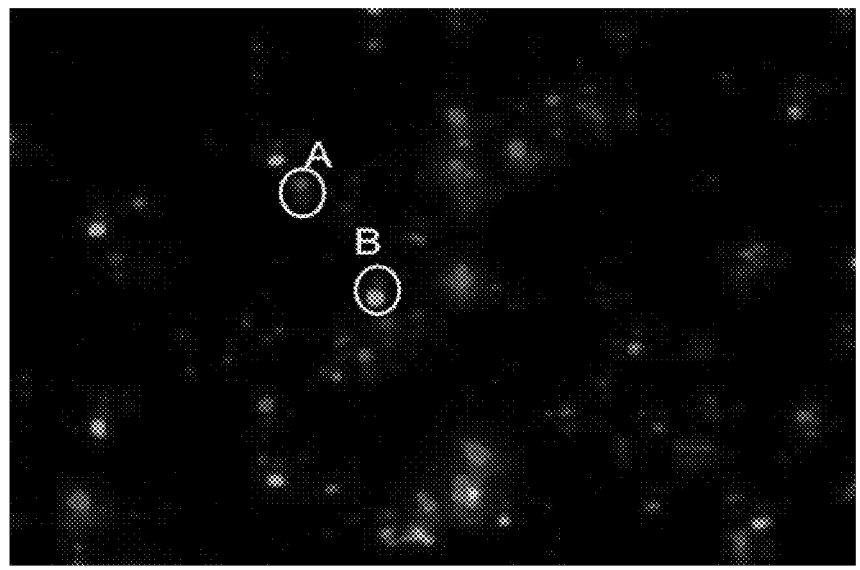
FIG. 7 shows three array images overlaid with slight shifts for easier viewing.
Figure 8:
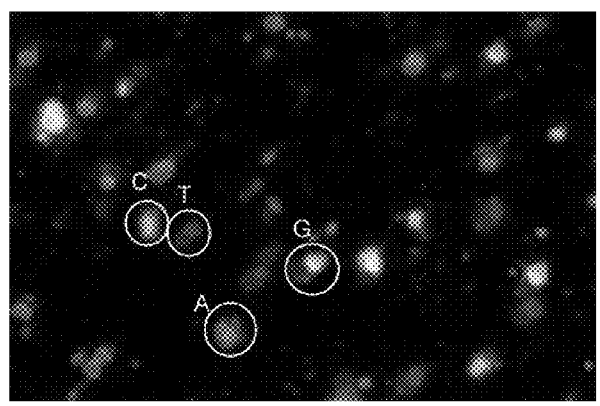
FIG. 8 shows five array images overlaid with slight shifts.

PCR products from diagnostic regions of *Bacillus anthracis* and *Yersinia pestis* were converted into single stranded DNA and attached to a universal adaptor. These 2 samples were then mixed and replicated together using RCR and deposited onto the chip surface as a random array. Successive hybridization with amplicon specific probes showed that each spot on the array corresponded uniquely to either one of the two amplicon sequences and that they can be identified specifically with the probes (FIG. 7), thus demonstrating sensitivity and specificity for identifying DNA present in submicron size DNA nano-balls having about 100-1000 copies of a DNA fragment generated by the RCR reaction.

A 155 bp amplicon sequence from *B. anthracis* and a 275 bp amplicon sequence from *Y. pestis* were amplified using standard PCR techniques with PCR primers in which one primer of the pair was phosphorylated. A single stranded form of the PCR products was generated by degradation of the phosphorylated strand using lambda exonuclease. The 5' end of the remaining strand was then phosphorylated using T4 DNA polynucleotide kinase to allow ligation of the single stranded product to the universal adaptor. The universal adaptor was ligated using T4 DNA ligase to the 5' end of the target molecule, assisted by a template oligonucleotide complementary to the 5' end of the targets and 3' end of the universal adaptor. The adaptor ligated targets were then circularized using bridging oligonucleotides with bases complementary to the adaptor and to the 3' end of the targets. Linear DNA molecules were removed by treating with exonuclease I. RCR were generated by mixing the single-stranded samples and using Phi29 polymerase to replicate around the circularized adaptor-target molecules with the bridging oligonucleotides as the initiating primers. The RCR products were captured on the glass slide via the capture oligonucleotide, which was attached to derivatized glass coverslips and was complementary to the universal adaptor sequence.

Arrayed target nano-ball molecules derived from *B. anthracis* and *Y. pestis* PCR amplicons were probed sequentially with TAMRA-labeled 11-mer probes complementary to the universal adaptor sequence, or 11-mer probes complementary to one of the two amplicon sequences By overlaying the images obtained from successive hybridization of 3 probes, (FIG. 7) it can be seen that most of the arrayed molecules that hybridized with the adaptor probe (blue spots) would only hybridize to either the amplicon 1 probe (red spots) or the amplicon 2 probe (green spots), with very few that would hybridize to both. This specific hybridization pattern demonstrated that each spot on the array contained only one type of sequence, either the *B anthracis* amplicon or the *Y. pestis* amplicon. It also demonstrated that the rSBH process was able to distinguish target molecules of different sequences deposited onto the array by using sequence specific probes.

Example 5

Decoding Base Position in Arrayed DNBs Created from 80-Mer Oligonucleotide with Degenerate Bases Individual molecules of a synthetic oligonucleotide containing a degenerate base were divided into 4 sub-populations, each having either an A, C, G or T base at that particular position. An array of DNBs created from this synthetic DNA can have about 25% of spots with each of the bases. Four successive hybridization and ligation of pairs of probes specific to each of the 4 bases identified the sub-populations (FIG. 8).

A 5' phosphorylated, 3' TAMRA-labeled pentamer oligonucleotide was paired with one of the four hexamer oligonucleotides. Each of these 4 ligation probe pairs hybridize to either an A, C, G or T-containing version of the target. Discrimination scores of greater than 3 were obtained for most targets, demonstrating the ability to identify single base differences between the nanoball targets. The discrimination score is the highest spot score divided by the average of the other 3 base-specific signals of the same spot. Adjusting the assay conditions (buffer composition, concentrations of all components, time and temperature of each step in the cycle) can result in higher signal to background allowing for calculation of full match to mismatch ratios.

A similar ligation assay was performed on the spotted arrays of 6-mer probes. In this case full-match/background ratio was about 50 and the average full match/mismatch ratio was 30. The results further demonstrated the ability to determine partial or complete sequences of DNA present in DNBs by increasing the number of consecutive probe cycles or by using 4 or more probes labeled with different dyes per each cycle.

To identify the sub-populations, a set of 4 ligation probes specific to each of the 4 bases was used. A 5' phosphorylated, 3' TAMRA-labeled pentamer oligonucleotide corresponding to position 33-37 of T1A with sequence CAAAC (probe T1A9b) was paired with one of the following hexamer oligonucleotides corresponding to position 27-32: ACTGTA (probe T1A9a), ACTGTC (probe T1A10a), ACTGTG (probe T1A11a), ACTGTT (probe T1A12a). Each of these 4 ligation probe pairs should hybridize to either an A, C, G or T containing version of T1A. For each hybridization cycle, the probes were incubated with the array in a ligation/hybridization buffer containing T4 DNA ligase at 20° C. for 5 minutes. Excess probes were washed off at 20° C. and images were taken with the TIRF microscope. Bound probes were stripped to prepare for the next round of hybridization.

An adaptor specific probe (BrPrb3) was hybridized to the array to establish the positions of all the spots (FIG. 8). The 4 ligation probe pairs, at 0.4 μM, were then hybridized successively to the array: the spots hybridized to the A-specific ligation probe pair are shown as red in FIG. 5, the C-specific spots are green, G-specific spots are yellow and the T-specific spots are cyan. In FIG. 5, circle A indicates the position of one of the spots hybridized to both the adaptor probe and the A-specific ligation probe pair, suggesting that the DNA arrayed at this spot is derived from a molecule of T1A that contains an A at position 32. It is clear that most of the spots associated with only one of the 4 ligation probe pairs, allowing identification of the base at position 32 to be determined specifically.

Using an in-house image analysis program, spots were identified using the images taken for the hybridization cycle using the adaptor probe. The same spots were also identified, and the fluorescent signals were quantified for subsequent cycles, with the base-specific ligation probes. A discrimination score was calculated for each signal for each base-specific signal of each spot. The discrimination score is the spot score divided by the average of the other 3 base-specific signals of the same spot. For each spot, the highest of the 4 base-specific discrimination scores was compared with the second highest score. If the ratio of the two was above 1.8, then the base corresponding to the maximum discrimination score was selected for the base calling. In this analysis over 500 spots were successfully base-called and the average discrimination score was 3.34. The average full match signal was 272, while the average single mismatch signal (signals from the un-selected bases) was 83.2. Thus the full match/mismatch ratio was 3.27. The image background noise was calculated by quantifying signals from randomly selected empty spots and the average signal of these empty spots was 82.9. Thus the full match/background noise ratio was 3.28. In these experiments the mismatch discrimination was limited by the low full match signal relative to the background.

Example 6

Decoding 2 Degenerate Bases at the End of a Synthetic 80-Mer Oligonucleotide Using a Probe-Anchor Ligation Assay A synthetic oligonucleotide containing 8 degenerate bases at the 5' end was used to simulate random genomic DNA ends. The DNA-nanoballs created from this oligonucleotide will have these 8 degenerate bases placed directly next to the adaptor sequence. To demonstrate the feasibility of sequencing the 2 unknown bases adjacent to the known adaptor sequence using a probe-anchor ligation approach, a 12-mer oligonucleotide with a specific sequence to hybridize to the 3' end of the adaptor sequence was used as the anchor, and a set of 16 TAMRA-labeled oligonucleotides in the form of BBNNNNNN were used as the sequence-reading probes.

Using a subset of the BBNNNNNN probe set (namely GA, GC, GG and GT in the place of BB), spots could be identified on the nano-ball array created from targets that specifically bind to one of these 4 probes, with an average full match/mismatch ratio of over 20 (FIG. 9).

Example 7

Producing Structured Nano-Ball Arrays

Ordered array lines of capture probe separated on average by 5 um were prepared. Lines were produced by using a pulled glass capillary beveled at 45 degrees to a tip size of 5 μm, loaded with 1 μl of 5 μM capture probe in water, and drawn across the glass slide by a precision gantry robot. DNBs were allowed to attach to the surface of the coverslip and then detected with a probe specific for the adaptor. FIG. 10 shows the high density attachment to regions where a capture probe was deposited on the surface, indicating that DNBs can be arranged in a grid if a substrate with submicron binding sites is prepared.

Example 8

Demonstrating Circle Formation with Multiple Adaptors

A synthetic target DNA of 70 bases in length and a PCR derived fragment of 200-300 bp in length was obtained from a double stranded product by phosphorylation of one of the primers and treatment with lambda exonuclease to remove the phosphorylated strand. The single stranded fragment was ligated to an adaptor for circularization. Polymerization, type IIs restriction enzyme digestion and re-ligation with a new adaptor was performed as described herein.

Demonstration that the process was successful was accomplished using RCR amplification of the final derived circles. Briefly, the DNA circles were incubated with primer complementary to the last introduced adaptor and Phi29 polymerase for 1 hour at 30° C. to generate a single concatemer molecule consisting of hundreds of repeated copies of the original DNA circle. Attachment of the RCR products to the surface of coverslips could also be accomplished by utilizing an adaptor sequence in the concatemer that is complementary to an attached oligonucleotide on the surface. Hybridization of adaptor unique probes was used to demonstrate that the individual adaptors were incorporated into the circle and ultimately the RCR product. To demonstrate that the adaptors were incorporated at the expected positions within the circle, sequence specific probes (labeled 5-mers) were used for the synthetic or PCR derived sequence such that ligation may occur to an unlabeled anchor probe that recognizes the terminal sequence of the adaptor. Cloning and sequencing were also used to verify DNA integrity. The process was simplified by generating clean ssDNA after each circle cutting which allowed the use of the same circle closing chemistry for each of the adaptor incorporations.

What is claimed is:

1. A method of identifying a nucleotide at a detection position of a target nucleic acid, wherein said target nucleic acid comprises a plurality of detection positions, said method comprising:

(a) providing a plurality of concatemers immobilized on a surface, wherein said surface comprises a plurality of discrete regions and said plurality of concatemers are randomly disposed on said discrete regions such that at least 70 percent of said concatemers are individually resolvable and such that at least 70 percent of said concatemers have a nearest neighbor distance of 200 nm or greater, wherein each concatemer comprises multiple copies of a monomer and each monomer comprises:

(i) a first target domain of said target nucleic acid comprising a first set of target detection positions;

(ii) a first adaptor;

(iii) a second target domain of said target nucleic acid comprising a second set of target detection positions; and (iv) a second interspersed adaptor, wherein said second interspersed adaptor is located between said first target domain and said second target domain, and wherein said first target domain and said second target domain are contiguous segments of said target nucleic acid; (b) detecting a nucleotide in said first set or said second set of detection positions, thereby identifying said nucleotide.

2. The method of claim 1, wherein said target nucleic acid is genomic DNA.

3. The method of claim 1, wherein said monomer is formed by a method comprising:
   (a) providing a first circular polynucleotide comprising said first adaptor and a fragment of said target nucleic acid, wherein said first adaptor comprises a recognition site for a restriction enzyme;
   (b) cleaving said first circular polynucleotide with said restriction enzyme to form a first linear construct, wherein said restriction enzyme binds to said recognition site within said first adaptor and cleaves said fragment at a distance from said recognition site, wherein said first linear construct comprises said first adaptor interposed between said first target domain and said second target domain of said target nucleic acid;
   (c) ligating said second interspersed adaptor to said first linear construct to form a second linear construct;
   (d) circularizing said second linear construct to create a second circular polynucleotide, wherein said second circular polynucleotide comprises said first adaptor, said first target domain, said second interspersed adaptor, and said second target domain in that order.

4. The method of claim 3, wherein said restriction enzyme cleaves said fragment at a distance of 2 to 20 nucleotides from said recognition site.

5. The method of claim 3, wherein said restriction enzyme cleaves said fragment at a distance of 18 to 20 nucleotides from said recognition site.

6. The method of claim 1, wherein said first adaptor and said second interspersed adaptor have a known sequence and wherein said first and second target domains are unknown genomic sequences.

7. A method of identifying a nucleotide sequence of a target nucleic acid, said method comprising:
   (a) providing a plurality of concatemers randomly disposed on a surface, wherein said surface comprises a plurality of discrete regions and said plurality of concatemers are randomly disposed on said discrete regions such that at least 70 percent of said concatemers are individually resolvable and such that at least 70 percent of said concatemers have a nearest neighbor distance of 200 nm or greater, and wherein said concatemers comprise a multiple copies of a monomer and each monomer comprises:
      (i) a first sequence of said target nucleic acid,
      (ii) a second sequence of said target nucleic acid;
      (iii) a first interspersed adaptor located between said first sequence and said second sequence, wherein said first interspersed adaptor comprises at least one anchor probe hybridization site, and wherein said first interspersed adaptor is inserted into said target nucleic acid such that said first sequence and said second sequence are contiguous segments of said target nucleic acid;
   (b) hybridizing one or more anchor probes to said concatemers to form duplexes between said anchor probes and said anchor probe hybridization sites;
   (c) hybridizing one or more sequencing probes to said concatemers to form perfectly matched duplexes between said one or more sequencing probes and said first sequence or said second sequence of said target nucleic acid;
   (d) ligating anchor probes and sequencing probes that are hybridized to adjacent positions of said concatemers to form at least one ligation product; and
   (e) detecting said at least one ligation product, thereby identifying at least one nucleotide of said first sequence or said second sequence.

8. The method of claim 7, wherein said at least one anchor probe hybridization site is adjacent or close to the 3' end of the second sequence.

9. The method of claim 7, wherein said at least one anchor probe hybridization site is adjacent or close to the 5' end of the first sequence.

10. The method of claim 7, wherein said interspersed adaptor comprises two anchor probe hybridization sites, one adjacent or close to the 5' end of said first sequence of the target nucleic acid and one adjacent or close to the 3' end of said second sequence.

11. The method of claim 7, wherein said concatemers are attached to said discrete regions through a noncovalent interaction.

12. The method of claim 7, wherein each of said discrete regions has an area of less than 1 μm².

13. The method of claim 7, wherein prior to said detecting step (e), said method further comprises removing any non-ligated anchor probes and sequencing probes.

14. The method of claim 7, wherein steps (b) through (e) are repeated a number of times.

15. The method of claim 14, wherein for each repetition of steps (b) through (e), said anchor probe hybridizes to a position shifted by at least one nucleotide from its position in the previous hybridization cycle, such that nucleotides in said first or second fragment are detected two or more times.

16. The method of claim 7, wherein said sequencing probes comprise a detectable label, and wherein said detecting step (e) comprises detecting said label.

17. The method of claim 7, wherein said first interspersed adaptor has a known sequence and wherein said first and second sequences are unknown genomic sequences.

18. The method of claim 1 or 7, wherein said surface further comprises inert inter-regional areas between said discrete regions and wherein said concatemers do not bind to said inert inter-regional areas.

19. The method of claim 1 or 7, wherein said discrete regions have a size from about 125 nm to about 250 nm.

20. The method of claim 1 or 7, wherein said discrete regions have a size from about 200 nm to about 500 nm.

21. The method of claim 1 or 7, wherein substantially all of said discrete regions have at most a single concatemer attached thereto.

22. A method of identifying a nucleotide at a detection position of a target nucleic acid, said method comprising:
   (a) providing a substrate comprising a surface, said surface comprising a plurality of immobilized concatemers, wherein each concatemer is formed by replication of a monomer such that said concatemer comprises multiple copies of said monomer, and wherein:
      (i) said monomer is formed from a target nucleic acid in which a first interspersed adaptor is inserted in the interior of said target nucleic acid, such that said first interspersed adaptor interrupts said target nucleic acid to form a first target sequence and a second target sequence;
(ii) said first and second target sequence are contiguous segments of said target nucleic acid; and
(b) detecting a nucleotide in said first set or said second target sequence, thereby identifying said nucleotide.

23. The method of claim 1, 7 or 22, wherein at least 70 percent of said concatemers have a nearest neighbor distance of 500 nm or greater.

24. The method of claim 1, 7 or 22, wherein at least 70 percent of said concatemers have a nearest neighbor distance of 700 nm or greater.

25. The method of claim 22, wherein said first interspersed adaptor has a known sequence and wherein said first and second target sequences are unknown genomic sequences.

* * * * *

SEQUENCE LISTING

```
<160> NUMBER OF SEQ ID NOS: 15

<210> SEQ ID NO 1
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(8)
<223> OTHER INFORMATION: n is a, c, g, or t
<220> FEATURE:
<221> NAME/KEY: misc_feature
<222> LOCATION: 14, 20, 26, 32, 47, 53, 67, 70
<223> OTHER INFORMATION: n is a, c, g, or t
<220> FEATURE:
<221> NAME/KEY: misc_feature
<222> LOCATION: (73)...(80)
<223> OTHER INFORMATION: n is a, c, g, or t

<400> SEQUENCE: 1
nnnnnnnngc atancacgan gtcatnatcg tncaaacgtc agtccangaa tcnagatcca      60
cttagantgn cgnnnnnnnn                                                  80

<210> SEQ ID NO 2
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 2
tatcatctgg atgttaggaa gacaaaagga agctgaggac attaacggac                 50

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 3
accttcagac cagat                                                       15

<210> SEQ ID NO 4
<211> LENGTH: 25
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(7)
<223> OTHER INFORMATION: n is a, c, t or g

<400> SEQUENCE: 4
nnnnnnngtc cgttaatgtc ctcag                                             25

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)...(22)
<223> OTHER INFORMATION: n is a, c, t, or g

<400> SEQUENCE: 5
atctggtctg aaggtnnnnn nn                                                22

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
cttttgtctt cctaacatcc                                                   20

<210> SEQ ID NO 7
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 7
agatgataat ctggtc                                                       16

<210> SEQ ID NO 8
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 8
aaaaaaattt tttt                                                         14

<210> SEQ ID NO 9
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 9
tttttttaaa aaaa                                                         14

<210> SEQ ID NO 10
<211> LENGTH: 10
```

-continued

```
<212> TYPE: DNA
<213> ORGANISM: Artificial Sequence
<220> FEATURE:
<223> OTHER INFORMATION: Synthetic oligonucleotide

<400> SEQUENCE: 10
cttactgtgc                                                          10

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
ggactaccgt ttaggcccgt gg                                            22

<210> SEQ ID NO 12
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 12
gaatgacacg                                                          10

<210> SEQ ID NO 13
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 13
cctgatggca                                                          10

<210> SEQ ID NO 14
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 14
cgcgatatcg cgatat                                                   16

<210> SEQ ID NO 15
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 15
cgatcgatcg at                                                       12
```